(12) United States Patent  
Riveiro et al.

(10) Patent No.: US 9,757,385 B2  
(45) Date of Patent: Sep. 12, 2017

(54) METHOD OF TREATING LEUKEMIA USING PHARMACEUTICAL FORMULATION CONTAINING THIENOTRIAZOLODIAZEPINE COMPOUNDS

(71) Applicant: ONCOETHIX GmbH, Lausanne (CH)

(72) Inventors: Maria E. Riveiro, Clichy (FR); Eric Raymond, Noiseau (FR)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/039,307

(22) PCT Filed: Nov. 26, 2014

(86) PCT No.: PCT/EP2014/075709  
§ 371 (c)(1),  
(2) Date: May 25, 2016

(87) PCT Pub. No.: WO2015/078929  
PCT Pub. Date: Jun. 4, 2015

(65) Prior Publication Data  
US 2017/0157141 A1 Jun. 8, 2017

Related U.S. Application Data

(60) Provisional application No. 62/080,804, filed on Nov. 17, 2014, provisional application No. 62/012,128, (Continued)

(51) Int. Cl.  
*A61K 31/55* (2006.01)  
*A61K 31/5517* (2006.01)  
(Continued)

(52) U.S. Cl.  
CPC ............ *A61K 31/5517* (2013.01); *A61K 9/10* (2013.01); *A61K 45/06* (2013.01); *A61K 47/38* (2013.01)

(58) Field of Classification Search  
CPC ................................................ A61K 31/5517  
(Continued)

(56) References Cited

U.S. PATENT DOCUMENTS

| 8,476,260 B2 * | 7/2013 | Miyoshi | ............... C07D 495/14 514/220 |
| 2007/0010466 A1 | 1/2007 | Sikic et al. | |
| 2014/0107107 A1 * | 4/2014 | Gautschi | ............... A61K 9/1635 514/220 |

FOREIGN PATENT DOCUMENTS

| EP | 1297836 A1 | 4/2003 |
| EP | 2239264 A1 | 10/2010 |

(Continued)

OTHER PUBLICATIONS

Crazzolara, R., et al., Potentiating elects of RAD001 (Everolimus) on vincristine therapy in childhood acute lymphobastic leukemia, Blood, 2009, pp. 3297-3306, 113, (14).

(Continued)

*Primary Examiner* — Nizal Chandrakumar  
(74) *Attorney, Agent, or Firm* — Catherine D. Fitch; Richard S. Parr; Janet E. Fair

(57) ABSTRACT

A method of treating leukemia in a mammal by administering a solid dispersion comprising an amorphous thienotriazolodiazepine compound of the Formula (1) wherein $R^1$ is alkyl having a carbon number of 1-4, $R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; —$NR_5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, or a pharmaceutically acceptable salt thereof or a hydrate or solvate thereof.

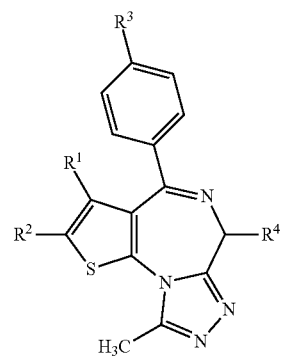

(1)

14 Claims, 26 Drawing Sheets

Related U.S. Application Data filed on Jun. 13, 2014, provisional application No. 61/909,702, filed on Nov. 27, 2013.

(51) Int. Cl.
*A61K 9/10* (2006.01)
*A61K 47/38* (2006.01)
*A61K 45/06* (2006.01)

(58) Field of Classification Search
USPC .......................................................... 514/220
See application file for complete search history.

(56) References Cited

FOREIGN PATENT DOCUMENTS

| WO | 2006020618 A1 | 2/2006 |
|---|---|---|
| WO | 2008070011 A2 | 6/2008 |
| WO | 2011143660 A2 | 11/2011 |
| WO | 2011143669 A2 | 11/2011 |
| WO | 2012140436 A1 | 10/2012 |
| WO | 2013030150 A1 | 3/2013 |
| WO | 2014001356 A1 | 1/2014 |

OTHER PUBLICATIONS

Milano, G., et al., CSF drug levels for children for acute lymphoblastic leukemia treated by 5 g/m(2) methotrexate, European Journal of Cancer and Clinical Oncology, 1990, pp. 492-495, 26, (2).

Silverman, L., et al., Phase I trial of the combination of the epigenetic modulators vorinostat and azacitidine (azaC0 in patients with the myelodysplastic syndrom (MDS) and acute myeloid leukemia (AML). An update from the NY Cancer Consortium, Leukemia Research, 2009, pp. S135-S136, 33.

* cited by examiner

FIG. 13A    48h-concomitant combinations

| Drug | CI Values | OTX015-sensitive cell lines | | | OTX015-resistant cell line |
|---|---|---|---|---|---|
| | | HL60 | U937 | Jurkat | K562 |
| Decitabine | Median<br>Min<br>Max | 0.5<br>0.1<br>1.8 | 0.9<br>0.001<br>8.7 | 0.5<br>0.04<br>7.7 | 0.3<br>0.1<br>1.9 |
| Cytarabine | Median<br>Min<br>Max | 0.9<br>0.1<br>2.5 | 1.0<br>0.3<br>1.7 | 0.7<br>0.5<br>1.8 | 1.1<br>0.2<br>7.8 |
| Daunorubicin | Median<br>Min<br>Max | 0.9<br>0.4<br>2.8 | 0.8<br>0.3<br>3.2 | 0.9<br>0.4<br>1.8 | 0.4<br>0.1<br>1.7 |
| Methotrexate | Median<br>Min<br>Max | 0.1<br>0.0<br>4.9 | 0.3<br>0.0<br>2.4 | 0.1<br>0.0<br>1.8 | 0.1<br>0.0<br>5.1 |
| Dexamethasone | Median<br>Min<br>Max | 0.3<br>0.1<br>1.2 | 1.9<br>0.5<br>9.3 | 0.2<br>0.0<br>2.0 | 0.7<br>0.3<br>2.6 |
| Everolimus | Median<br>Min<br>Max | 0.8<br>0.2<br>4.5 | 2.0<br>0.5<br>6.2 | 0.7<br>0.1<br>5.7 | 0.6<br>0.1<br>3.3 |
| Azacytidine | Median<br>Min<br>Max | 1.6<br>0.4<br>8.0 | 0.8<br>0.3<br>2.0 | 0.7<br>0.4<br>2.4 | 0.6<br>0.1<br>9.1 |
| Panobinostat | Median<br>Min<br>Max | 0.7<br>0.2<br>3.3 | 1.3<br>0.4<br>6.5 | 0.5<br>0.2<br>0.8 | 0.5<br>0.1<br>2.7 |

*FIG. 14A* Azacytidine followed by Compound (1-1)
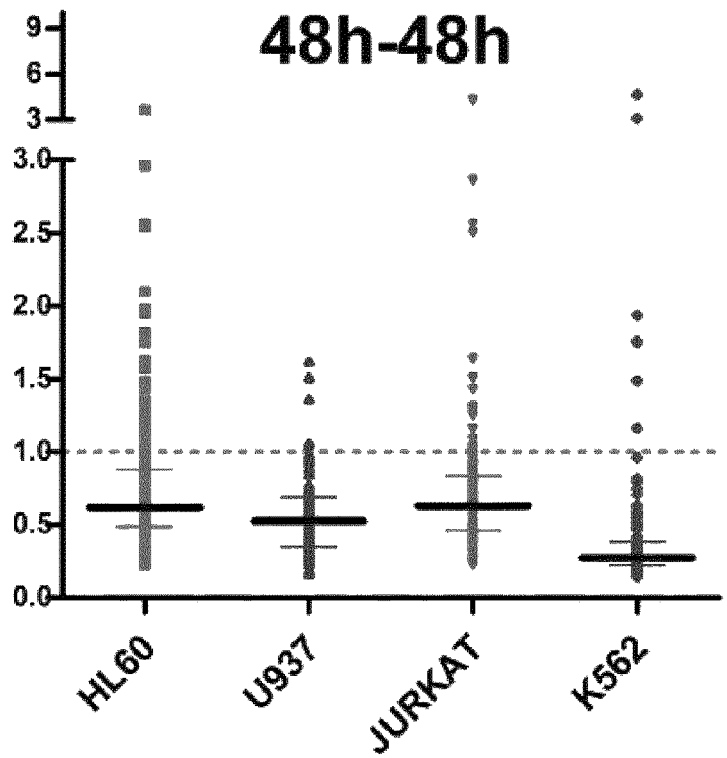
*FIG. 14B* Azacytidine followed by Compound (1-1)
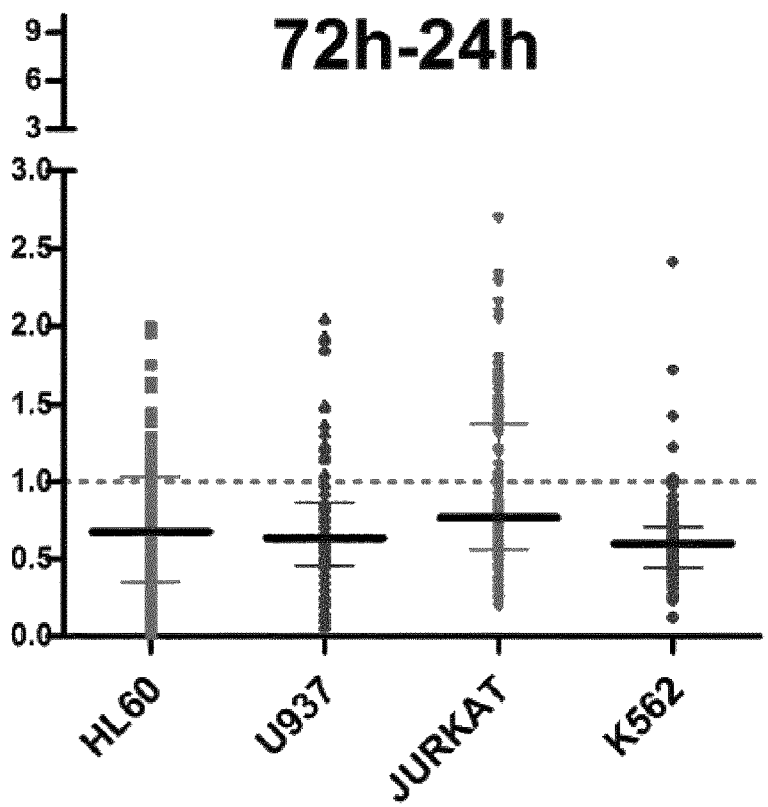

FIG. 14C Azacytidine followed by Compound (1-1)
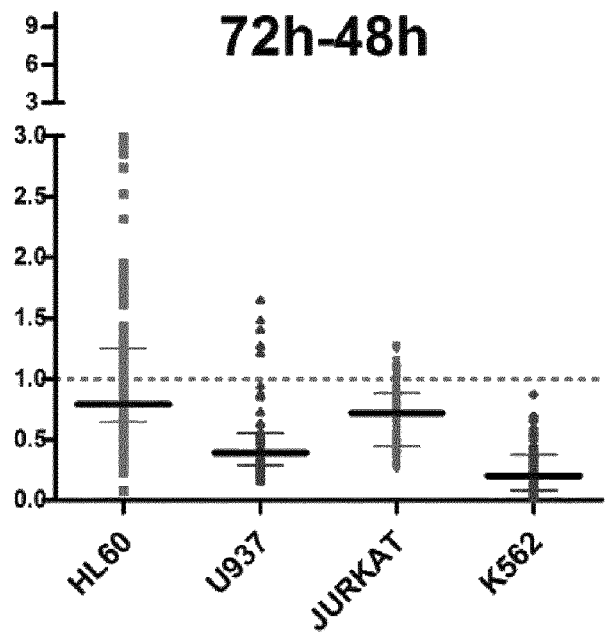
FIG. 14D Azacytidine followed by Compound (1-1)
| Schedule | CI Values | HL60 | U937 | Jurkat | K562 |
|---|---|---|---|---|---|
| Aza 48h-OTX015 48h | Median<br>Min<br>Max | 0.6<br>0.2<br>3.7 | 0.5<br>0.2<br>1.6 | 0.6<br>0.2<br>4.4 | 0.3<br>0.1<br>4.6 |
| Aza 72h-OTX015 24h | Median<br>Min<br>Max | 0.7<br>0.02<br>2.0 | 0.6<br>0.06<br>2.0 | 0.8<br>0.2<br>2.7 | 0.6<br>0.1<br>2.4 |
| Aza 72h-OTX015 48h | Median<br>Min<br>Max | 0.8<br>0.1<br>3.0 | 0.4<br>0.2<br>1.7 | 0.7<br>0.3<br>1.3 | 0.2<br>0.01<br>0.9 |

FIG. 15A   Panobinostat followed by Compound (1-1)
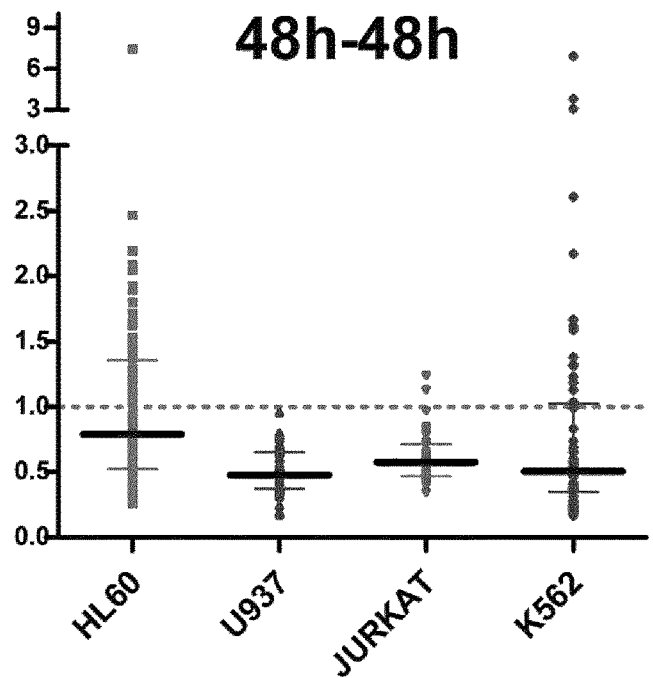
FIG. 15B   Panobinostat followed by Compound (1-1)
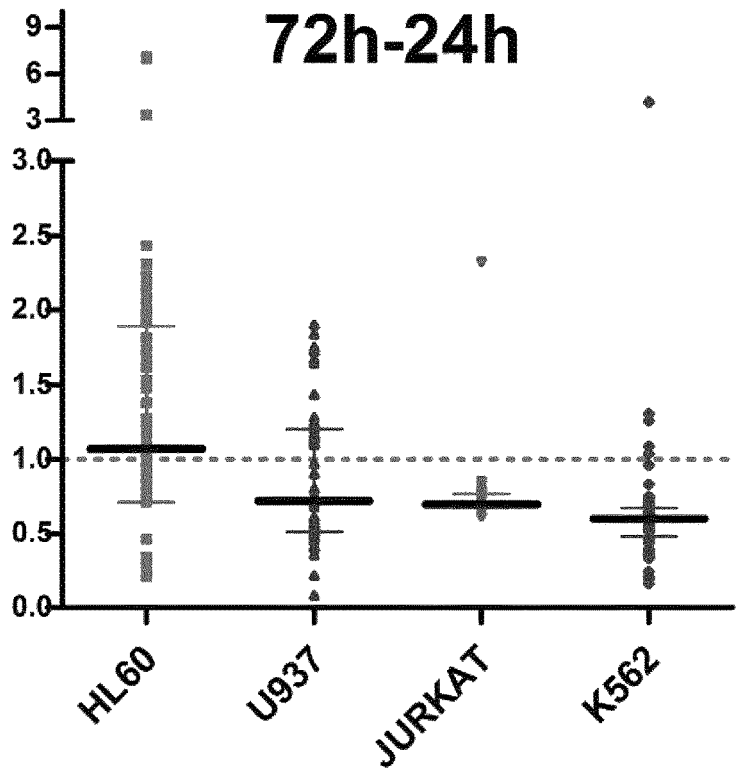

FIG. 15C Panobinostat followed by Compound (1-1)
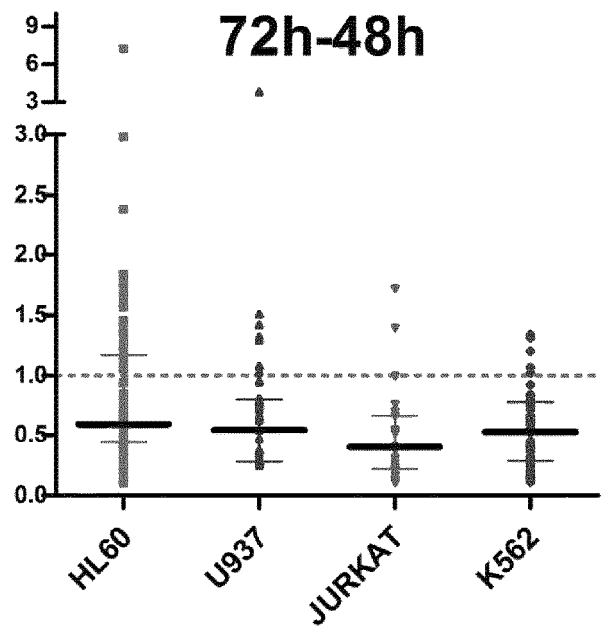
FIG. 15D Panobinostat followed by Compound (1-1)
| Schedule | CI Values | HL60 | U937 | Jurkat | K562 |
|---|---|---|---|---|---|
| Pano 48h-OTX015 48h | Median | 0.8 | 0.5 | 0.6 | 0.5 |
| | Min | 0.3 | 0.2 | 0.3 | 0.2 |
| | Max | 7.4 | 1.0 | 1.2 | 6.9 |
| Pano 72h-OTX015 24h | Median | 1.1 | 0.7 | 0.7 | 0.6 |
| | Min | 0.2 | 0.1 | 0.6 | 0.2 |
| | Max | 7.1 | 1.9 | 2.3 | 4.2 |
| Pano 72h-OTX015 48h | Median | 0.6 | 0.5 | 0.4 | 0.5 |
| | Min | 0.1 | 0.2 | 0.1 | 0.1 |
| | Max | 7.2 | 3.8 | 1.7 | 1.3 |

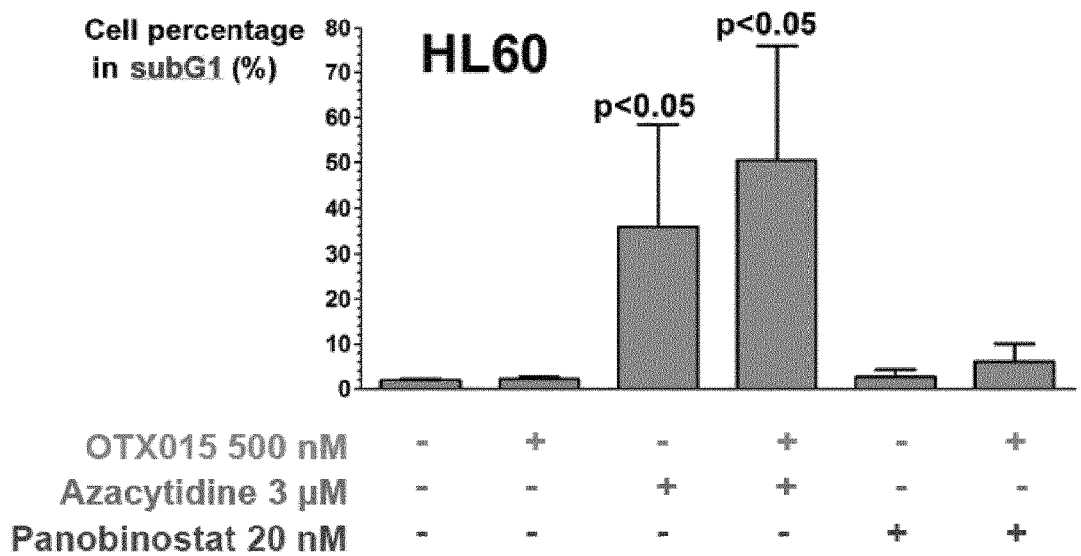
FIG. 16A  24 h concomitant OTX015 exposure with azacytidine or panobinostat
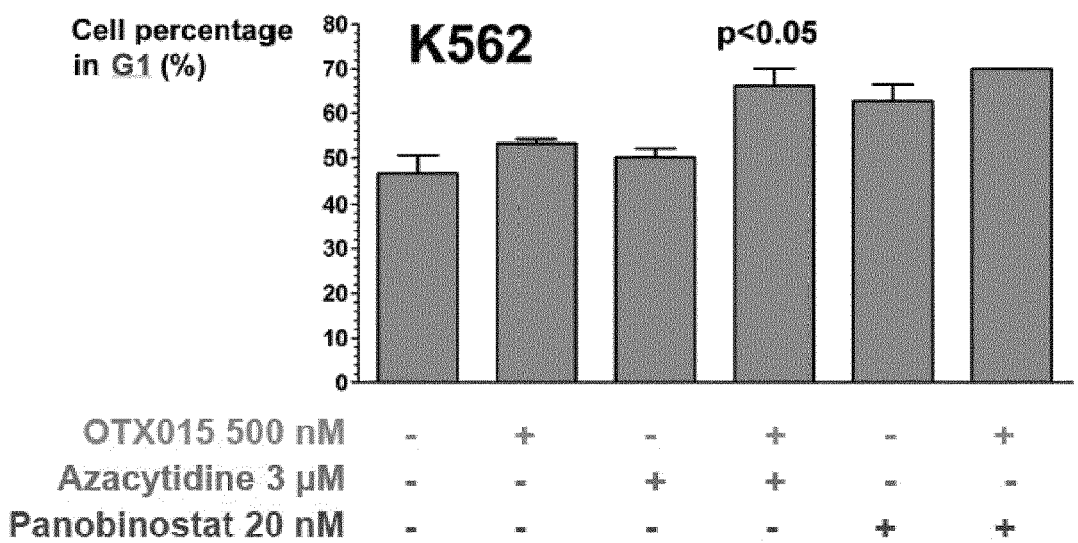
FIG. 16B  24 h concomitant OTX015 exposure with azacytidine or panobinostat

*FIG. 17A* 24 h concomitant exposure to OTX015 and azacytidine or panobinostat
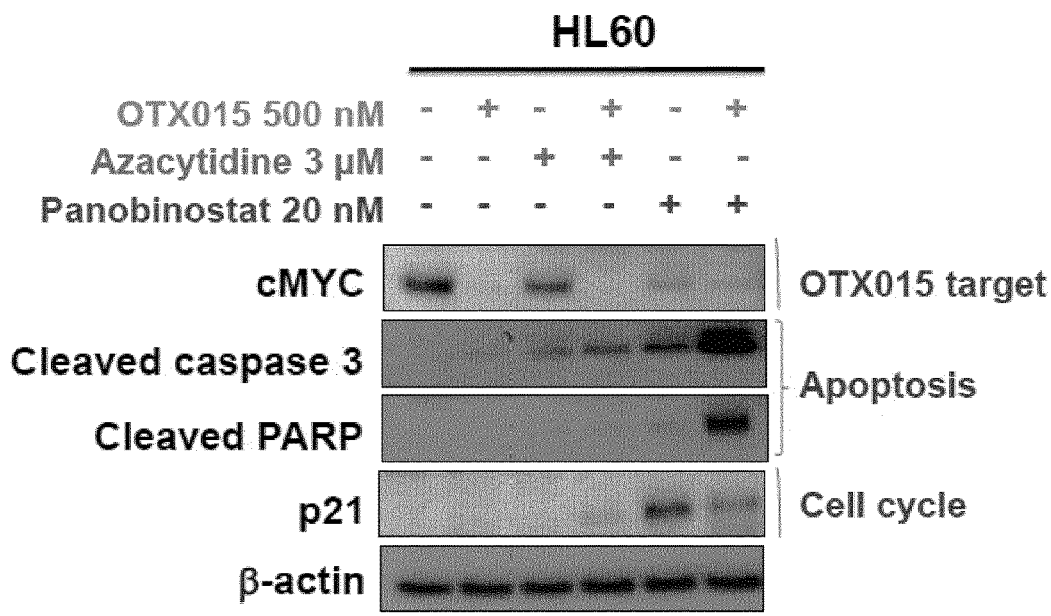
*FIG. 17B* 24 h concomitant exposure to OTX015 and azacytidine or panobinostat
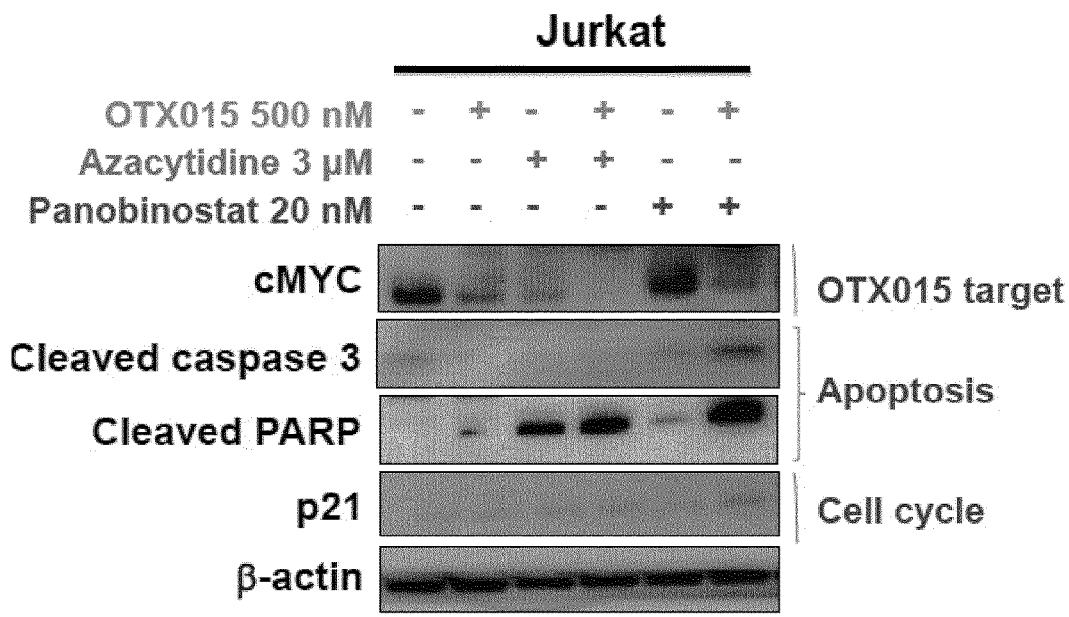

METHOD OF TREATING LEUKEMIA USING PHARMACEUTICAL FORMULATION CONTAINING THIENOTRIAZOLODIAZEPINE COMPOUNDS

CROSS-REFERENCE TO RELATED APPLICATIONS

This application is a National Stage application of PCT/EP2014/075709, filed Nov. 26, 2014, which claims the benefit of U.S. Provisional Application Ser. No. 61/909,702, filed Nov. 27, 2013, U.S. Provisional Application Ser. No. 62/012,128, filed Jun. 13, 2014, and U.S. Provisional Application Ser. No. 62/080,804, filed Nov. 17, 2014, each of which is incorporated herein by reference in its entirety.

FIELD OF INVENTION

The present disclosure describes a method of treating leukemia using thienotriazolodiazepine compounds which have improved solubility and bioavailability which may be provided in the form of solid dispersions.

BACKGROUND OF THE INVENTION

The compound of Formula (1), described herein below, has been shown to inhibit the binding of acetylated histone H4 to the tandem bromodomain (BRD)-containing family of transcriptional regulators known as the BET (bromodomains and extraterminal) proteins, which include BRD2, BRD3, and BRD4. See U.S. Patent Application Publication No. 2010/0286127 A1, which is incorporated herein by reference in its entirety. The BET proteins have emerged as major epigenetic regulators of proliferation and differentiation and also have been associated with predisposition to dyslipidemia or improper regulation of adipogenesis, elevated inflammatory profile and risk for cardiovascular disease and type 2 diabetes, and increased susceptibility to autoimmune diseases such as rheumatoid arthritis and systemic lupus erythematosus as reported by Denis, G. V. "Bromodomain coactivators in cancer, obesity, type 2 diabetes, and inflammation," *Discov Med* 2010; 10:489-499, which is incorporated herein by reference in its entirety. Accordingly, the compound of formula (II) may be useful for treatment of various cancers, cardiovascular disease, type 2 diabetes, and autoimmune disorders such as rheumatoid arthritis and systemic lupus erythematosus.

The thienotriazolodiazepine compound of Formula (1), described herein below, presents highly specific difficulties in relation to administration generally and the preparation of galenic compositions in particular, including the particular problems of drug bioavailability and variability in inter- and intra-patient dose response, necessitating development of a non-conventional dosage form with respect to the practically water-insoluble properties of the thienotriazolodiazepine.

Previously, it had been found that thienotriazolodiazepine compound of Formula (1) could be formulated with the carrier ethyl acrylate-methyl methacrylate-trimethylammonioethyl methacrylate chloride copolymer (Eudragit RS, manufactured by Rohm) to provide an oral formulation that preferentially released the pharmaceutical ingredient in the lower intestine for treatment of inflammatory bowel diseases such as ulcerative colitis and Crohn's disease as reported in U.S. Patent Application Publication No. 20090012064 A1, which is incorporated herein by reference in its entirety. Through various experiments including animal tests, it was found that that for inflammatory bowel diseases, the thienotriazolodiazepine compound of Formula (1) release in a lesion and a direct action thereof on the inflammatory lesion were more important than the absorption of thienotriazolodiazepine compound of Formula (1) into circulation from the gastrointestinal tract. However, for many other disease conditions high absorption of thienotriazolodiazepine compound of Formula (1) into the circulation from gastrointestinal tract is required. Accordingly, a need exists for formulations of thienotriazolodiazepine compound of Formula (1) that can provide high absorption of thienotriazolodiazepine compound of Formula (1) into the circulation from gastrointestinal tract.

The human BET family bromodomains, including BRD2, BRD3, BRD4 and BRDT proteins, has become a druggable target for the development of specific gene transcription inhibitors. Accordingly, there is an urgent need for novel oral BET-BRD inhibitors, as single agents or in combination with other agents for the treatment of various disease conditions, including leukemia.

BRIEF SUMMARY OF THE INVENTION

In one embodiment, the present disclosure provides for a method of treating leukemia using the compositions described herein.

In one embodiment, the present disclosure provides for a method of treating leukemia in a mammal, comprising administering to a patient in need of such treatment a pharmaceutically acceptable amount of a composition comprising a solid dispersion according to the compositions described in sections III, IV, V, VI and VII. In one embodiment, the leukemia is selected from the group consisting acute leukemia and chronic leukemia. In one embodiment, the leukemia is independently selected from the group consisting of acute lymphoblastic leukemia (ALL), acute myelogenous leukemia (AML) (or myeloblastic), chronic lymphocytic leukemia (CLL), and chronic myelogenous leukemia (CML). In another embodiment, the leukemia is independently selected from the group consisting of acute myeloid leukemia, chromic acute myeloid leukemia and acute lymphoblastic leukemia.

In one embodiment, a method of treating leukemia in accordance with the present invention comprises administering an effective amount of a compound according to Formula (1):

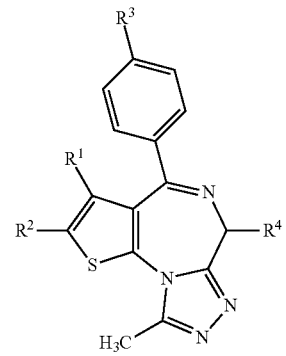

wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s), or heteroaryl optionally having substituent(s), a pharmaceutically acceptable salt thereof or a hydrate thereof; and a pharmaceutically acceptable polymer. In one such embodiment, the theinotriazolodiazepine compound is formulated as a solid dispersion comprising an amorphous thienotriazolodiazepine compound.

In one embodiment, a method of treating leukemia in accordance with the present invention comprises administering an effective amount of a compound a composition according to the present invention to a patient in need of such treatment, wherein at least a compound of Formula (1) is administered in combination with at least one other therapeutic agent, wherein the compound of Formula (1) or the pharmaceutically acceptable salt thereof and the at least one other therapeutic agent are administered either simultaneously or sequentially. In an embodiment, the one other therapeutic agent is selected from the group consisting of an epigenetic modulator, a glucocorticoid, an m-TOR inhibitor, an HDAC-inhibitor, demethylating agent, anthracycline, an analogue of cytidine and a cytotoxic drug. In one such embodiment, the demethylating agent is decitabine. In another such embodiment, the HDAC-inhibitor is vorinostat or panobinostat. In another such embodiment, the mTOR inhibitor is everolimus. In another such embodiment, the glucocorticoid is dexamethasone. In another such embodiment, the cytotoxic drug is selected from the group consisting of cytarabine or methotrexate. In another such embodiment, the analogue of cytidine is azacytidine. In another such embodiment, the anthracycline is daunorubicin.

In one embodiment, Formula (1) is selected from the group consisting of: (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]tri-azolo[4,3-a][1,4]diazepin-6-yl}acetate, (iii) methyl (S)-{2,3,9-trimethyl-4-(4-phenylaminophenyl)-6H-thieno[3,2-f][1,2,4]triaz-olo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate. In one such embodiment, Formula (1) is (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide.

In some embodiments, the pharmaceutically acceptable polymer is hydroxypropylmethylcellulose acetate succinate. In some such embodiments, the solid dispersion has a thienotriazolodiazepine compound to hydroxypropylmethylcellulose acetate succinate (HPMCAS), weight ratio of 1:3 to 1:1. In some such embodiments, the solid dispersion exhibits a single glass transition temperature (Tg) inflection point ranging from about 130° C. to about 140° C. In some such embodiments, a concentration of the thienotriazolodiazepine compound after exposure to the relative humidity of 75% at 40° C. for at least one month is at least 90% of the concentration the amorphous thienotriazolodiazepine compound prior to such exposure.

In other embodiments, the pharmaceutically acceptable polymer is PVP. In some such embodiments, the solid dispersion has a thienotriazolodiazepine compound to PVP weight ratio of 1:3 to 1:1. In some such embodiments, the solid dispersion exhibits a single glass transition temperature (Tg) inflection point ranging from about 175° C. to about 185° C. In some such embodiments, a concentration of the thienotriazolodiazepine compound after exposure to the relative humidity of 75% at 40° C. for at least one month is at least 90% of the concentration the amorphous thienotriazolodiazepine compound prior to such exposure.

In another embodiment, the solid dispersion is obtained by spray drying.

In another embodiment, the solid dispersion exhibits an X-ray powder diffraction pattern substantially free of diffraction lines associated with crystalline thienotriazolodiazepine compound of Formula (1).

In yet another embodiment, the solid dispersion provides an area under the curve (AUC) value that is at least 0.5 times that of a corresponding AUC value provided by a control composition administered intravenously, wherein the control composition comprises an equivalent quantity of a crystalline thienotriazolodiazepine compound of Formula (1).

In still yet another embodiment, the solid dispersion provides a concentration, of the amorphous thienotriazolodiazepine compound, in an aqueous in vitro test medium at pH between 5.0 to 7.0, of at least 5-fold greater than a concentration of a crystalline thienotriazolodiazepine compound of Formula (1) without polymer, in a control in vitro test medium at pH between 5.0 to 7.0 test medium.

In yet another embodiment, a concentration of the amorphous thienotriazolodiazepine compound, from the solid dispersion, in an aqueous in vitro test medium having a pH of 1.0 to 2.0, is at least 50% higher than a concentration of a crystalline thienotriazolodiazepine compound of Formula (1) without polymer in an in vitro test medium having a pH between 5.0 and 7.0.

In one embodiment, the concentration of the amorphous thienotriazolodiazepine compound, is at least 50% higher compared to a concentration of thienotriazolodiazepine compound of Formula (1), from a solid dispersion of thienotriazolodiazepine compound of the Formula (1) and a pharmaceutically acceptable polymer selected from the group consisting of: hypromellose phthalate and ethyl acrylate-methyl methacrylate-trimethylammonioethyl methacrylate chloride copolymer, wherein each solid dispersion was placed in an aqueous in vitro test medium having a pH of 1.0 to 2.0.

In one embodiment, the concentration of the amorphous thienotriazolodiazepine compound of Formula (1), is at least 50% higher compared to a concentration of thienotriazolodiazepine compound of Formula (1), from a solid dispersion of thienotriazolodiazepine compound of the Formula (1) and a pharmaceutically acceptable polymer selected from the group consisting of: hypromellose phthalate and ethyl acrylate-methyl methacrylate-trimethylammonioethyl methacrylate chloride copolymer, wherein each solid dispersion was placed in an aqueous in vitro test medium having a pH of 1.0 to 2.0.

BRIEF DESCRIPTION OF THE DRAWINGS

The foregoing summary, as well as the following detailed description of embodiments of the pharmaceutical compositions including thienotriazolodiazepine formulations and methods of the present invention, will be better understood when read in conjunction with the appended drawings of exemplary embodiments. It should be understood, however, that the invention is not limited to the precise arrangements and instrumentalities shown.

The term OTX015 is synonymous with compound (1-1) throughout the description and drawings.

In the drawings:

FIG. 1A illustrates dissolution profile of a comparator formulation comprising a solid dispersion comprising 25% compound (1-1) and Eudragit L100-55;

FIG. 1B illustrates dissolution profile of a comparator formulation comprising a solid dispersion comprising 50% compound (1-1) and Eudragit L100-55;

FIG. 1C illustrates dissolution profile of an exemplary formulation comprising a solid dispersion comprising 25% compound (1-1) and polyvinylpyrrolidone (PVP);

FIG. 1D illustrates dissolution profile of an exemplary formulation comprising a solid dispersion comprising 50% compound (1-1) and PVP;

FIG. 1E illustrates dissolution profile of an exemplary formulation comprising a solid dispersion comprising 25% compound (1-1) and PVP-vinyl acetate (PVP-VA);

FIG. 1F illustrates dissolution profile of an exemplary formulation comprising a solid dispersion comprising 50% compound (1-1) and PVP-VA;

FIG. 1G illustrates dissolution profile of an exemplary formulation comprising a solid dispersion comprising 25% compound (1-1) and hypromellose acetate succinate (HPMCAS-M);

FIG. 1H illustrates dissolution profile of an exemplary formulation comprising a solid dispersion comprising 50% compound (1-1) and HPMCAS-M;

FIG. 1I illustrates dissolution profile of an exemplary formulation comprising a solid dispersion comprising 25% compound (1-1) and hypromellose phthalate (HPMCP-HP55);

FIG. 1J illustrates dissolution profile of an exemplary formulation comprising a solid dispersion comprising 50% compound (1-1) and HMCP-HP55;

FIG. 2A illustrates results of in vivo screening of an exemplary formulation comprising a solid dispersion of 25% compound (1-1) and PVP;

Figure 1A:
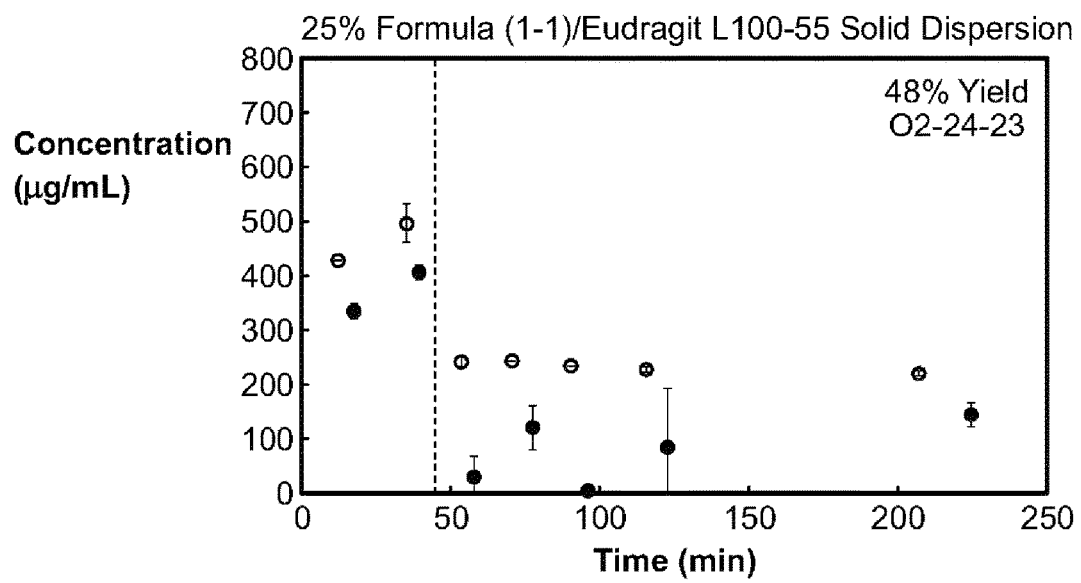
Figure 1B:
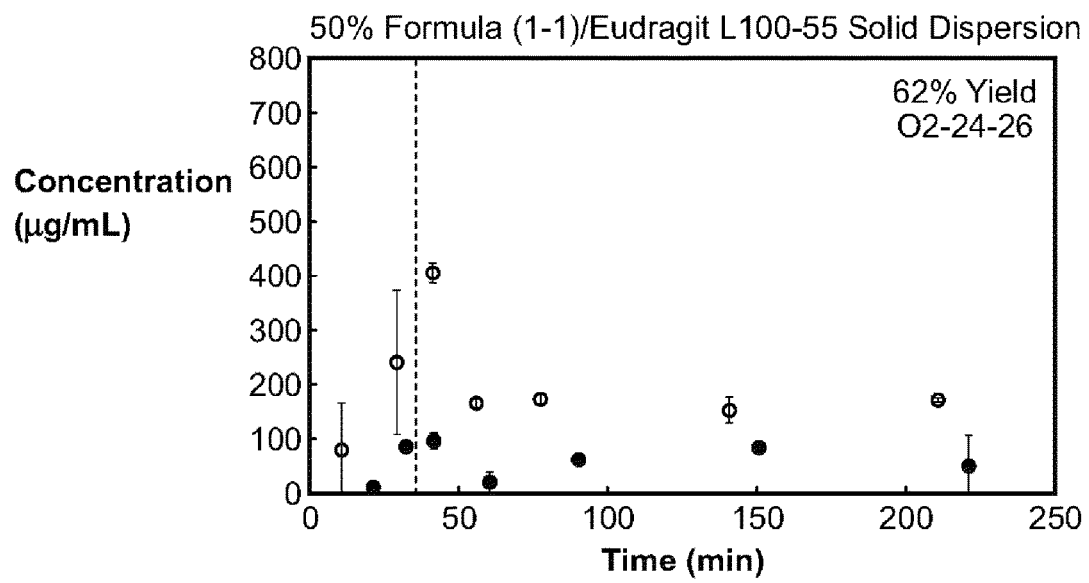
Figure 1C:
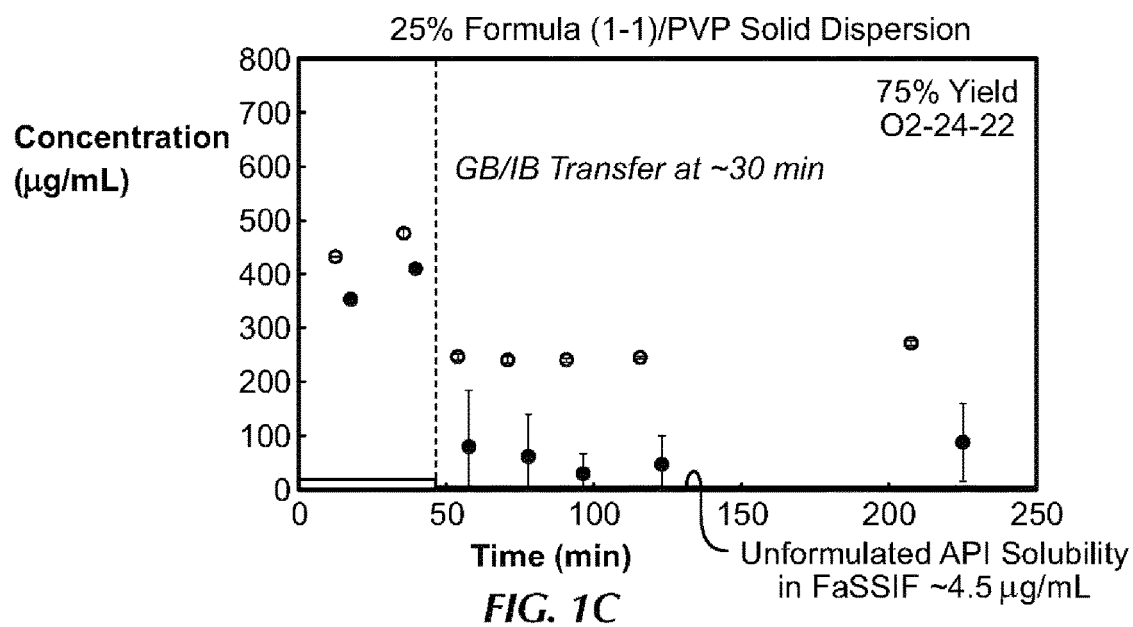
Figure 1D:
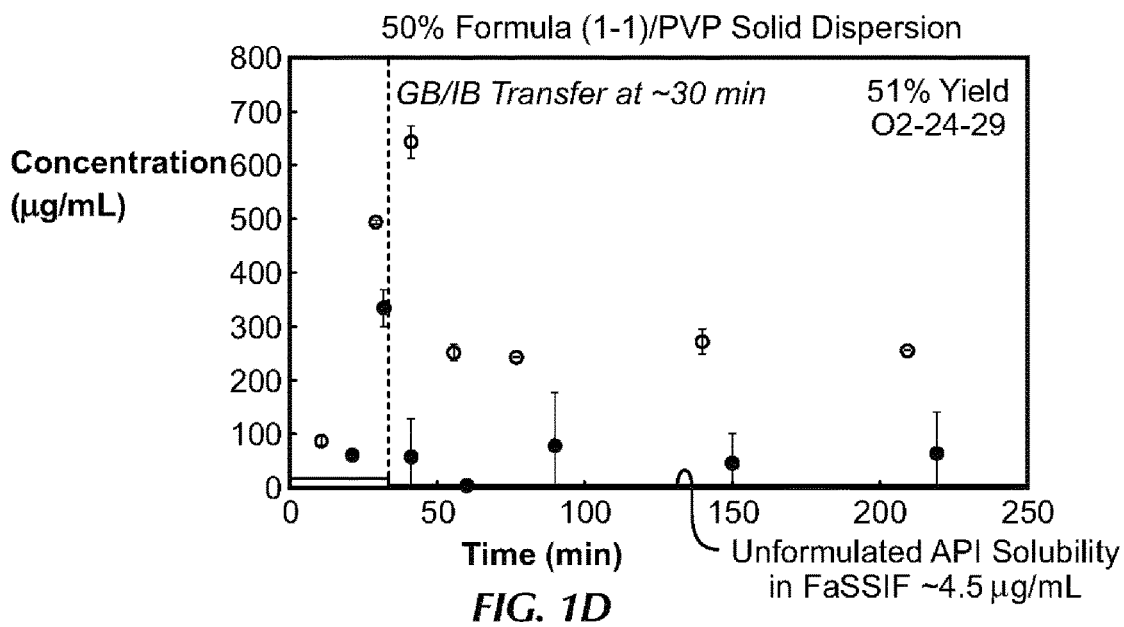
Figure 1E:
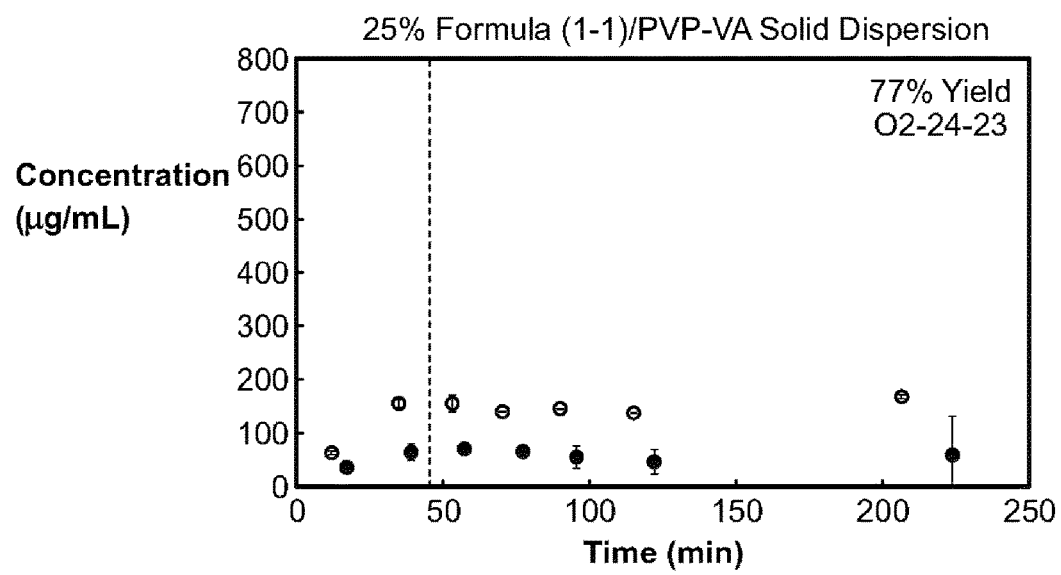
Figure 1F:
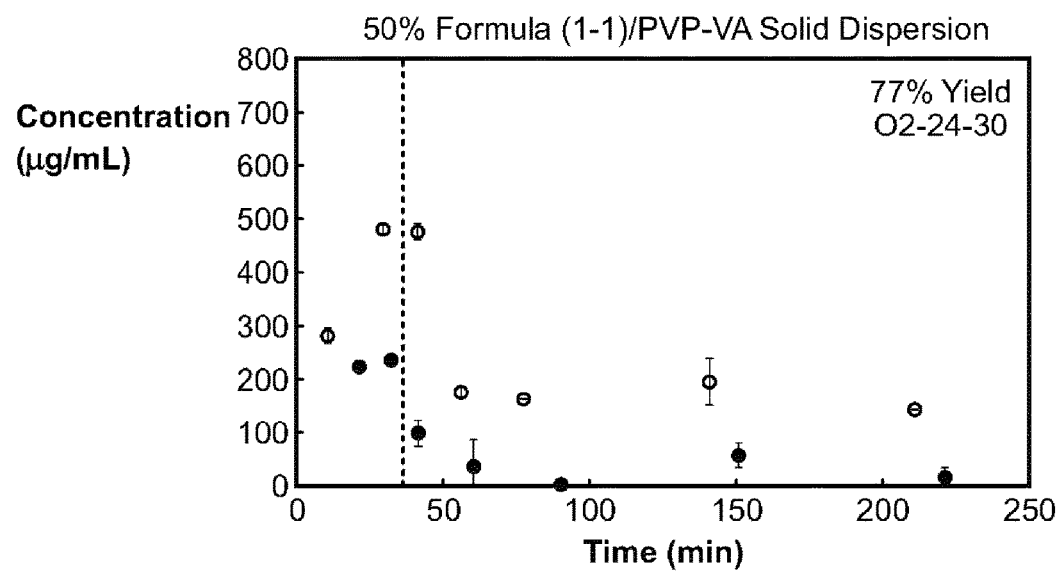
Figure 1G:
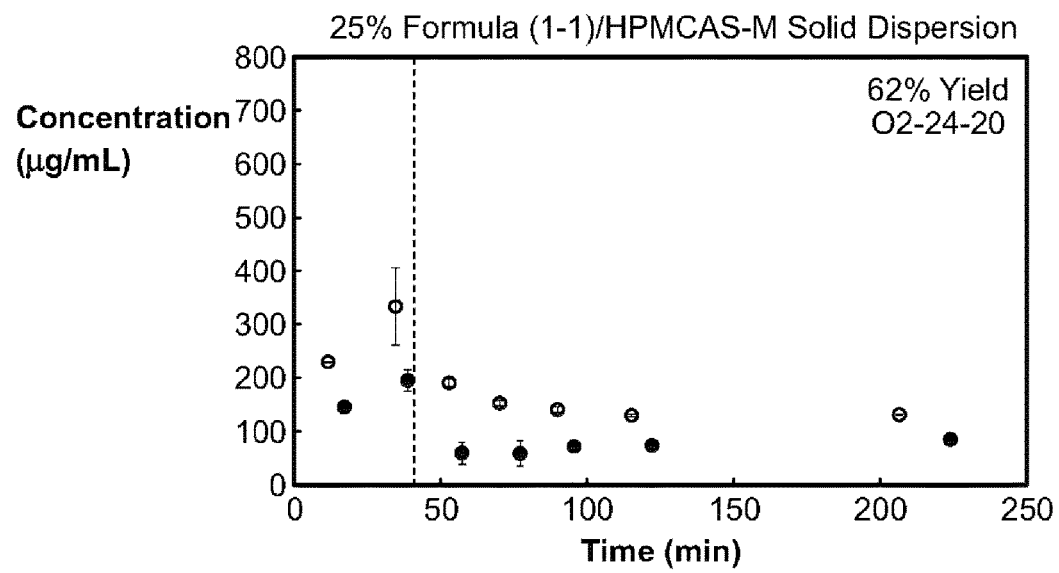
Figure 1H:
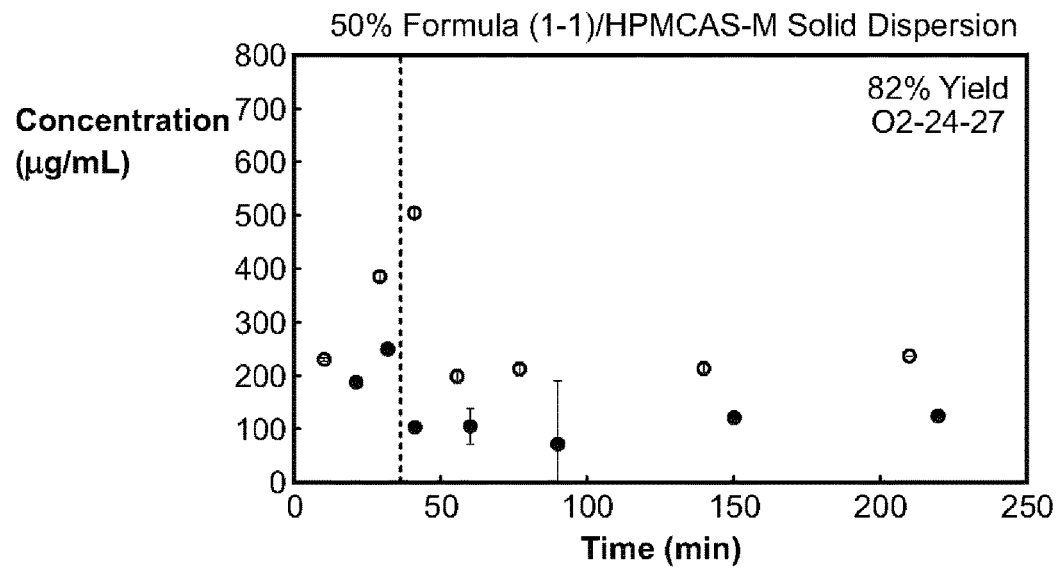
Figure 1I:
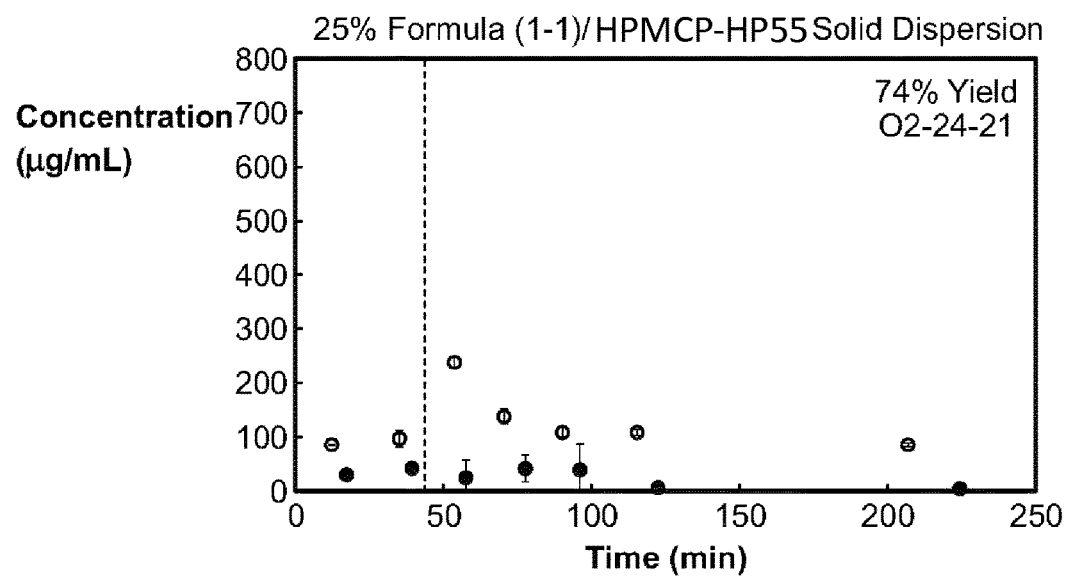
Figure 1J:
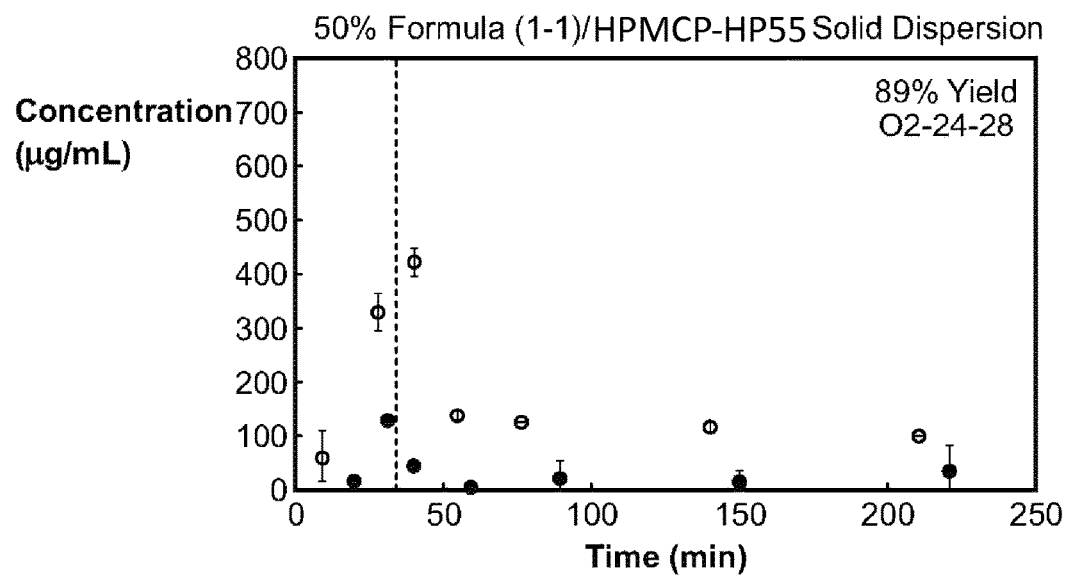
Figure 2A:
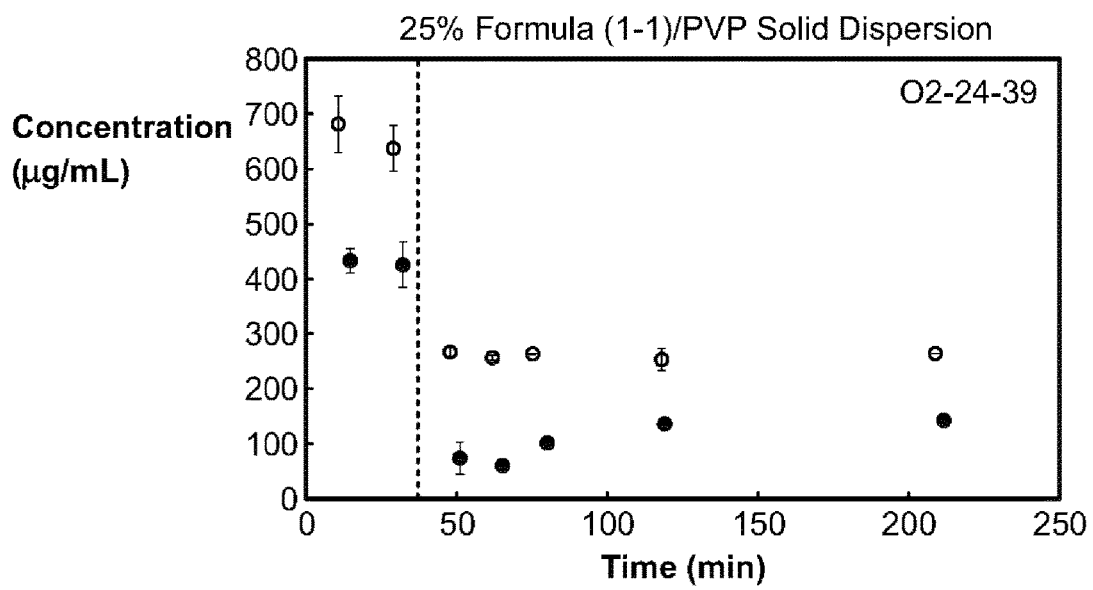
Figure 2B:
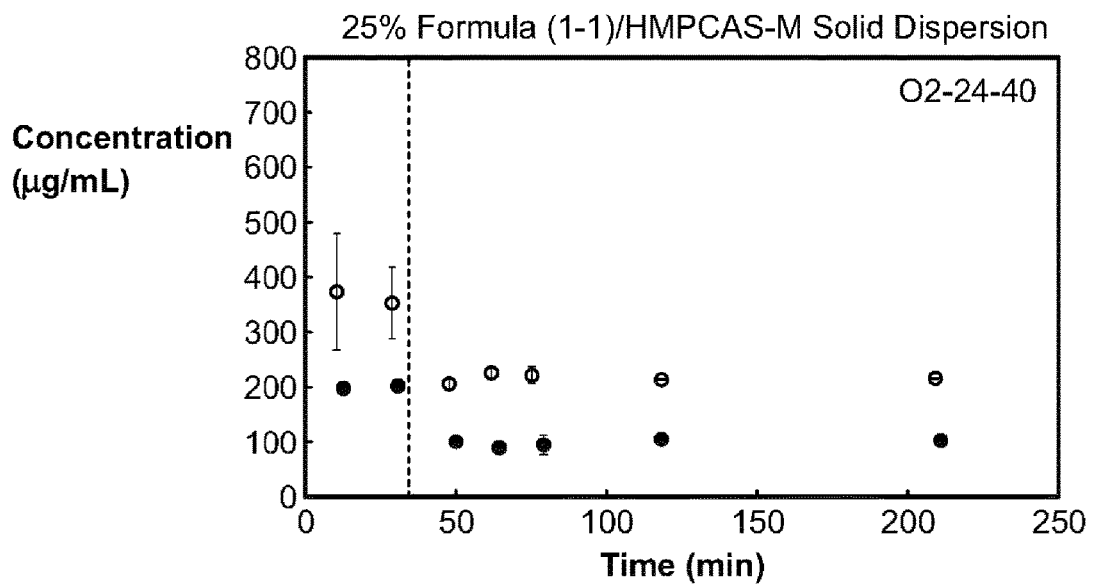
Figure 2C:
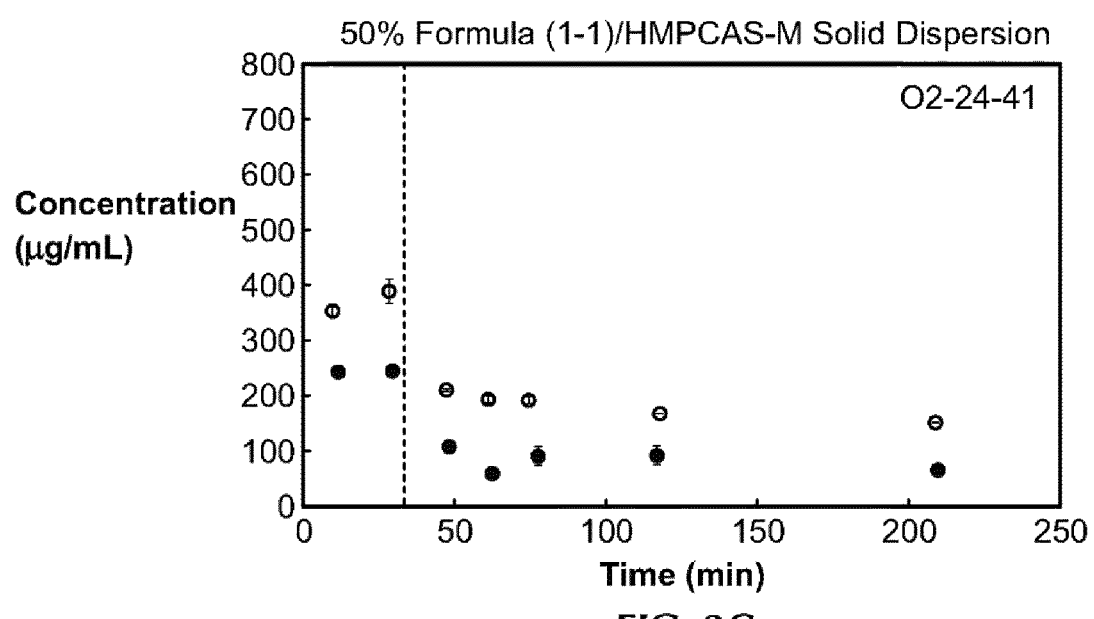
Figure 3:
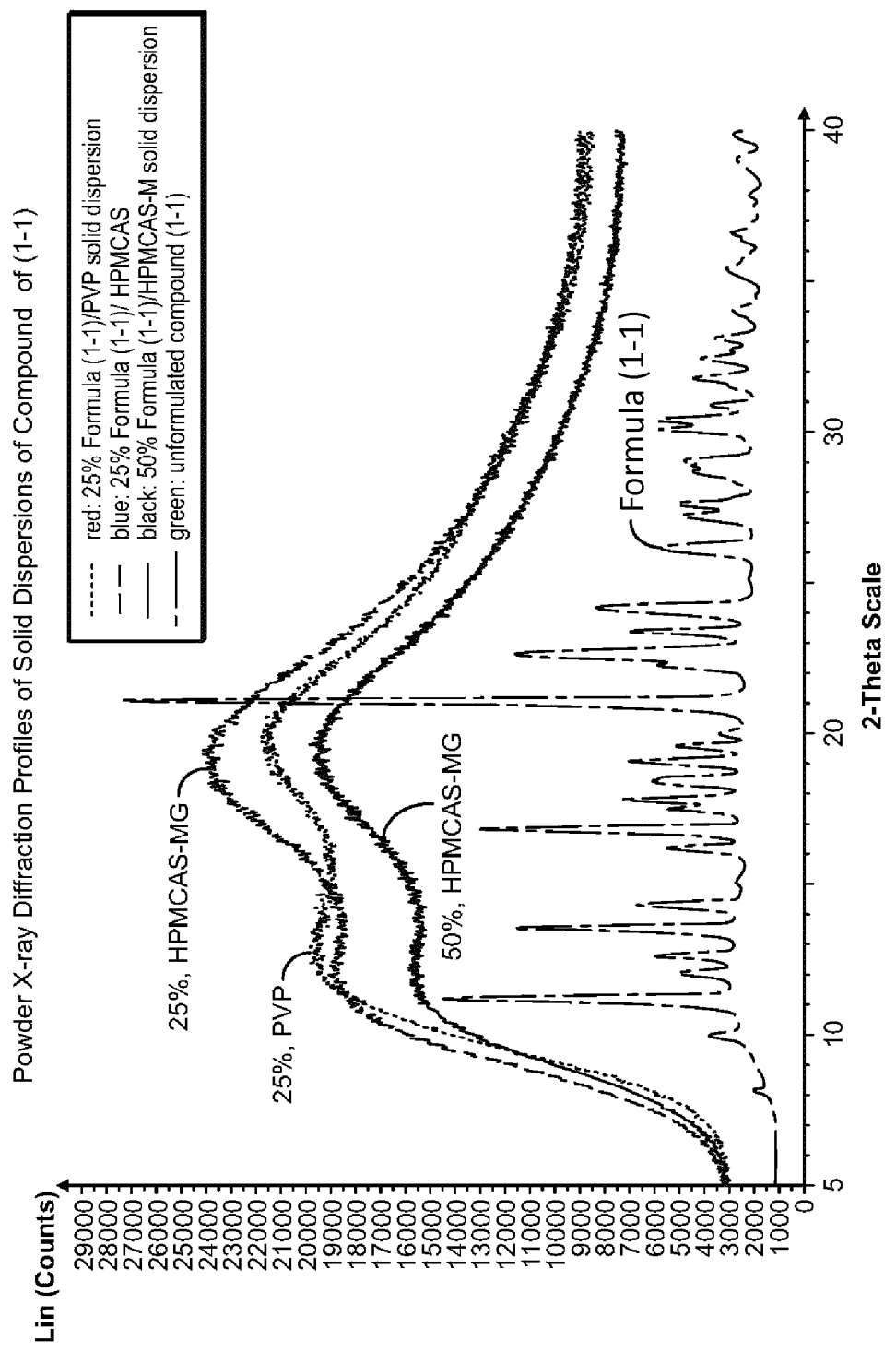
Figure 4A:
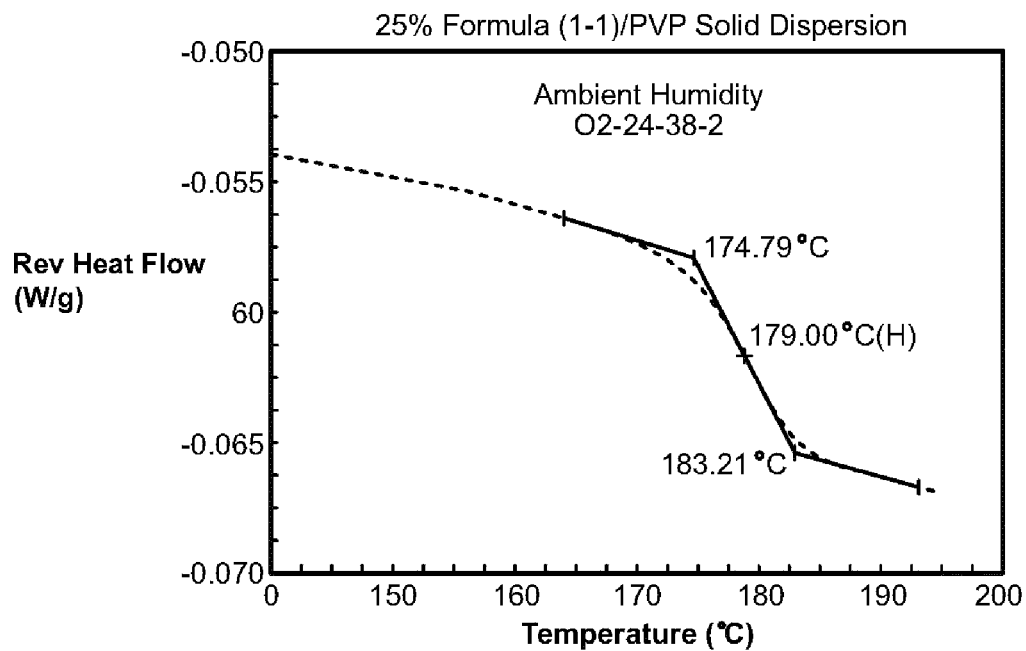
Figure 4B:
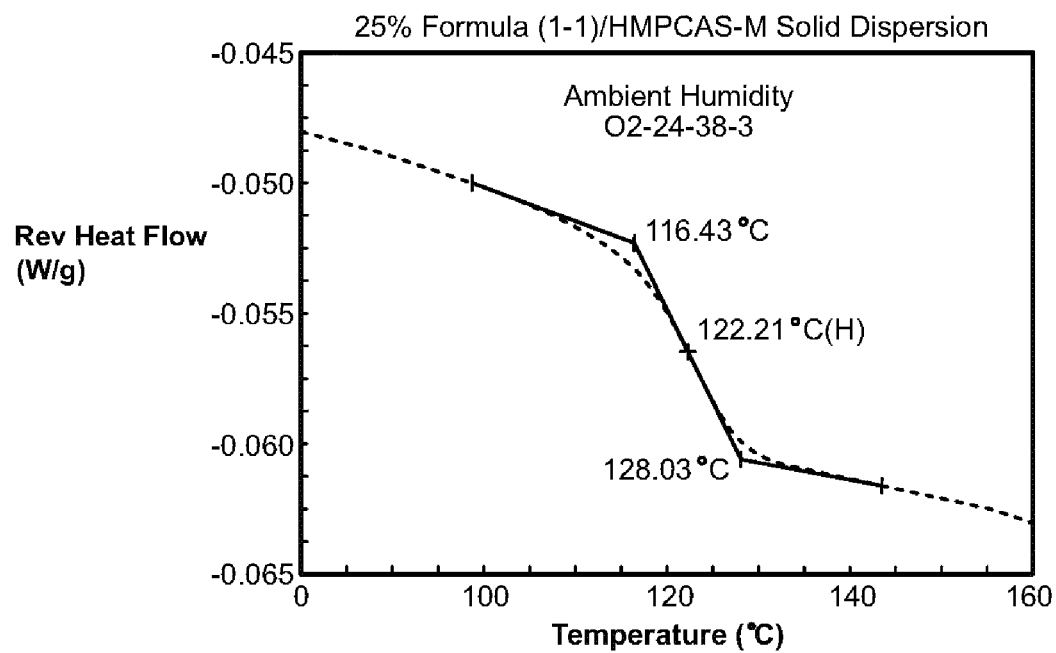
Figure 4C:
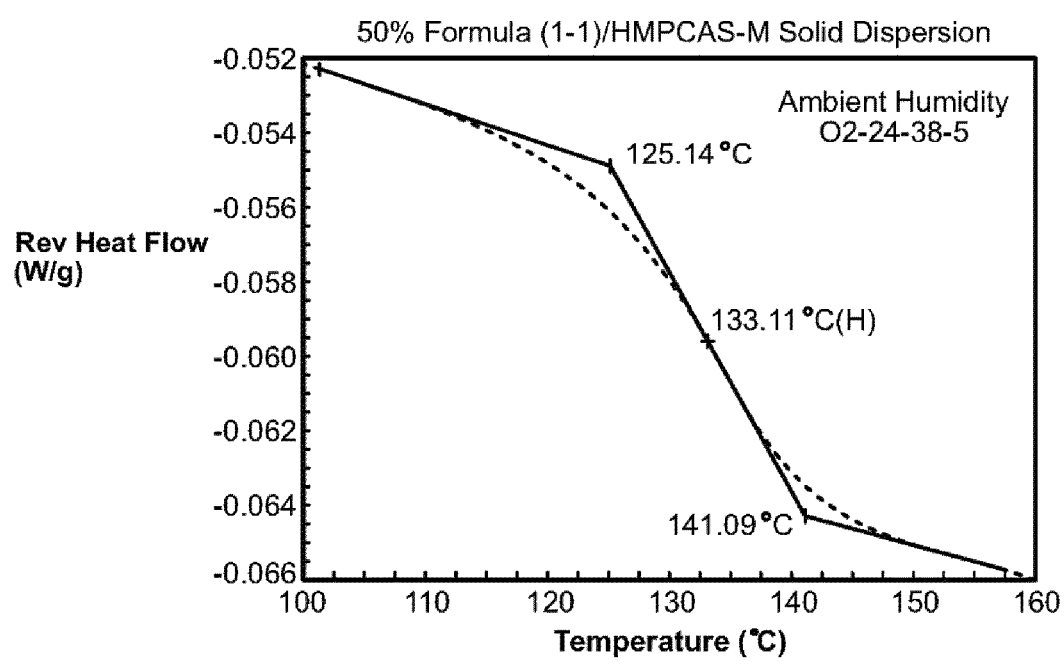
Figure 5:
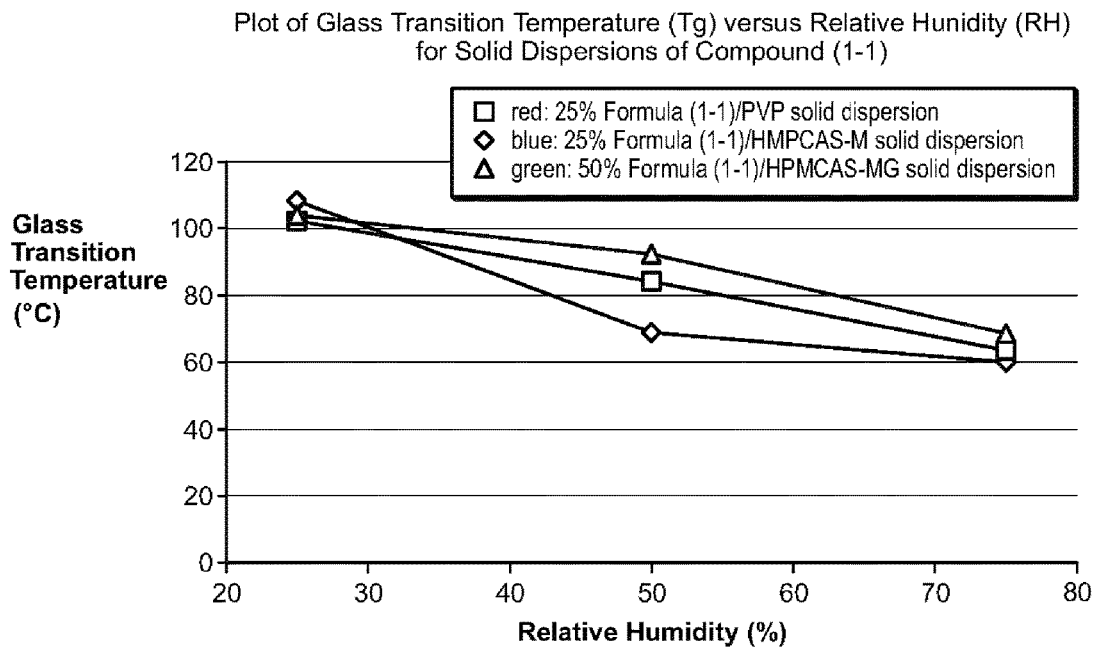
Figure 6:
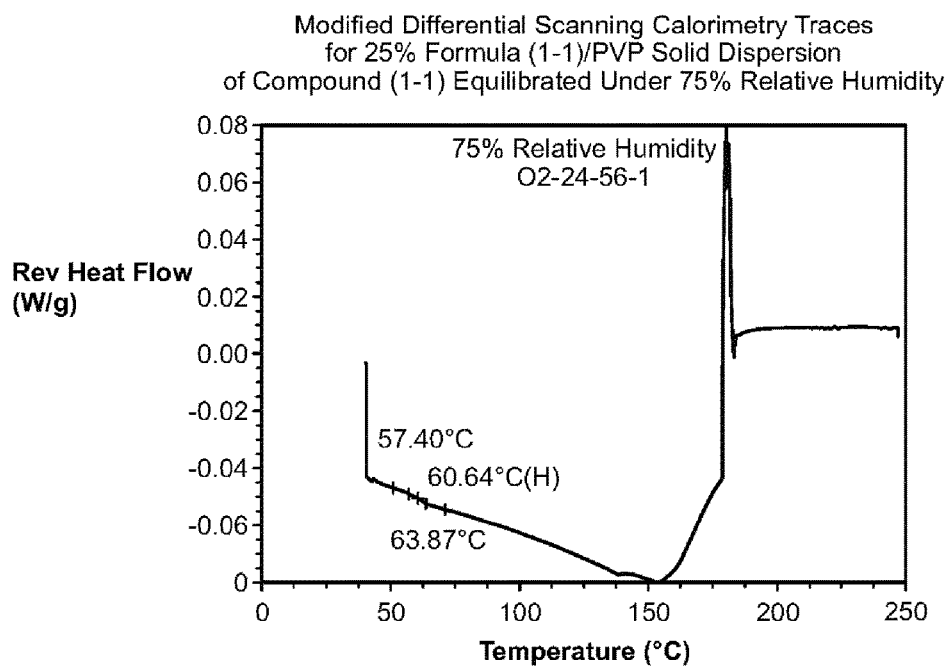
Figure 7:
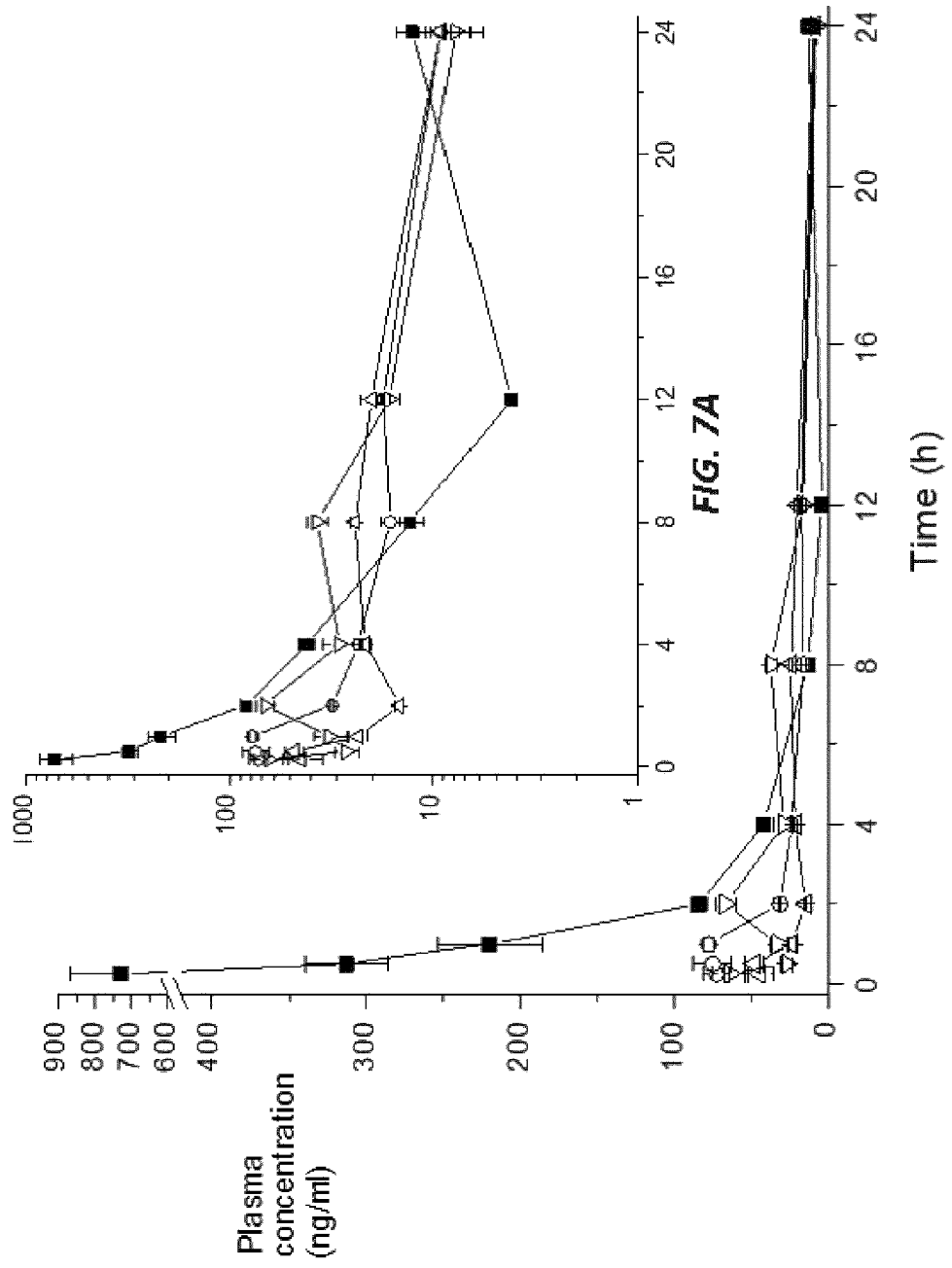
Figure 8:
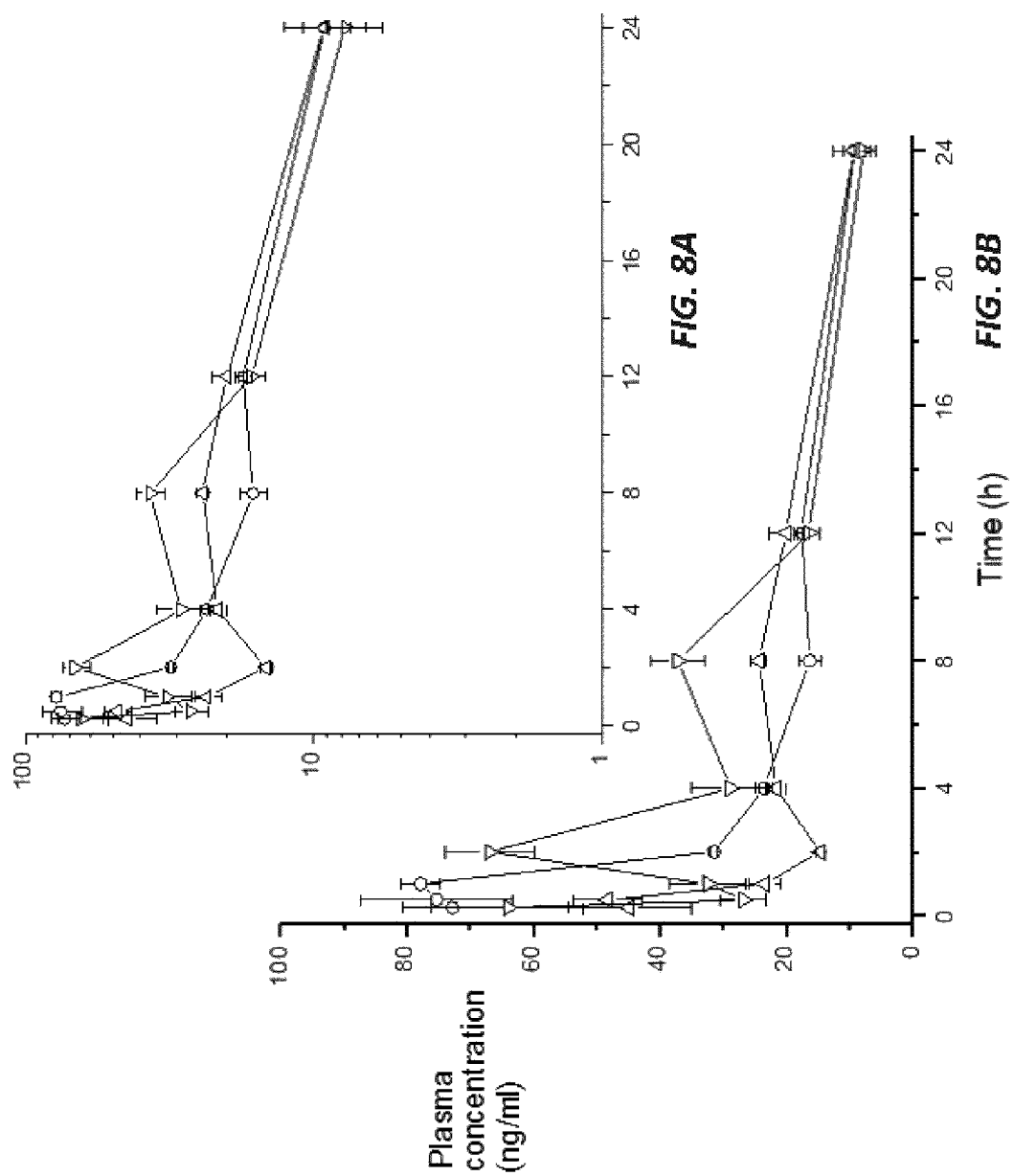
Figure 9:
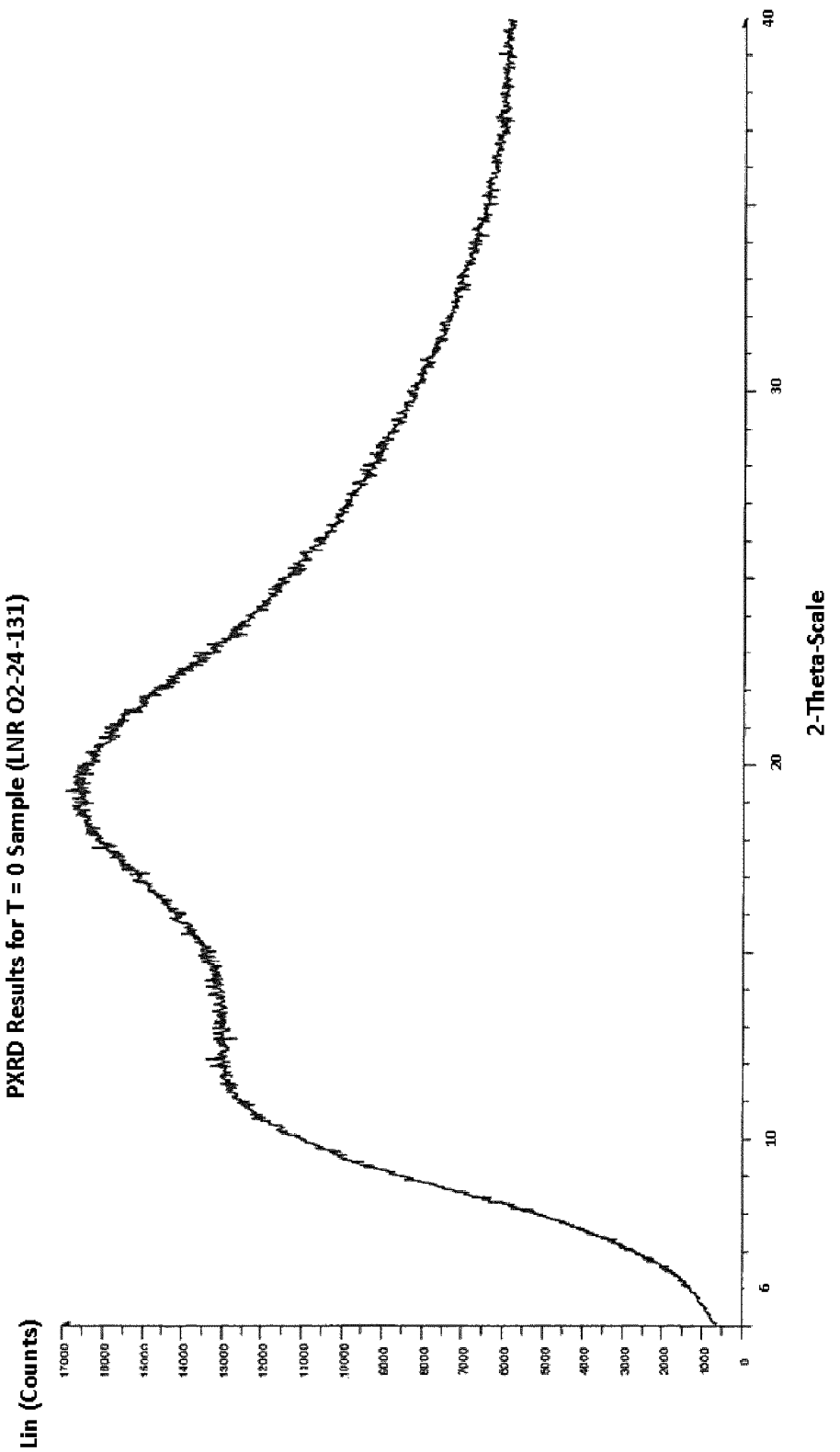
Figure 10:
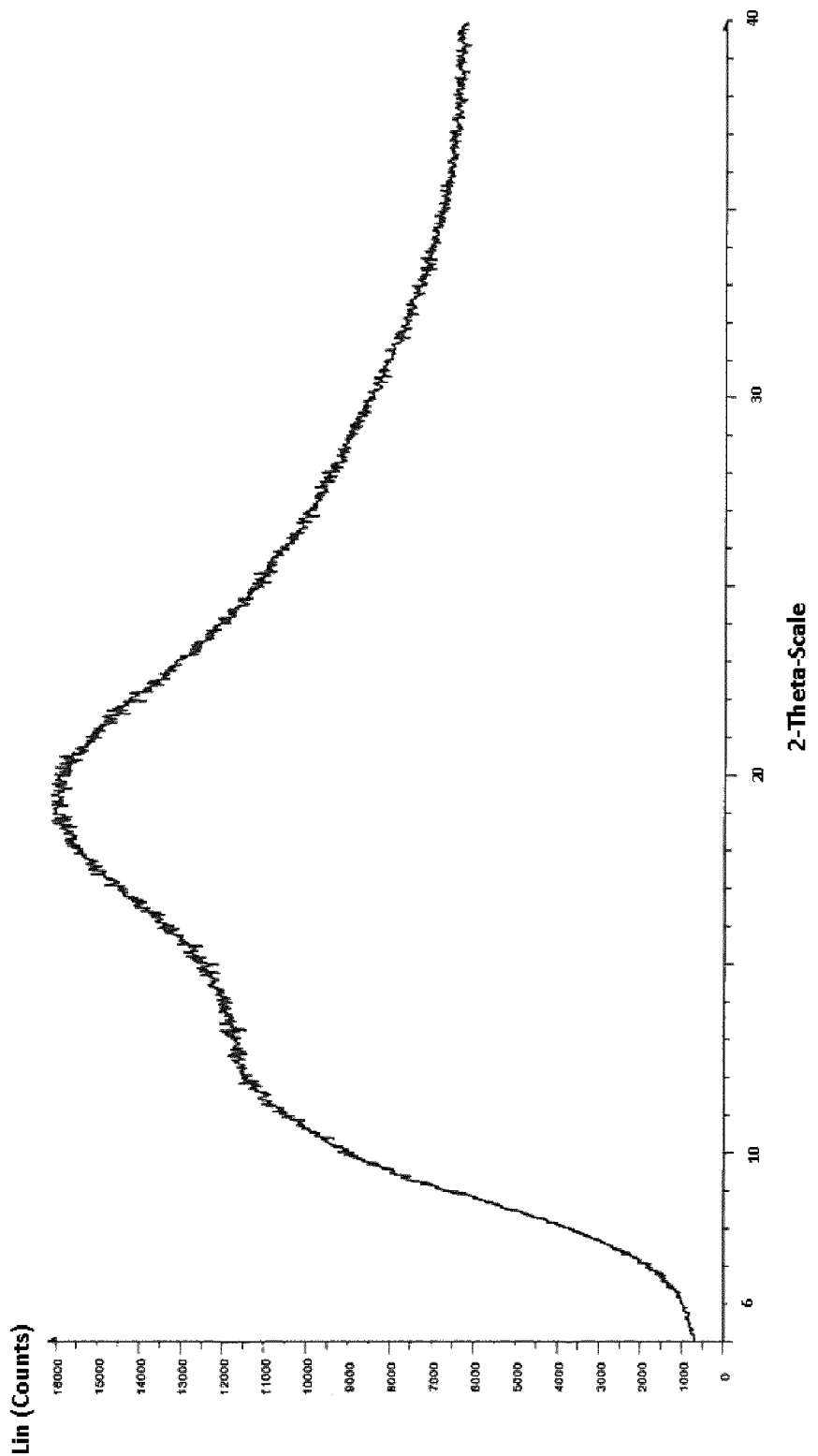
Figure 11:
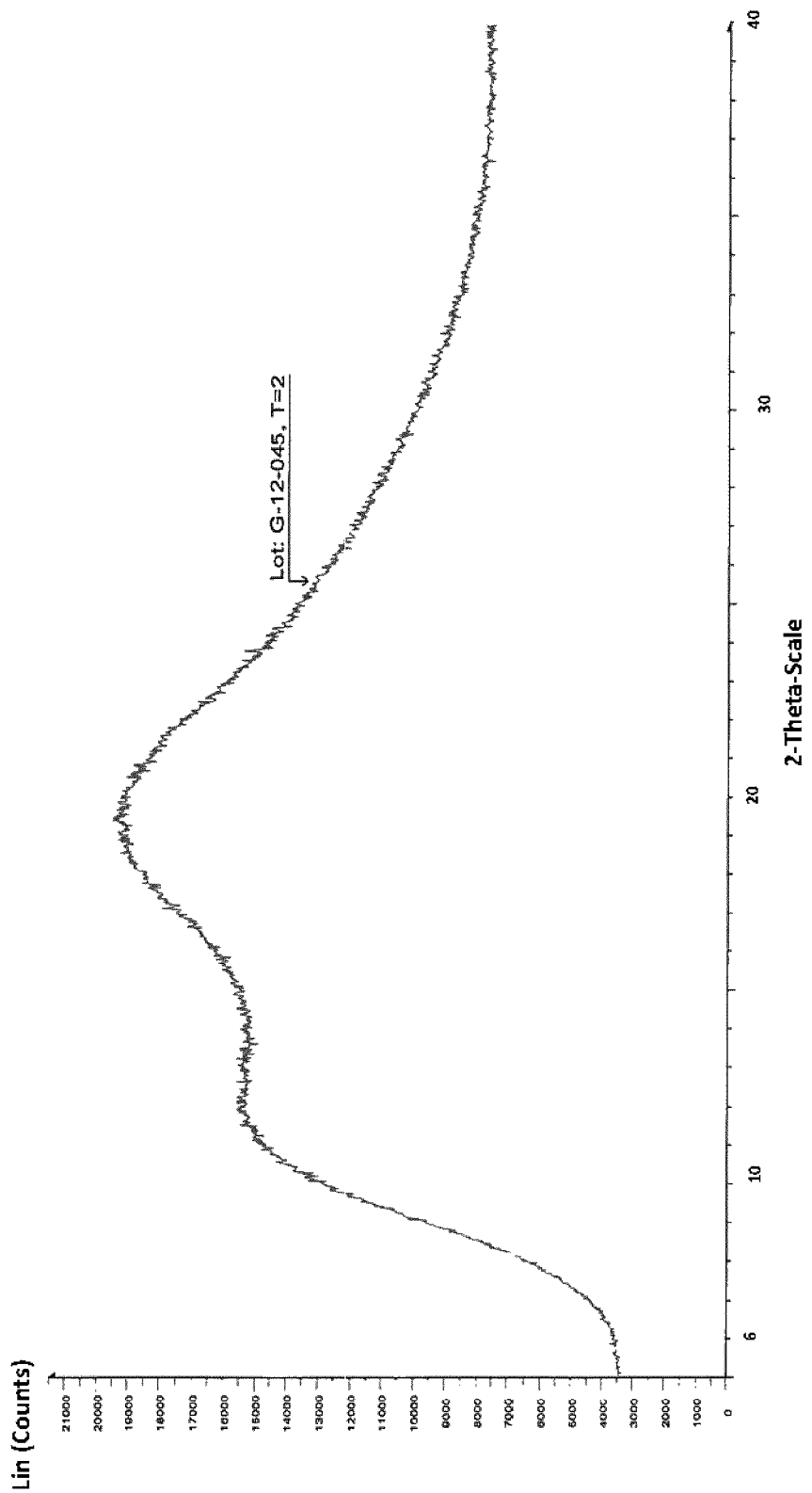
Figure 12:
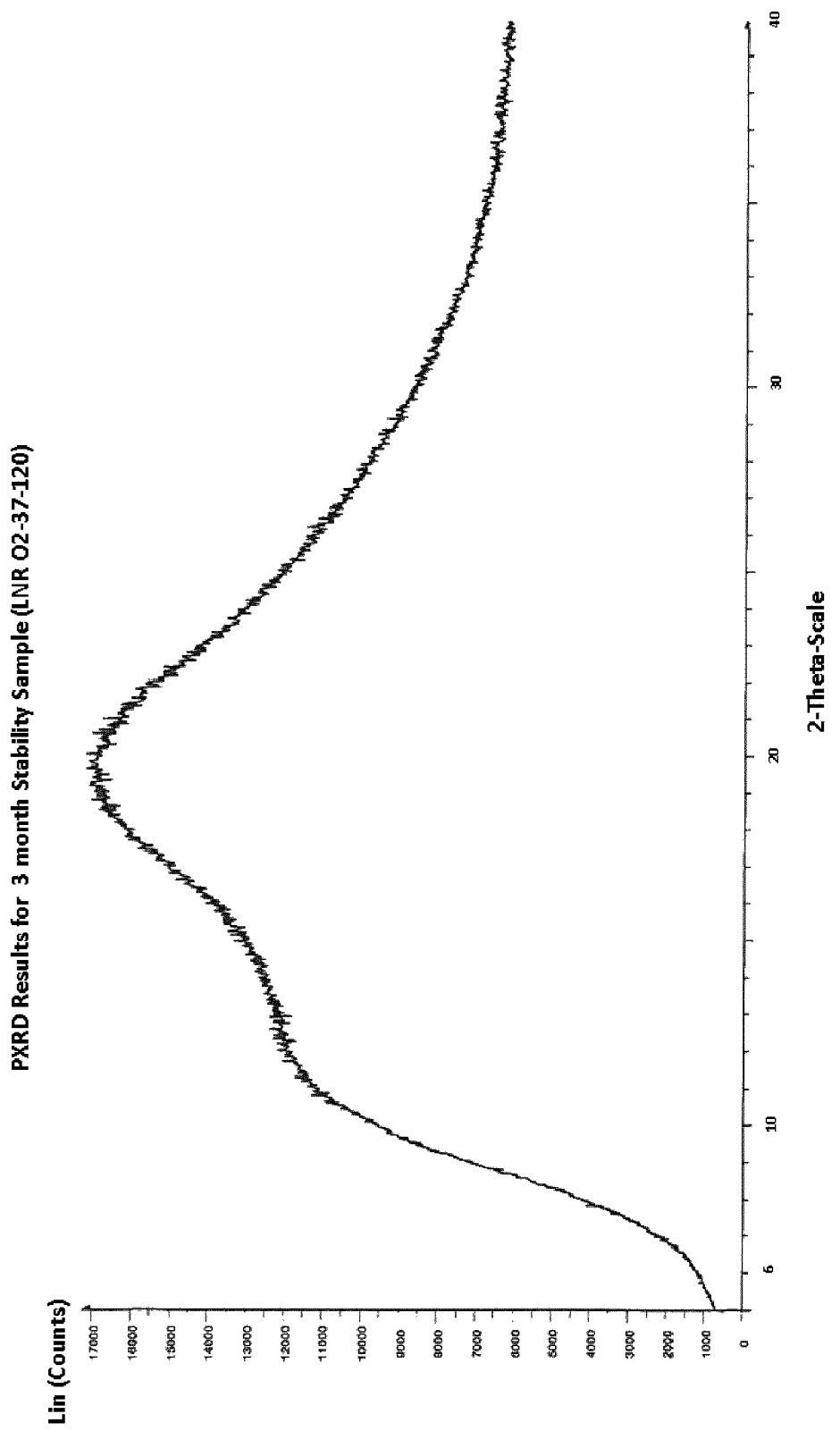
Figure 13B:
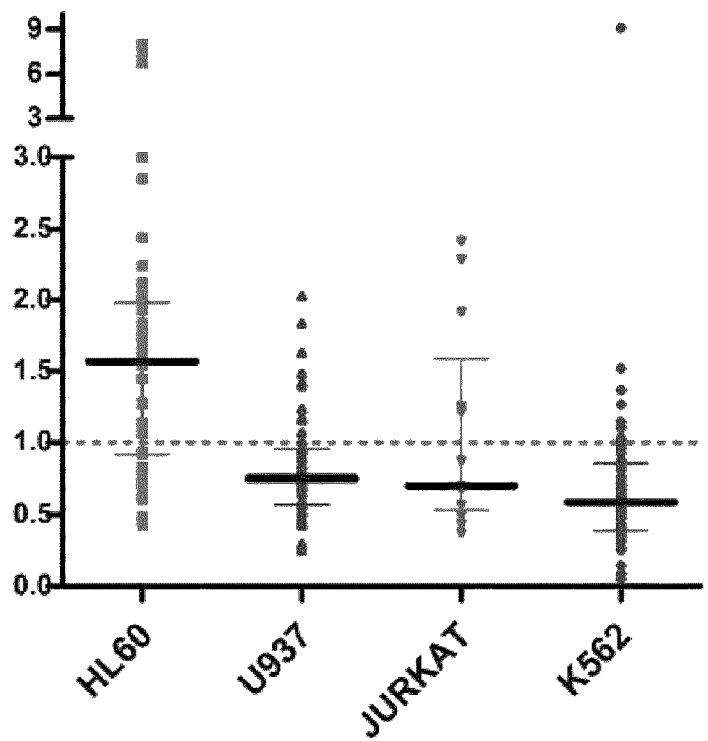
Figure 13C:
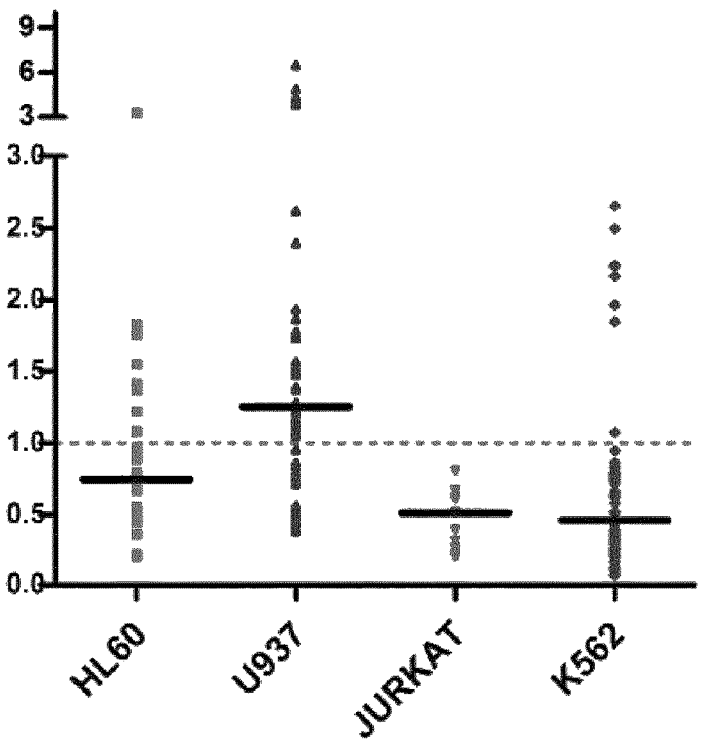
Figure 17C:
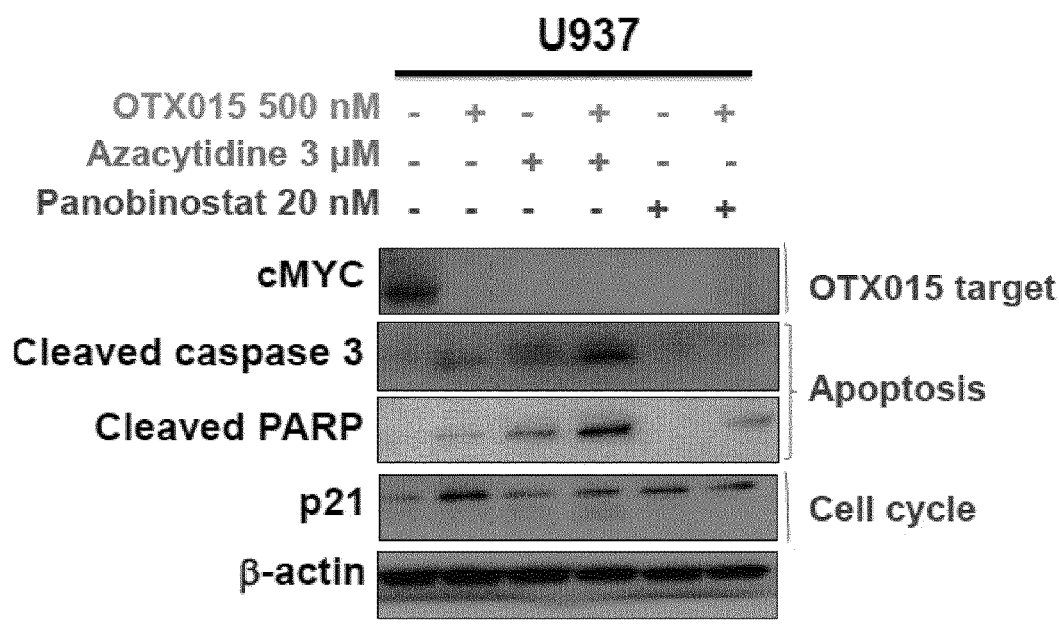
Figure 17D:
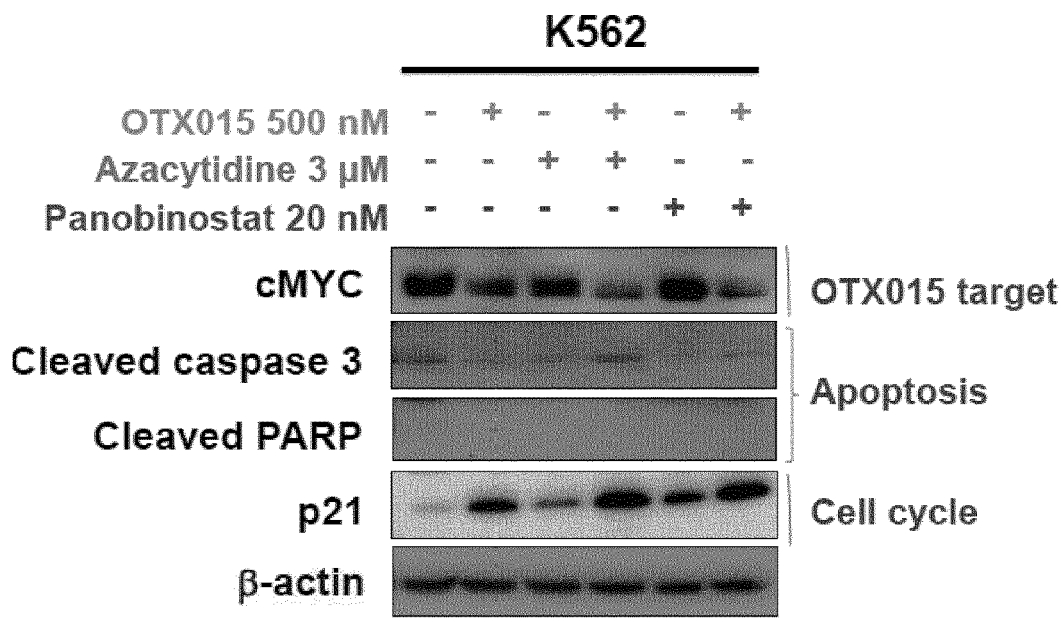

FIG. 2B illustrates results of an in vivo screening of an exemplary formulation comprising a solid dispersion of 25% compound (1-1) and HPMCAS-M;

FIG. 2C illustrates results of an in vivo screening of an exemplary formulation comprising a solid dispersion of 50% compound (1-1) and HPMCAS-M;

FIG. 3 illustrates powder X-ray diffraction profiles of solid dispersions of compound (1-1);

FIG. 4A illustrates modified differential scanning calorimetry trace for a solid dispersion of 25% compound (1-1) and PVP equilibrated under ambient conditions;

FIG. 4B illustrates modified differential scanning calorimetry trace for a solid dispersion of 25% compound (1-1) and HPMCAS-M equilibrated under ambient conditions;

FIG. 4C illustrates modified differential scanning calorimetry trace for a solid dispersion of 50% compound (1-1) and HPMCAS-M equilibrated under ambient conditions;

FIG. 5 illustrates plot of glass transition temperature (Tg) versus relative humidity (RH) for solid dispersions of 25% compound (1-1) and PVP or HMPCAS-M and 50% compound (1-1) and HPMCAS-MG;

FIG. 6 illustrates modified differential scanning calorimetry trace for a solid dispersion of 25% compound (1-1) and PVP equilibrated under 75% relative humidity;

FIG. 7 illustrates plasma concentration versus time curves for Compound (1-1) after 1 mg/kg intravenous dosing (solid rectangles) and 3 mg/kg oral dosing as 25% Compound (1-1):PVP (open circles), 25% Compound (1-1):HPMCAS-MG (open triangles), and 50% Compound (1-1):HPMCAS-MG (open inverted triangles). The inset depicts the same data plotted on a semilogarithmic scale;

FIG. 8 illustrates plasma concentration versus time curves for Compound (1-1) after 3 mg/kg oral dosing as 25% Compound (1-1):PVP (open circles), 25% Compound (1-1):HPMCAS-MG (open triangles), and 50% Compound (1-1): HPMCAS-MG (open inverted triangles). The inset depicts the same data plotted on a semi-logarithmic scale;

FIG. 9 illustrates a powder X-ray diffraction profile of solid dispersions of compound (1-1) in HPMCAS-MG at time zero of a stability test;

FIG. 10 illustrates a powder X-ray diffraction profile of solid dispersions of compound (1-1) in HPMCAS-MG after 1 month at 40° C. and 75% relative humidity;

FIG. 11 illustrates a powder X-ray diffraction profile of solid dispersions of compound (1-1) in HPMCAS-MG after 2 months at 40° C. and 75% relative humidity;

FIG. 12 illustrates a powder X-ray diffraction profile of solid dispersions of compound (1-1) in HPMCAS-MG after 3 month at 40° C. and 75% relative humidity;

FIG. 13A illustrates the 48 hours combination index values for HL60, U937, Jurkat and K562 cell lines treated with a concomitant combination of compound (1-1) and various compounds;

FIG. 13B illustrates the combination index value for HL60, U937, Jurkat and K562 cell lines treated with a concomitant combination of Azacytidine and compound (1-1) for 48 hours;

FIG. 13C illustrates the combination index value for HL60, U937, Jurkat and K562 cell lines treated with a concomitant combination of panobinostat and compound (1-1) for 48 hours;

FIG. 14A illustrates the combination index value for HL60, U937, Jurkat and K562 cell lines treated with a sequential combination of Azacytidine for 48 hours followed by compound (1-1) for 48 hours;

FIG. 14B illustrates the combination index value for HL60, U937, Jurkat and K562 cell lines treated with a sequential combination of Azacytidine for 72 hours followed by compound (1-1) for 48 hours;

FIG. 14B illustrates the combination index value for HL60, U937, Jurkat and K562 cell lines treated with a sequential combination of Azacytidine for 48 hours followed by compound (1-1) for 24 hours;

FIG. 14C illustrates the combination index value for HL60, U937, Jurkat and K562 cell lines treated with a sequential combination of Azacytidine for 72 hours followed by compound (1-1) for 48 hours;

FIG. 14D illustrates a summary of the combination index value for HL60, U937, Jurkat and K562 cell lines treated with a sequential combination of Azacytidine followed by compound (1-1);

FIG. 15A illustrates the combination index value for HL60, U937, Jurkat and K562 cell lines treated with a sequential combination of panobinostat for 48 hours followed by compound (1-1) for 48 hours;

FIG. 15B illustrates the combination index value for HL60, U937, Jurkat and K562 cell lines treated with a sequential combination of panobinostat for 72 hours followed by compound (1-1) for 24 hours;

FIG. 15C illustrates the combination index value for HL60, U937, Jurkat and K562 cell lines treated with a sequential combination of panobinostat for 72 hours followed by compound (1-1) for 48 hours;

FIG. 15D illustrates a summary of the combination index value for HL60, U937, Jurkat and K562 cell lines treated with a sequential combination of panobinostat followed by compound (1-1);

FIG. 16A illustrates the cell percentage of subG1 for HL60 cell line treated with concomitant combination of compound (1-1) and azacytidine or panobinostat for 24 hours;

FIG. 16B illustrates the cell percentage of subG1 for K562 cell line treated with concomitant combination of compound (1-1) and azacytidine or panobinostat for 24 hours;

FIG. 17A illustrates the Western blot profiles of cMYC, cleaved caspase 3, cleaved PARP, p21 and β-actin for HL60 cell line treated with concomitant combination of compound (1-1) and azacytidine or panobinostat for 24 hours;

FIG. 17B illustrates the Western blot profiles of cMYC, cleaved caspase 3, cleaved PARP, p21 and β-actin for Jurkat cell line treated with concomitant combination of compound (1-1) and azacytidine or panobinostat for 24 hours;

FIG. 17C illustrates the Western blot profiles of cMYC, cleaved caspase 3, cleaved PARP, p21 and β-actin for U937 cell line treated with concomitant combination of compound (1-1) and azacytidine or panobinostat for 24 hours; and FIG. 17D illustrates the Western blot profiles of cMYC, cleaved caspase 3, cleaved PARP, p21 and β-actin for K562 cell lines treated with concomitant combination of compound (1-1) and azacytidine or panobinostat for 24 hours.

DETAILED DESCRIPTION OF THE INVENTION

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entireties.

I. DEFINITIONS

The term "alkyl group" as used herein refers to a saturated straight or branched hydrocarbon.

The term "substituted alkyl group" refers to an alkyl moiety having one or more substituents replacing a hydrogen or one or more carbons of the hydrocarbon backbone.

The term "alkenyl group" whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl(2-propenyl), butenyl and the like. Examples include $C_{2-8}$alkenyl or $C_{2-4}$alkenyl groups.

The term "$C_{(j-k)}$" (where j and k are integers referring to a designated number of carbon atoms) refers to an alkyl, alkenyl, alkynyl, alkoxy or cycloalkyl radical or to the alkyl portion of a radical in which alkyl appears as the prefix root containing from j to k carbon atoms inclusive. For example, $C_{(1-4)}$ denotes a radical containing 1, 2, 3 or 4 carbon atoms.

The terms "halo" or "halogen" as used herein refer to F, Cl, Br, or I.

The term "pharmaceutically acceptable salts" is art-recognized and refers to the relatively non-toxic, inorganic and organic acid addition salts, or inorganic or organic base addition salts of compounds, including, for example, those contained in compositions of the present invention.

The term "solid dispersion" as used herein refers to a group of solid products consisting of at least two different components, generally a hydrophilic carrier and a hydrophobic drug (active ingredient).

The term "chiral" is art-recognized and refers to molecules That have the property of non-superimposability of the mirror image partner, while the term "achiral" refers to molecules which are superimposable on their mirror image partner. A "prochiral molecule" is a molecule that has the potential to be converted to a chiral molecule in a particular process.

The symbol "=====" is used to denote a bond that may be a single, a double or a triple bond.

The term "enantiomer" as it used herein, and structural formulas depicting an enantiomer are meant to include the "pure" enantiomer free from its optical isomer as well as mixtures of the enantiomer and its optical isomer in which the enantiomer is present in an enantiomeric excess, e.g., at least 10%, 25%, 50%, 75%, 90%, 95%, 98%, or 99% enantiomeric excess.

The term "stereoisomers" when used herein consist of all geometric isomers, enantiomers or diastereomers. The present invention encompasses various stereoisomers of these compounds and mixtures thereof. Conformational isomers and rotamers of disclosed compounds are also contemplated.

The term "stereoselective synthesis" as it is used herein denotes a chemical or enzymatic reaction in which a single reactant forms an unequal mixture of stereoisomers during the creation of a new stereocenter or during the transformation of a pre-existing one, and are well known in the art. Stereoselective syntheses encompass both enantio selective and diastereoselective transformations. For examples, see Carreira, E. M. and Kvaerno, L., *Classics in Stereoselective Synthesis*, Wiley-VCH: Weinheim, 2009.

The term "spray drying" refers to processes which involve the atomization of the feed suspension or solution into small droplets and rapidly removing solvent from the mixture in a processor chamber where there is a strong driving force for the evaporation (e.g., hot dry gas or partial vacuum or combinations thereof).

The term "therapeutically effective amount" as used herein refers to any amount of a thienotriazolodiazepine of the present invention or any other pharmaceutically active agent which, as compared to a corresponding a patient who has not received such an amount of the thienotriazolodiazepine or the other pharmaceutically active agent, results in improved treatment, healing, prevention, or amelioration of a disease, disorder, or side effect, or a decrease in the rate of advancement of a disease or disorder.

The term "about" means+/−10%.

Throughout this application and in the claims that follow, unless the context requires otherwise, the word "comprise", or variations such as "comprises" or "comprising", should be understood to imply the inclusion of a stated integer step or group of integers or steps but not the exclusion of any other integer or step or group of integers or steps.

It has now been found that thienotriazolodiazepine compound of Formula (1), described herein below, can be formulated as a solid dispersion with pharmaceutically acceptable polymers, to provide an oral formulation that provides high absorption of the pharmaceutical ingredient into the circulation from the gastrointestinal tract. In one embodiment, the pharmaceutically acceptable polymer is hypromellose acetate succinate (also called hydroxypropylmethylcellulose acetate succinate or HPMCAS). In one embodiment, the pharmaceutically acceptable polymer is polyvinylpyrrolidone (PVP).

In some embodiments, the hydroxypropylmethyl cellulose acetate succinates (HPMCAS), may include M grade having 9% acetyl/11% succinoyl (e.g., HPMCAS having a mean particle size of 5 µm (i.e., HPMCAS-MF, fine powder grade) or having a mean particle size of 1 mm (i.e., HPMCAS-MG, granular grade)), H grade having 12% acetyl/6% succinoyl (e.g., HPMCAS having a mean particle size of 5 µm (i.e., HPMCAS-HF, fine powder grade) or having a mean particle size of 1 mm (i.e., HPMCAS-HG, granular grade)), and L grade having 8% acetyl/15% succinoyl (e.g., HPMCAS having a mean particle size of 5 µm (i.e., HPMCAS-LF, fine powder grade) or having a mean particle size of 1 mm (i.e., HPMCAS-LG, granular grade).

In some embodiments, the polyvinyl pyrrolidones may have molecular weights of about 2,500 (Kollidon®12 PF, weight-average molecular weight between 2,000 to 3,000), about 9,000 (Kollidon® 17 PF, weight-average molecular weight between 7,000 to 11,000), about 25,000 (Kollidon® 25, weight-average molecular weight between 28,000 to 34,000), about 50,000 (Kollidon® 30, weight-average molecular weight between 44,000 to 54,000), and about 1,250,000 (Kollidon® 90 or Kollidon® 90F, weight-average molecular weight between 1,000,000 to 1,500,000).

II. METHODS OF TREATMENT

In one embodiment, the present disclosure provides for a method of treating leukemia in a mammal, comprising administering to a patient in need of such treatment a pharmaceutically acceptable amount of a composition comprising a solid dispersion according to the compositions described in sections III, IV, V, VI and VII.

In one embodiment, the leukemia is selected from the group consisting of acute lymphoblastic leukemia (ALL), acute myelogenous leukemia (AML) (or myeloblastic), chronic lymphocytic leukemia (CLL), and chronic myelogenous leukemia (CML).

In one embodiment, a method of treating leukemia in accordance with the present invention comprises administering an effective amount of a compound according to Formula (1) or a pharmaceutically acceptable salt thereof to a patient in need of such treatment in combination with at least one other therapeutic agent, wherein the compound of Formula (1) or the pharmaceutically acceptable salt thereof and the at least one other therapeutic agent are administered either simultaneously or sequentially. In one embodiment, the compound according to Formula (1) and the other therapeutic agent can be administered simultaneously or sequentially. In some embodiments the combination produces a synergistic effect. In one embodiment, the other therapeutic agent is independently selected from the group consisting of an epigenetic modulator, a glucocorticoid, an m-TOR inhibitor, an HDAC-inhibitor, a demethylating agent, anthracycline, an analogue of cytidine and a cytotoxic drug. In one such embodiment, the demethylating agent is decitabine. In another such embodiment, the HDAC-inhibitor is vorinostat or panobinostat. In another such embodiment, the mTOR inhibitor is everolimus. In another such embodiment, the glucocorticoid is dexamethasone. In another such embodiment, the cytotoxic drug is selected from the group consisting of cytarabine or methotrexate. In another such embodiment, the analogue of cytidine is azacytidine. In another such embodiment, the anthracycline is daunorubicin.

In some embodiments, the present disclosure provides for methods of treating acute myeloid leukemia in a mammal comprising: administering to a patient in need a pharmaceutically acceptable amount of a composition comprising a solid dispersion according to any of the compositions described in Sections III, IV, V and VI described herein.

Acute myeloid leukemia includes cancer of the blood and bone marrow, in which the bone marrow makes abnormal myeloblasts, red blood cells, or platelets. Acute myeloid leukemia, includes but is not limited to, subclasses of acute myeloid leukemia as classified by the World Health Organization as well as subclasses of acute myeloid leukemia as classified by the French-American-British (FAB) cooperative group. In some embodiments acute myeloid leukemia can be mixed lineage leukemia (MLL) fusion positive, post-JAK2 mutated polycythemia vera, or post-myelodysplastic syndrome. In some embodiments acute myeloid leukemia can be acute basophilic leukemia, acute panmyelosis with myelofibrosis, or myeloid sarcoma. In some embodiments acute myeloid leukemia is acute myeloblastic leukemia (minimally differentiated), acute myeloblastic leukemia (without maturation), acute myeloblastic leukemia (with granulocytic maturation), acute promyelocytic leukemia, acute myelomonocytic leukemia, myelomonocytic together with bone marrow eosinophilia, acute monoblastic leukemia, acute monocytic leukemia, acute erythroid leukemia, or acute megakaryoblastic leukemia. In some embodiments, acute myeloid leukemia is acute myeloid leukemia with recurrent genetic abnormalities, acute myeloid leukemia with multilineage displasia, or therapy-related acute myeloid leukemia. AML with recurrent genetic abnormalities includes, but is not limited to, AML with t(8; 21)(q22; q22), AML with inv(16)(p13q22) or t(16; 16)(p13; q22), AML with t(15; 17)(q22; q12), and AML with 11q23 abnormalities. Therapy related AML includes, but is not limited to, alkylating agent-related AML and topoisomerase II inhibitor-related AML.

In one embodiment, a method of treating acute myeloid leukemia in accordance with the present invention comprises administering an effective amount of a compound according to Formula (1) or a pharmaceutically acceptable salt thereof to a patient in need of such treatment in combination with at least one other therapeutic agent, wherein the compound of Formula (1) or the pharmaceutically acceptable salt thereof and the at least one other therapeutic agent are administered either simultaneously or sequentially. In one embodiment, the compound according to Formula (1) and the other therapeutic agent can be administered simultaneously or sequentially. In some embodiments the combination produces a synergistic effect. In one embodiment, the other therapeutic agent is independently selected from the group consisting of an epigenetic modulator, a glucocorticoid, an m-TOR inhibitor, an HDAC-inhibitor, a demethylating agent, anthracycline, an analogue of cytidine and a cytotoxic drug. In one such embodiment, the demethylating agent is decitabine. In another such embodiment, the HDAC-inhibitor is vorinostat or panobinostat. In another such embodiment, the mTOR inhibitor is everolimus. In another such embodiment, the glucocorticoid is dexamethasone. In another such embodiment, the cytotoxic drug is selected from the group consisting of cytarabine or methotrexate. In another such embodiment, the analogue of cytidine is azacytidine. In another such embodiment, the anthracycline is daunorubicin.

In some embodiments, the present disclosure provides for methods of treating chronic acute myeloid leukemia in a mammal comprising: administering to a patient in need a pharmaceutically acceptable amount of a composition comprising a solid dispersion according to any of the compositions described in Sections III, IV, V and VI described herein. In some embodiments the chronic acute myeloid leukemia can be in a chronic phase. In other embodiments the chronic acute myeloid leukemia can be in an accelerated phase. In still other embodiments the chronic acute myeloid leukemia can be in a blast crisis phase.

In one embodiment, a method of treating chronic acute myeloid leukemia in accordance with the present invention comprises administering an effective amount of a compound according to Formula (1) or a pharmaceutically acceptable salt thereof to a patient in need of such treatment in combination with at least one other therapeutic agent, wherein the compound of Formula (1) or the pharmaceutically acceptable salt thereof and the at least one other therapeutic agent are administered either simultaneously or sequentially. In one embodiment, the compound according to Formula (1) and the other therapeutic agent can be administered simultaneously or sequentially. In some embodiments the combination produces a synergistic effect. In one embodiment, the other therapeutic agent is independently selected from the group consisting of an epigenetic modulator, a glucocorticoid, an m-TOR inhibitor, an HDAC-inhibitor, a demethylating agent, anthracycline, an analogue of cytidine and a cytotoxic drug. In one such embodiment, the demethylating agent is decitabine. In another such embodiment, the HDAC-inhibitor is vorinostat or panobinostat. In another such embodiment, the mTOR inhibitor is everolimus. In another such embodiment, the glucocorticoid is dexamethasone. In another such embodiment, the cytotoxic drug is selected from the group consisting of cytarabine or methotrexate. In another such embodiment, the analogue of cytidine is azacytidine. In another such embodiment, the anthracycline is daunorubicin.

In some embodiments, the present disclosure provides for methods of treating acute lymphoblastic leukemia in a mammal comprising: administering to a patient in need a pharmaceutically acceptable amount of a composition comprising a solid dispersion according to any of the compositions described in Sections III, IV, V and VI described herein. In some embodiments the acute lymphoblastic leukemia can be classified as ALL-L1. In other embodiments the acute lymphoblastic leukemia can be classified as ALL-L2. In still other embodiments the acute lymphoblastic leukemia can be classified as ALL-L3. In some embodiments the acute lymphoblastic leukemia can be classified as precursor B acute lymphoblastic leukemia or pre-B cell. In other embodiments the acute lymphoblastic leukemia can be classified as precursor T acute lymphoblastic leukemia or pre-T cell. In some embodiments precursor B acute lymphoblastic leukemia can have the cytogenetic subtype t(12; 21)(p12,q22) TEL/AML-1; t(1;19)(q23;p13) PBX/E2A; t(9; 22)(q34;q11) ABL/BCR; or T(V,11)(V;q23) V/MLL. In some embodiments the acute lymphoblastic leukemia is Burkitt's leukemia. In some embodiments the acute lymphoblastic leukemia is Biphenotypic acute leukemia.

In one embodiment, a method of treating acute lymphoblastic leukemia in accordance with the present invention comprises administering an effective amount of a compound according to Formula (1) or a pharmaceutically acceptable salt thereof to a patient in need of such treatment in combination with at least one other therapeutic agent, wherein the compound of Formula (1) or the pharmaceutically acceptable salt thereof and the at least one other therapeutic agent are administered either simultaneously or sequentially. In one embodiment, the compound according to Formula (1) and the other therapeutic agent can be administered simultaneously or sequentially. In some embodiments the combination produces a synergistic effect. In one embodiment, the other therapeutic agent is independently selected from the group consisting of an epigenetic modulator, a glucocorticoid, an m-TOR inhibitor, an HDAC-inhibitor, a demethylating agent, anthracycline, an analogue of cytidine and a cytotoxic drug. In one such embodiment, the demethylating agent is decitabine. In another such embodiment, the HDAC-inhibitor is vorinostat or panobinostat. In another such embodiment, the mTOR inhibitor is everolimus. In another such embodiment, the glucocorticoid is dexamethasone. In another such embodiment, the cytotoxic drug is selected from the group consisting of cytarabine or methotrexate. In another such embodiment, the analogue of cytidine is azacytidine. In another such embodiment, the anthracycline is daunorubicin.

In some embodiments, methods of treating acute myeloid leukemia, chronic acute myeloid leukemia, or acute lymphoblastic leukemia use thienotriazolodiazepine compound of the Formula (1)

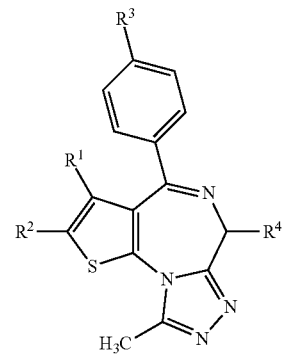

wherein $R^1$ is alkyl having a carbon number of 1-4, $R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, including any salts, isomers, enantiomers, racemates, hydrates, solvates, metabolites, and polymorphs thereof.

In some embodiments, Formula (1) is selected from Formula (1A):

Formula (1A)

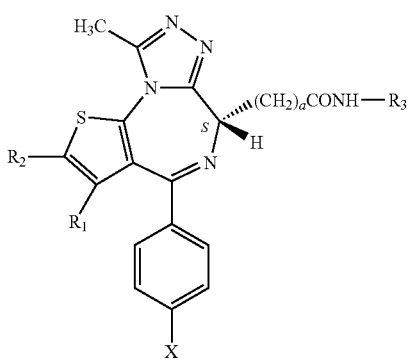

wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s), or heteroaryl optionally having substituent(s), a pharmaceutically acceptable salt thereof or a hydrate thereof; and a pharmaceutically acceptable polymer. In one such embodiment, the thienotriazolodiazepine compound is formulated as a solid dispersion comprising an amorphous thienotriazolodiazepine compound.

In the present invention, "treatment" or "treat" refers to an act or the action of administration of the active ingredient of the present invention to a person diagnosed by a doctor to have AML, CML, or ALL or be at risk of developing AML, CML, or ALL (patient), which aims, for example, to alleviate the AML, CML, or ALL or symptom, prevent the onset of the AML, CML, or ALL, or symptom, or restore the state before onset of the AML, CML, or ALL.

Example demethylating agents for use in combinations with the thienotriazolodiazepine compounds of Formula (1) in the methods of the present invention include the compounds listed in the below Table A.

TABLE A

| Inhibitor Name | Inhibitor Information | Literature Citations |
|---|---|---|
| decitabine (5-aza-2'-deoxycytidine) | [structure] | J Natl Cancer Inst 2005; 97:1498-1506 |
| 5-azacytidine | [structure] | Experientia 1964; 20:202-3; Cell 1980; 20:85-93; J Natl Cancer Inst 2005; 97:1498-1506 |
| zebularin | [structure] | J Natl Cancer Inst 2005; 97:1498-1506 |
| RG108 | [structure] | J Natl Cancer Inst 2005; 97:1498-1506 |

TABLE A-continued

| Inhibitor Name | Inhibitor Information | Literature Citations |
| --- | --- | --- |
| epigallocatechin-3-gallate (EGCG) 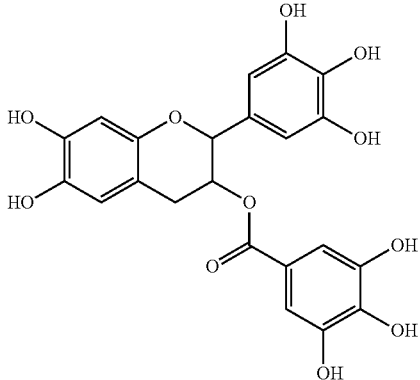 [SMILES: O=C(OC1Cc2cc(O)c(O)cc2OC1c1cc(O)c(O)c(O)c1)c1cc(O)c(O)c(O)c1] | | J Natl Cancer Inst 2005; 97:1498-1506 |
| procaine 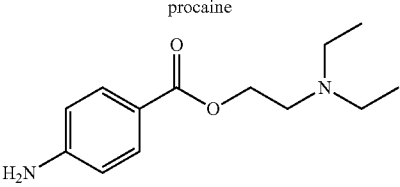 | | J Natl Cancer Inst 2005; 97:1498-1506 |

Example histone deacetylase (HDAC) inhibitors for use in combinations with the thienotriazolodiazepine of Formula (1) in the methods of the present invention include, but are not limited to, the HDAC inhibitors listed in the below Table B.

TABLE B

| Inhibitor Name | Inhibitor Information | Literature Citations |
| --- | --- | --- |
| Vorinostat (SAHA, MK0683) | Vorinostat (suberoylanilide hydroxamic acid, SAHA, Zolinza) is an HDAC inhibitor with IC50 of ~10 nM. | Nature, 2011, 471(7337):235-9; Nat Biotechnol, 2011, 29(3), 255-265; J Exp Med, 2012, 209(1):35-50. |
| Entinostat (MS-275,SNDX-275) | MS-275 is an HDAC inhibitor of HDAC1 and HDAC3 with IC50 of 0.51 µM and 1.7 µM, respectively. | Nat Biotechnol, 2011, 29(3), 255-265; Proc Natl Acad Sci USA, 2011, 108(49): 19629-34; Circ Res, 2012, 110(5):739-48. |
| Panobinostat (LBH589, NVP-LBH589) | LBH589 (Panobinostat) is a novel broad-spectrum HDAC inhibitor with IC50 of 5 nM and 20 nM in MOLT-4 and Reh cells, respectively. | Nat Biotechnol, 2011,29(3), 255-265; Blood, 2012, 119(6): 1450-8; Acta Neuropathol, 2011, 122(5):637-50 |

TABLE B-continued

| Inhibitor Name | Inhibitor Information | Literature Citations |
| --- | --- | --- |
| Trichostatin A (TSA) | Trichostatin A (TSA) is an HDAC inhibitor with IC50 of ~1.8 nM. | Plant J, 2013, 74(5), 815-828; Epigenetics, 2012, 7(10), 1161-1172. |
| Mocetinostat (MGCD0103, MG0103) 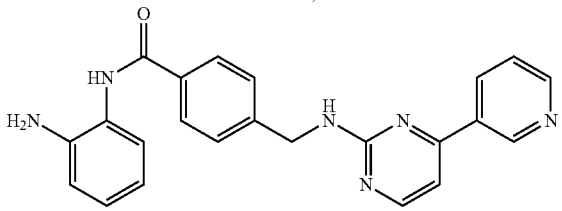 [SMILES: Nc1ccccc1NC(=O)c1ccc(CNc2nccc(-c3cccnc3)n2)cc1] | MGCD0103 (Mocetinostat) is a potent HDAC inhibitor for HDAC1, HDAC2 and HDAC3 with IC50 of 0.15 µM, 0.29 µM and 1.66 µM, respectively. | Nat Struct Mol Biol, 2013, 20(3):317-25; Circ Res, 2012, 110(5):739-48; Oncogene, 2011, 30(27), 3062-3072. |
| Belinostat (PXD101) | Belinostat (PXD101) is a novel HDAC inhibitor with IC50 of 27 nM in HeLa cell extracts. | Nat Biotechnol, 2011, 29(3), 255-265; Breast Cancer Res Treat, 2011, 131(3), 777-789; PLoS One, 2011, 6(2), e17138. |
| MC1568 | MC1568 is a selective HDAC inhibitor with IC50 of 220 nM. | Proc Natl Acad Sci USA, 2012, 109(34):E2284-93; Oncogene, 2013,; J Biol Chem, 2011, 286(27), 23842-23851. |
| LAQ824 (NVP-LAQ824, Dacinostat) 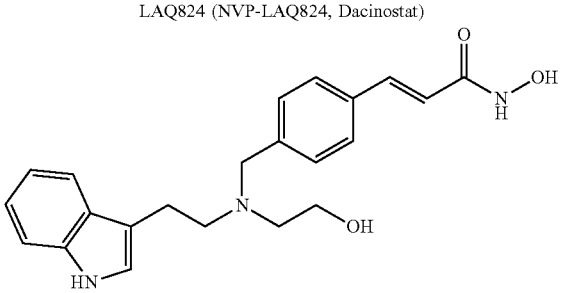 | LAQ824 (NVP-LAQ824) is a novel HDAC inhibitor with IC50 of 32 nM. | Nat Biotechnol, 2011, 29(3), 255-265; Diabetologia, 2012, 55(9):2421-31; Mol Pain, 2010, 6, 51. |
| ITF2357 (Givinostat) | ITF2357 (Givinostat) is a potent inhibitor of HDAC with IC50 of 7.5-16 nM. | J Neurosci, 2013, 33(17), 7535-7547. |
| Tubastatin A HCl 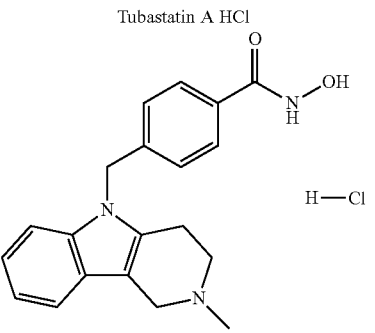 | Tubastatin A is a potent HDAC6 inhibitor with IC50 of 15 nM. | |
| CUDC-101 | CUDC-101 is a potent multi-target | |

TABLE B-continued

| Inhibitor Name | Inhibitor Information | Literature Citations |
|---|---|---|
| 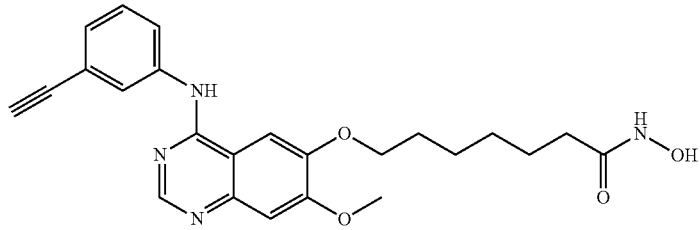 [SMILES: C#Cc1cccc(Nc2ncnc3cc(OC)c(OCCCCCCC(=O)NO)cc23)c1] | inhibitor targeting HDAC, EGFR and HER2 with IC50 of 4.4 nM, 2.4 nM, and 15.7 nM, respectively. | |
| SB939 (Pracinostat)<br>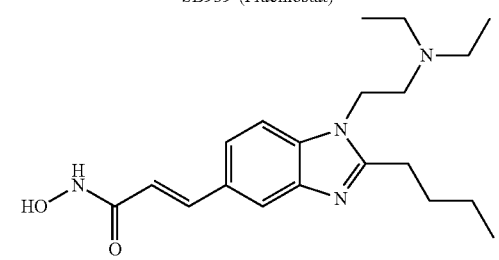<br>(E)-3-(2-butyl-1-(2-(diethylamino)ethyl)-1H-benzo[d]imidazol-5-yl)-N-hydioxyacrylamide | SB939 is a potent HDAC inhibitor with IC50 of 40-140 nM. | Antimicrob Agents Chemother, 2012, 56(7), 3849-3856 |
| Droxinostat<br>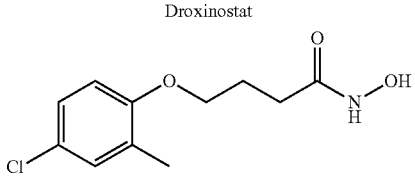<br>4-(4-Chloro-2-methylphenoxy)-N-hydroxybutanamide | Droxinostat (CMH, 5809354) is a selective inhibitor of HDAC3, HDAC6 and HDACK with IC50 of 16.9 μM, 2.47 μM and 1.46 nM, respectively. | Nat Struct Mol Biol, 2013, 2(3):317-25 |
| JNJ-26481585 (Quisinostat)<br>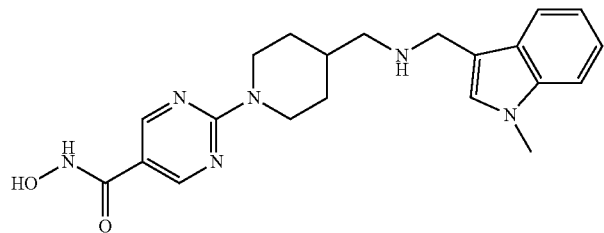 [SMILES: Cn1cc(CNCC2CCN(c3ncc(C(=O)NO)cn3)CC2)c2ccccc21]<br>N-hydroxy-2-(4-((((1-methyl-1H-indol-3-yl)methyl)amino)methyl)piperidin-1-yl)pyrimidine-5-carboxamide | JNJ-26481585 (Quisinostat) is an HDAC inhibitor for HDAC1, HDAC2, HDAC4, HDAC10 and HDAC11 with IC50 of 0.11 nM, 0.33 nM, 0.64 nM, 0.46 nM and 0.37 nM, respectively. | |
| PCI-24781(CRA-024781) | PCI-24781 (CRA-024781) is a novel broad spectrum HDAC inhibitor targeting HDAC1, HDAC2, HDAC3, HDAC6, HDAC8 and HDAC10 with Ki of 7 nM, 19 nM, 8.2 nM, 17 nM, 280 nM, 24 nM, respectively. | PLoS One, 2013, 8(5), e65369; Nat Biotechnol, 2011, 29(3), 255-265. |

TABLE B-continued

| Inhibitor Name | Inhibitor Information | Literature Citations |
|---|---|---|
| Romidepsin (FK228, depsipeptide)<br>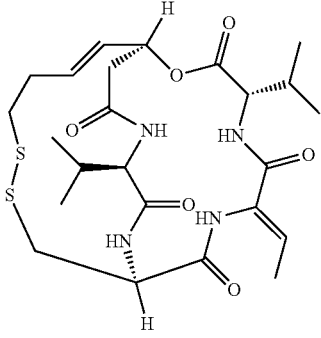 [SMILES: C/C=C1\NC(=O)[C@H]2CSSCC/C=C/[C@H](CC(=O)N[C@H](C(C)C)C(=O)N2)OC(=O)[C@H](C(C)C)NC1=O] | Romidepsin (FK228, FR901228, depsipeptide, NSC 630176) is a potent HDAC1 and HDAC2 inhibitor with IC50 of 36 nM and 47 nM, respectively. (1S,4S,7Z,10S,16E,21R)-7-ethylidene-4,21-bis(1methylethyl)-2-oxa-12,13-dithia-5,8,20,23-tetraazabicyclo[8.7.6]tricos-16ene-3.6,9,19,22-pentone | J Neurosci, 2013, 33(17):7535-7547; Br J Haematol, 2013. |
| AR-42 (OSU-HDAC42)<br>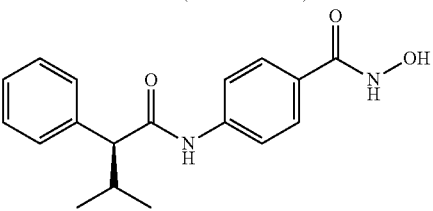<br>(S)-N-hydroxy-4-(3-methyl-2-phenylbutanamido)benzamide | AR-42 (HDAC-42, OSU-HDAC42) is a pan-HDAC inhibitor with IC50 30 nM. | |
| Valproic acid sodium salt (Sodium valproate) | Valproic acid sodium salt (Sodium valproate) is a HDAC inhibitor with IC50 of 0.4 mM and also inhibits GABA-transaminase or succinic semialdehyde dehydrogenase. | J Neurosci, 2013, 33(17), 7535-7547. |
| PCI-34051 | PCI-34051 is a potent and specific HPAC8 inhibitor with IC50 of 10 nM. | |
| CI994 (Tacedinaline)<br>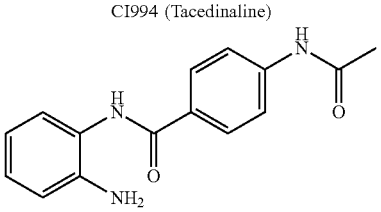 | CI994 (Tacedinaline) is an anti-cancer drug which inhibits HDAC1 with IC50 of 0.57 μM. | |
| M344 | M344 is a potent HDAC inhibitor with IC50 of 100 nM. | |
| PI3K/UDAC Inhibitor I | PI3K/HDAC Inhibitor I is a dual PI3K and HDAC inhibitor for PI3Kα, HDAC1, HDAC2, HDAC3 and HDAC10 with IC50 of 19 nM, 1.7 nM, 5 nM, 1.8 nM and 2.8 nM, respectively. | |
| Rocilinostat (ACY-1215)<br>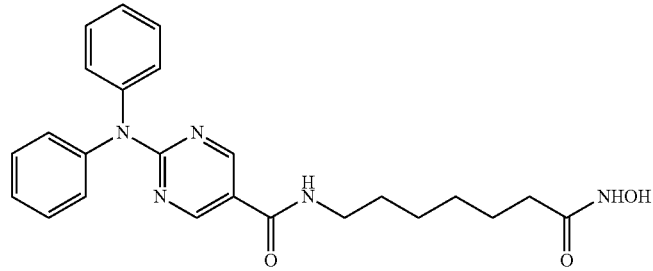 | Rocilinostat (ACY-1215) is a selective HDAC6 inhibitor with IC50 of 5 nM. | |

TABLE B-continued

| Inhibitor Name | Inhibitor Information | Literature Citations |
|---|---|---|
| Apicidin (OSI-2040) 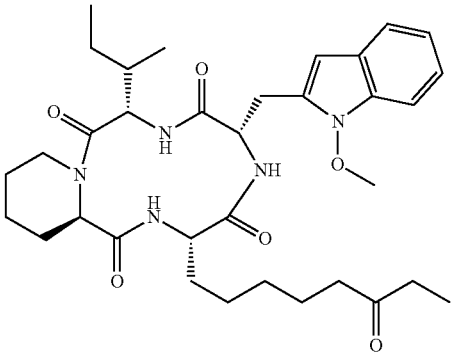 [SMILES: CCC(=O)CCCCC[C@@H]1NC(=O)[C@H]2CCCCN2C(=O)[C@H](C(C)CC)NC(=O)[C@H](Cc2cc3ccccc3n2OC)NC1=O] | Apicidin is a potent HDAC inhibitor with IC50 of 0.7 nM. (3S,6S,9S,15aR)-9-((R)-sec-butyl)-6-((1-methoxy-1H-indol-2-yl)methyl)-3-(6-oxooetyl)decahydro-1H-pyrido[1,2-a][1,4,7,10]tetraazacyclododecine-1,4,7,10(12H)-tetraone | |
| Scriptaid | Scriptaid is an inhibitor of HDAC. | |
| Tubastatin A 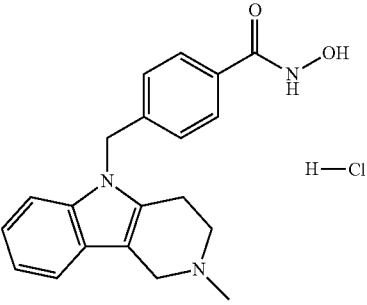 [SMILES: CN1CCc2c(c3ccccc3n2Cc2ccc(C(=O)NO)cc2)C1 ; Cl] N-hydroxy-4-((2-methyl-3,4-dihydro-1H-pyrido[4,3-b]indol-5(2H)-yl)methyl)benzamide hydrochloride | Tubastatin A is a potent and selective inhibitor of HDAC6 with IC50 of 15 nM. | J Biol Chem, 2013, 288(20), 14400-7. |
| Sodium Phenylbutyrate 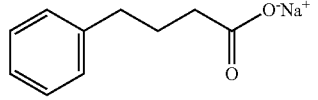 | Sodium Phenylbutyrate is a transcriptional regulators that act by altering chromatin structure via the modulation of HDAC activity. | |
| Resminostat (RAS2410) 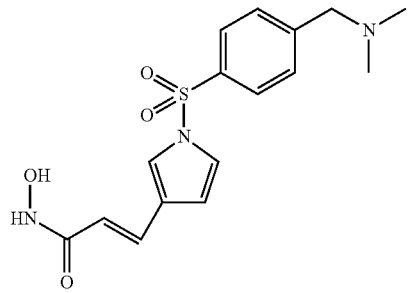 [SMILES: CN(C)Cc1ccc(S(=O)(=O)n2ccc(/C=C/C(=O)NO)c2)cc1] | (E)-3-(1-((4-((dimethylamino)methyl)phenyl)sulfonyl)-1H-pyrrol-3-yl)-N-hydroxyacrylamide | |

Example mammalian target of rapamycin (mTOR) inhibitors for use in combinations with the thienotriazolodiazepine of Formula (1) in the methods of the present invention include, but are not limited to, the mTOR inhibitors listed in the below Table C.

TABLE C

| No. | Inhibitor Name | Description | Literature Citations |
|---|---|---|---|
| 1 | BEZ235 (NVP-BEZ235) | BEZ235 (NVP-BEZ235) is a dual ATP-compelitive PI3K and mTOR inhibitor of p110α, p110γ, p110δ and p110β with IC50 of 4 nM, 5 nM, 7 nM and 75 nM, respectively, and also inhibits ATR with IC50 of 21 nM. | Nature, 2012, 487(7408):505-9; Blood, 2011, 118(14), 3911-3921; Cancer Res, 2011, 71(15), 5067-5074. |
| 2 | Everolimus (RAD001) | Everolimus (RAD001) is an mTOR inhibitor of FKBP12 with IC50 of 1.6-2.4 nM. | Cell, 2012, 149(3):656-70;; Cancer Cell, 2012, 21(2), 155-167; Clin Cancer Res, 2013, 19(3):598-609. |
| 3 | Rapamycin (Sirolimus, AY22989, NSC226080) | Rapamycin (Sirolimus, AY-22989, WY-090217) is a specific mTOR inhibitor with IC50 of ~0.1 nM. | Cancer Cell, 2011, 19(6), 792-804;; Cancer Res, 2013, ;Cell Res, 2012, 22(6):1003-21. |
| 4 | AZD8055 | AZD8055 is a novel ATP-competitive inhibitor of mTOR with IC50 of 0.8 nM. | Autophagy, 2012, Am J Transplant, 2013, ;Biochem Pharmacol, 2012, 83(9), 1183-1194 |
| 5 | PI-103<br><br>3-[4-(4-Morpholinylpyrido[3',2':4,5]f-uro[3,2-d]pyrimidin-2-yl]phenol | PI-103 is a potent, ATP-competitive PI3K inhibitor of DNA-PK, p110α, mTORC1, PI3KC2β, p110δ, mTORC2, p110β, and p110γ with IC50 of 2 nM, 8 nM, 20 nM, 26 nM, 48 nM, 83 nM, 88 nM and 150 nM, respectively. | Leukemia, 2013, 27(3):650-60; Leukemia, 2012, 26(5):927-33; Biochem Pharmacol, 2012, 83(9), 1183-1194. |

TABLE C-continued

| No. | Inhibitor Name | Description | Literature Citations |
|---|---|---|---|
| 6 | Temsirolimus (CCI-779, NSC-683864) | Temsirolimus (CCI-779, Torisel) is a specific mTOR inhibitor with IC50 of 1.76 nM. | Autophagy, 2011, 7(2), 176-187; Tuberc Respir Dis (Seoul), 2012, 72(4), 343-351; PLoS One, 2013, 8(5):e62104. |
| 7 | Ku-0063794<br><br>rel-5-[2-[(2R,6S)-2,6-dimethyl-4-mo-rpholinyl]-4-(4-morpholinyl)pyrido[2,3-d]pyrimidin-7-yl]-2-methoxybenzenemethanol | KU-0063794 is a potent and highly specific mTOR inhibitor for both mTORC1 and mTORC2 with IC50 ~10 nM. | Cell Stem Cell, 2012, 10(2):210-7; CircRes, 2010, 107(10), 1265-1274; J Immunol, 2013, 190(7), 3246-55. |
| 8 | GDC-0349 | GDC-0349, is a potent and selective ATP-competitive inhibitor of mTOR with Ki of 3.8 nM. | |
| 9 | Torin 2<br><br>9-(6-Amino-3-pyridinyl)-1-[3-(trifl-uoromethyl)phenyl]-benzo[h]-1,6-naphthyridin-2(1H)-one | Torin 2 is a highly potent and selective mTOR inhibitor with IC50 of 0.25 nM, and also exhibits potent cellular activity against ATM/ATR/DNA-PK with EC50 of 28 nM, 35 nM and 118 nM, respectively. | |

TABLE C-continued

| No. | Inhibitor Name | Description | Literature Citations |
|---|---|---|---|
| 10 | INK 128 (MLN-0128) | INK 128 is a potent and selective mTOR inhibitor with IC50 of 1 nM. | |
| 11 | AZD2014 | AZD2014 is a novel dual mTORC1 and mTORC2 inhibitor with potential antineoplastic activity. | |
| 12 | NVP-BGT226 (BGT226) | NVP-BGT226 is a novel dual PI3K/mTOR inhibitor with IC50 of 1 nM. | |
| 13 | PF-04691502 | PF-04691502 is an ATP-competitive, selective inhibitor of PI3K($\alpha/\beta/\delta/\gamma$)/mTOR with Ki of 1.8 nM/ 2.1 nM/1.6 nM/ 1.9 nM and 16 nM, also inhibits Akt phosphorylation on T308/S473 with IC50 of 7.5 nM/3.8 nM. | |

TABLE C-continued

| No. | Inhibitor Name | Description | Literature Citations |
|---|---|---|---|
| 14 | CH5132799 | CH5132799 exhibits a strong inhibitory activity especially against PI3Kα with IC50 of 14 nM and also inhibits mTOR with IC50 of 1.6 μM. | |
| 15 | GDC-0980 (RG7422) | GDC-0980 (RG7422) is a potent, selective inhibitor of PI3Kα, PI3Kβ, PI3Kδ and PI3Kγ with IC50 of 5 nM, 27 nM, 7 nM, and 14 nM, and also a mTOR inhibitor with Ki of 17 nM. | |
| 16 | Torin 1<br>1-[4-[4-(1-Oxopropyl)-1-piperazinyl-]-3-(trifluoromethyl)phenyl]-9-(3-quinolinyl)-benz-o[h]-1,6-naphthyridin-2(1H)-one | Torin1 is a potent inhibitor of mTOR with IC50 of 2-10 nM. | |
| 17 | WAY-600 | WAY-600 is a potent, ATP-competitive and selective inhibitor of mTOR with IC50 of 9 nM. | |

TABLE C-continued

| No. | Inhibitor Name | Description | Literature Citations |
|---|---|---|---|
| 18 | WYE-125132 (WYE-132) | WYE-125132 is a highly potent, ATP-competitive and specific mTOR inhibitor with IC50 of 0.19 nM. | |
| 19 | WYE-687 | WYE-687 is an ATP-competitive and selective inhibitor of mTOR with IC50 of 7 nM. | |
| 20 | GSK2126458 (GSK458) | GSK2126458 is a highly selective and potent inhibitor of p110α, p110β, p110γ, p110δ, mTORC1 and mTORC2 with Ki of 0.019 nM, 0.13 nM, 0.024 nM, 0.06 nM, 0.18 nM and 0.3 nM, respectively. | |

TABLE C-continued

| No. | Inhibitor Name | Description | Literature Citations |
|---|---|---|---|
| 21 | PF-05212384 (PKI-587) 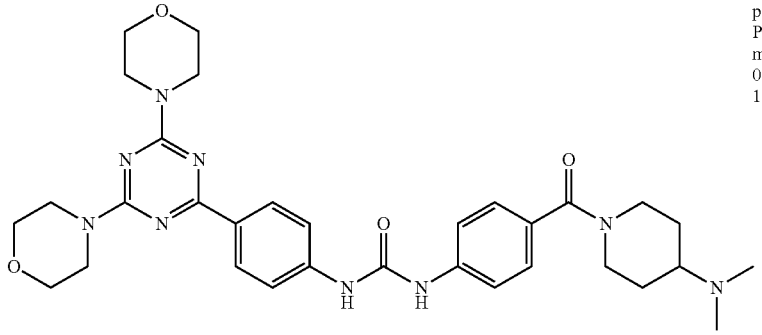 | PKI-587 is a highly potent dual inhibitor of PI3Kα, PBKγ and mTOR with IC50 of 0.4 nM, 5.4 nM and 1.6 nM, respectively. | |
| 22 | PP-121 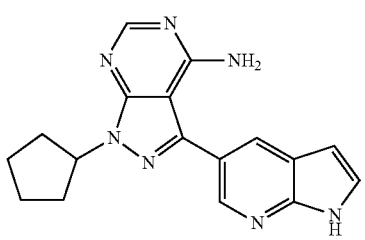 [SMILES: Nc1ncnc2c1c(-c1cnc3[nH]ccc3c1)nn2C1CCCC1]<br>1-Cyclopentyl-3-(1H-pyrrolo[2,3-b]p-yridin-5-yl)-1H-pyrazolo[3,4-d]pyrimidin-4-amine | PP-121 is a multi-target inhibitor of PDGFR, Hck, mTOR, VEGFR2, Src and Abl with IC50 of 2 nM, 8 nM, 10 nM, 12 nM, 14 nM and 18 nM, respectively, and also inhibits DNA-PK with IC50 of 60 nM. | |
| 23 | OSI-027 (ASP4786) 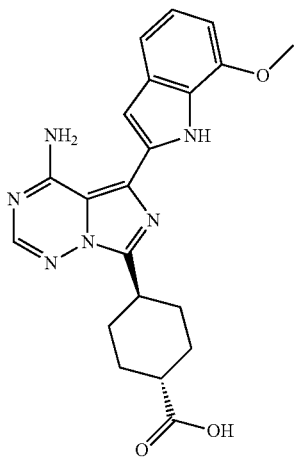 [SMILES: COc1cccc2cc(-c3nc([C@H]4CC[C@H](C(=O)O)CC4)n4ncnc(N)c34)[nH]c12] | OSI-027 is a selective and potent dual inhibitor of mTORC1 and mTORC2 with IC50 of 22 nM and 65 nM, respectively. | Exp Eye Res, 2013, 113C, 9-18 |
| 24 | Palomid 529 (P529) 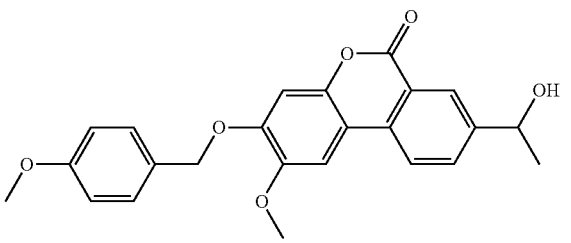 [SMILES: COc1ccc(COc2cc3oc(=O)c4cc(C(C)O)ccc4c3cc2OC)cc1] | Palomid 529 inhibits both the mTORC1 and mTORC2 complexes, reduces phosphorylation of pAktS473, PGSK3βS9, and pS6 but neither pMAPK nor pAktT308. Phase 1. | |

TABLE C-continued

| No. | Inhibitor Name | Description | Literature Citations |
|---|---|---|---|
| 25 | PP242<br><br>2-[4-Amino-1-(1-methylethyl)-1H-pyr-azolo[3,4-d]pyrimidin-3-yl]-1H-indol-5-ol | PP242 is a selective mTOR inhibitor with IC50 of 8 nM. | Autophagy, 2012, 8(6), 903-914 |
| 26 | XL765 (SAR245409) | XL765 is a dual inhibitor of mTOR/PI3k for mTOR, p110α, p110β, p110γ and p110δ with IC50 of 157 nM, 39 nM, 113 nM, 9 nM and 43 nM, respectively. | Endocrinology, 2013, 154(3):1247-59 |
| 27 | GSK1059615<br><br>5-[[4-(4-Pyridinyl)-6-quinolinyl]me-thylene]-2,4-thiazolidenedione | GSK1059615 is a novel and dual inhibitor of PI3Kα, PDKβp, PI3Kδ, PI3Kγ and mTOR with IC50 of 0.4 nM, 0.6 nM, 2 nM, 5 nM and 12 nM, respectively. | Nature, 2012, 486(7404), 532-536 |
| 28 | WYE-354 | WYE-354 is a potent, specific and ATP-competitive inhibitor of mTOR with IC50 of 5 nM. | Mol Cancer Res, 2012, 10(6), 821-833. |

TABLE C-continued

| No. | Inhibitor Name | Description | Literature Citations |
|---|---|---|---|
| 29 | Deforolimus (Ridaforolimus, MK-8669) 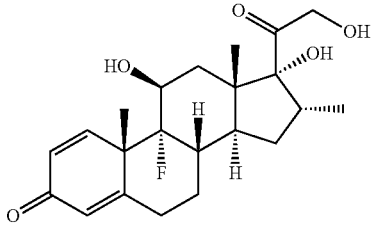 | Deforolimus (Ridaforolimus; AP23573; MK-8669; 42-(Dimethylphosphinate)rapamycin; Ridaforolimus) is a selective mTOR inhibitor with IC50 of 0.2 nM. | Mol Genet Meta, 2010, 100(4), 309-315. |

Suitable glucocorticoids for use in combinations with the thienotriazolodiazepine of Formula (1) in the methods of the present invention include, but are not limited to, the glucocorticoids listed in the below Table D.

TABLE D

| No. | Glucocorticoid Name | Glucocorticoid Structure |
|---|---|---|
| 1 | dexamethasone | 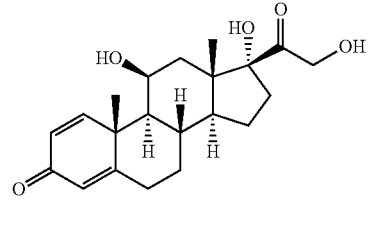 |
| 2 | prednisolone | 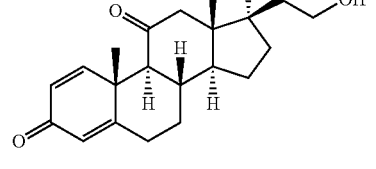 |
| 3 | prednisone | 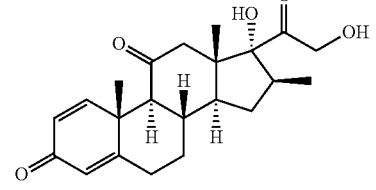 |
| 4 | methyl-prednisolone | 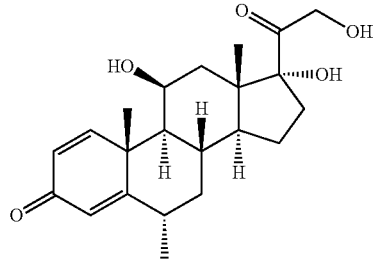 |
| 5 | betamethasone | 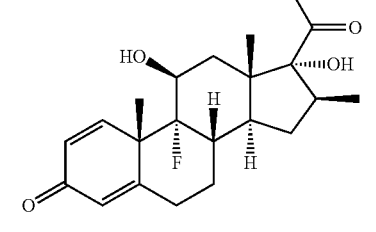 |

TABLE D-continued

| No. | Glucocorticoid Name | Glucocorticoid Structure |
|---|---|---|
|  | meprednisone |  |

TABLE D-continued

| Glucocorticoid | | |
|---|---|---|
| No. | Name | Glucocorticoid Structure |
| 6 | triamicinolone | 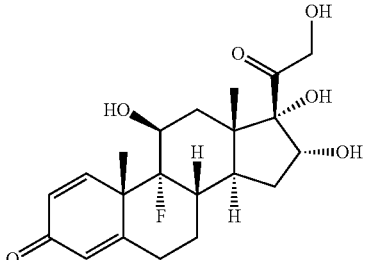 |
| 7 | fludrocortisone | 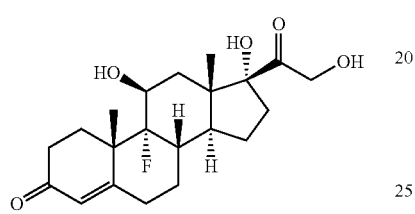 |
| 8 | beclamethasone | 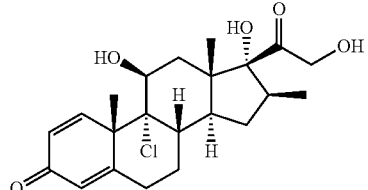 |

Suitable conventional cytotoxic drugs for use in combinations with the thienotriazolodiazepine of Formula (1) in the methods of the present invention include, but are not limited to, the cytotoxic drugs listed in the below Table E.

TABLE E

| | |
|---|---|
| daunorubicin | 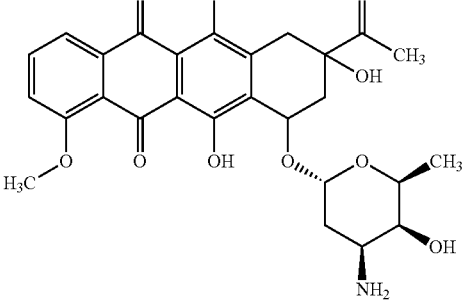 |
| cytarabine | 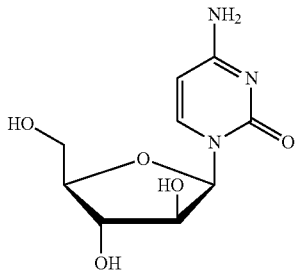 |
| methotrexate | 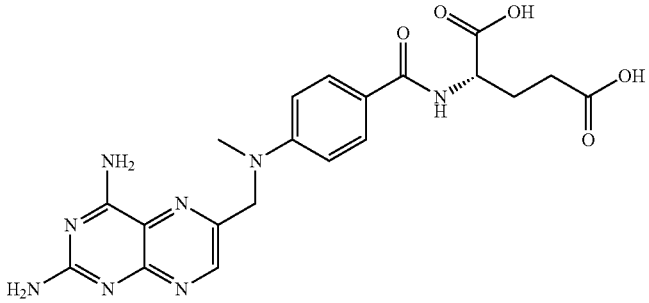 [SMILES: CN(Cc1cnc2nc(N)nc(N)c2n1)c1ccc(C(=O)N[C@@H](CCC(=O)O)C(=O)O)cc1] |

III. THIENOTRIAZOLODIAZEPINE COMPOUNDS

In one embodiment, the thienotriazolodiazepine compounds, used in the formulations of the present invention, are represented by Formula (1):

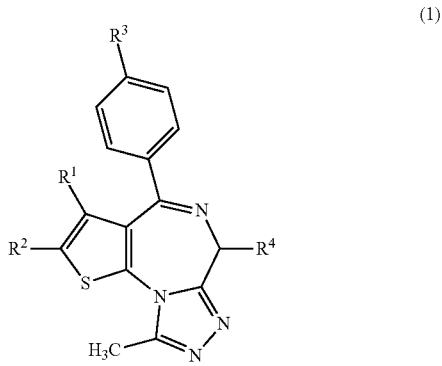

wherein
$R^1$ is alkyl having a carbon number of 1-4, $R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, including any salts, isomers, enantiomers, racemates, hydrates, solvates, metabolites, and polymorphs thereof.

In one embodiment, a suitable alkyl group includes linear or branched alkyl radicals including from 1 carbon atom up to 4 carbon atoms. In one embodiment, a suitable alkyl group includes linear or branched alkyl radicals including from 1 carbon atom up to 3 carbon atoms. In one embodiment, a suitable alkyl group includes linear or branched alkyl radicals include from 1 carbon atom up to 2 carbon atoms. In one embodiment, exemplary alkyl radicals include, but are not limited to, methyl, ethyl, propyl, isopropyl, n-butyl, isobutyl, sec-butyl, tert-butyl. In one embodiment, exemplary alkyl groups include, but are not limited to, methyl, ethyl, propyl, isopropyl, 2-methyl-1-propyl, and 2-methyl-2-propyl.

In some embodiments, the present invention provides pharmaceutically acceptable salts, solvates, including hydrates, and isotopically-labeled forms of the thienotriazolodiazepine compounds described herein. In one embodiment, pharmaceutically acceptable salts of the thienotriazolodiazepine compounds include acid addition salts formed with inorganic acids. In one embodiment, pharmaceutically acceptable inorganic acid addition salts of the thienotriazolodiazepine include salts of hydrochloric, hydrobromic, hydroiodic, phosphoric, metaphosphoric, nitric and sulfuric acids. In one embodiment, pharmaceutically acceptable salts of the thienotriazolodiazepine compounds include acid addition salts formed with organic acids. In one embodiment, pharmaceutically acceptable organic acid addition salts of the thienotriazolodiazepine include salts of tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and 4-methyl benzenesulfonic acids.

The present invention provides pharmaceutically acceptable isotopically-labeled forms of the thienotriazolodiazepine compounds, described herein, wherein one or more atoms are replaced by atoms having the same atomic number, but an atomic mass or mass number different from the atomic mass or mass number usually found in nature. Examples of isotopes suitable for inclusion in the thienotriazolodiazepine compounds include isotopes of hydrogen, e.g., $^2$H and $^3$H, carbon, e.g., $^{11}$C, $^{13}$C and $^{14}$C, chlorine, e.g., $^{36}$Cl, fluorine, e.g., $^{18}$F, iodine, e.g., $^{123}$I and $^{125}$I, nitrogen, e.g., $^{13}$N and $^{15}$N, oxygen, e.g., $^{15}$O, $^{17}$O and $^{18}$O, and sulfur, e.g., $^{35}$S. Isotopically-labeled forms of the thienotriazolodiazepine compounds generally can be prepared by conventional techniques known to those skilled in the art.

Certain isotopically-labeled forms of the compound of Formula (1), for example those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with heavier isotopes such as deuterium ($^2$H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be used in Positron Emission Tomography (PET) studies for examining substrate receptor occupancy.

In some embodiments, the thienotriazolodiazepine compounds disclosed herein can exist in solvated as well as unsolvated forms with pharmaceutically acceptable solvents. It will be understood by those skilled-in the art that a solvate is a complex of variable stoichiometry formed by a solute (in this case, the thienotriazolodiazepine compounds described herein) and a solvent. It is preferred that such solvents not interfere with the biological activity of the solute (the thienotriazolodiazepine compounds). Examples of suitable solvents for solvate formation include, but are not limited to, water, methanol, dimethyl sulfoxide, ethanol and acetic acid. Suitably the solvent used is a pharmaceutically acceptable solvent. Suitably the solvent used is water. In one embodiment, pharmaceutically acceptable solvates of the thienotriazolodiazepine compounds, described herein, include ethanol solvate, a isopropanol solvate, a dioxolane solvate, a tetrahydrofuran solvate, a dimethyl sulfoxide solvate, tert-butanol solvate, 2-butanol solvate, dioxolane solvate, 1,3-Dimethyl-3,4,5,6-tetrahydro-2(1H)-pyrimidinone ("DMPU") solvate, 1,3-dimethylimidazolidinone ("DMI") solvate, and 1,3-dimethylimidazolidinone ("DMP") solvate, or mixtures thereof.

In some embodiments, the thienotriazolodiazepine compounds, described herein, may contain one or more chiral centers and/or double bonds and, therefore, may exist as geometric isomers, enantiomers or diastereomers. The enantiomer and diastereomers of the thienotriazolodiazepine compounds may be designated in accordance with the Cahn-Ingold-Prelog convention, which assigns an "R" or "S" descriptor to each stereocenter (also sometimes referred to as a chiral center) and an E or Z descriptor to each carbon-carbon double bond (to designate geometric isomers) so that the configuration of the entire molecule can be specified uniquely by including the descriptors in its systematic name.

In some embodiments, the thienotriazolodiazepine compounds, described herein, may exist as a racemic mixture, or racemate, which includes equal amounts of left- and right-handed enantiomers of a chiral molecule. Such a racemic mixture may be denoted by the prefix (±)- or dl-, indicating an equal (1:1) mixture of dextro and levo isomers. Also, the prefix rac- (or racem-) or the symbols RS and SR may be used to designate the racemic mixture.

Geometric isomers, resulting from the arrangement of substituents around a carbon-carbon double bond or arrangement of substituents around a cycloalkyl or heterocyclic ring, can also exist in the compounds of the present invention. In some embodiments, the symbol ===== may be used to denote a bond that may be a single, double or triple bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of a plane of a ring are designated "cis/trans" or "Z/E."

In some embodiments, thienotriazolodiazepine compounds disclosed herein may exist in single or multiple crystalline forms or polymorphs. In one embodiment, a thienotriazolodiazepine compound disclosed herein comprises an amorphous form thereof. In one embodiment, a thienotriazolodiazepine compound disclosed herein comprises a single polymorph thereof. In another embodiment, a thienotriazolodiazepine compound disclosed herein comprises a mixture of polymorphs thereof. In another embodiment, the compound is in a crystalline form.

In some embodiments, thienotriazolodiazepine compounds disclosed herein may exist as a single enantiomers or in enatiomerically enriched forms. In one embodiment, a thienotriazolodiazepine compound disclosed herein exists in an entiomeric excess of more than 80%. In one embodiment, a thienotriazolodiazepine compound disclosed herein exists in an entiomeric excess of more than 90%. In one embodiment, a thienotriazolodiazepine compound disclosed herein exists in an entiomeric excess of more than 98%. In one embodiment, a thienotriazolodiazepine compound disclosed herein exists in an entiomeric excess of more than 99%. In some embodiments, a thienotriazolodiazepine compound disclosed herein exists in an entiomeric excess selected from the group consisting of at least 10%, at least 25%, at least 50%, at least 75%, at least 90%, at least 95%, at least 98%, at least and at least 99% enantiomeric excess.

For a pair of enantiomers, enantiomeric excess (ee) of enantiomer E1 in relation to enantiomer E2 can be calculated using the following equation eq. (1):

$$\% \text{ enantiomeric excess of } E1 = \frac{(E1 - E2) \times 100\%}{(E1 + E2)} \qquad \text{eq. (1)}$$

Relative amounts of E1 and E2 can be determined by chiral high performance liquid chromatography (HPLC), nuclear magnetic resonance (NMR) or any other suitable methods. In some embodiments, purity of an entiormeric compound may refer to the amount of the enantiomers E1 and E2, relative to the amount of other materials, which may notably include by-products and/or unreacted reactants or reagents.

In some embodiments, thienotriazolodiazepine compounds of Formula (1) include, but are not limited to, the thienotriazolodiazepine compounds (1-1) to (1-18), which are listed in the following Table A.

Compound (1-1), of Table A, may also be referred to herein as OTX-015, OTX015 or Y803.

TABLE A

Exemplary compounds which may be used in the formulations described herein:

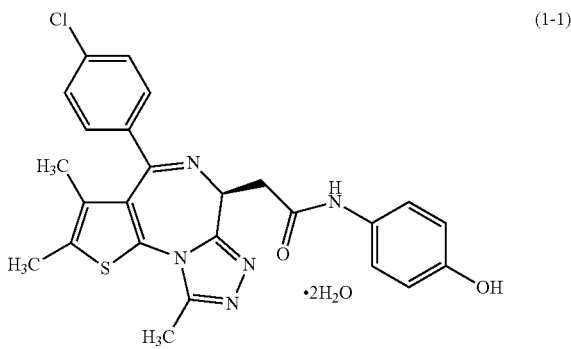
(1-1)

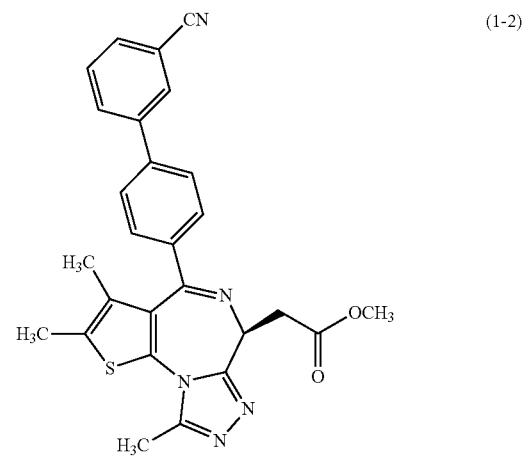
(1-2)

TABLE A-continued
Exemplary compounds which may be used in the formulations described herein:
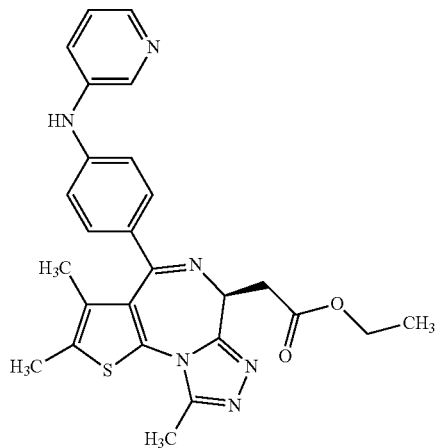 [SMILES: CCOC(=O)C[C@@H]1N=C(c2ccc(Nc3cccnc3)cc2)c2c(sc(C)c2C)-n2c(C)nnc21] (1-3)
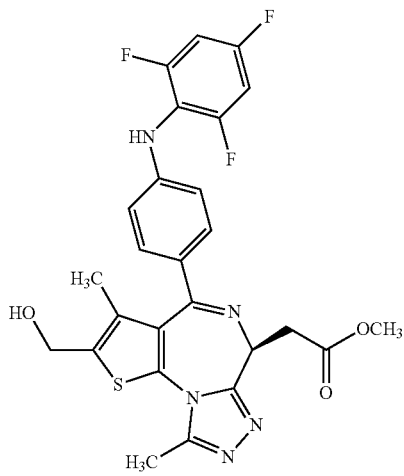 [SMILES: COC(=O)C[C@@H]1N=C(c2ccc(Nc3c(F)cc(F)cc3F)cc2)c2c(sc(CO)c2C)-n2c(C)nnc21] (1-4)
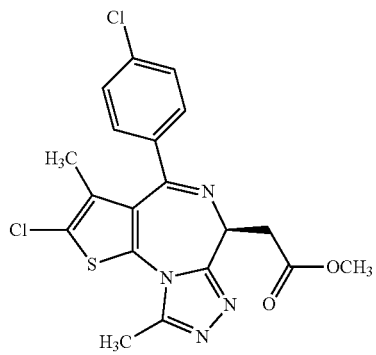 [SMILES: COC(=O)C[C@@H]1N=C(c2ccc(Cl)cc2)c2c(sc(Cl)c2C)-n2c(C)nnc21] (1-5)
TABLE A-continued
Exemplary compounds which may be used in the formulations described herein:
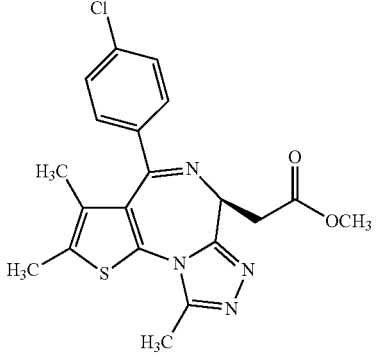 [SMILES: COC(=O)C[C@@H]1N=C(c2ccc(Cl)cc2)c2c(sc(C)c2C)-n2c(C)nnc21] (1-6)
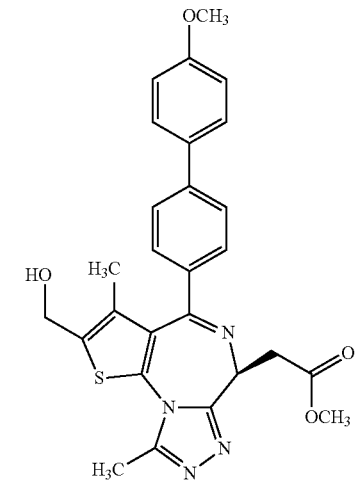 [SMILES: COC(=O)C[C@@H]1N=C(c2ccc(-c3ccc(OC)cc3)cc2)c2c(sc(CO)c2C)-n2c(C)nnc21] (1-7)
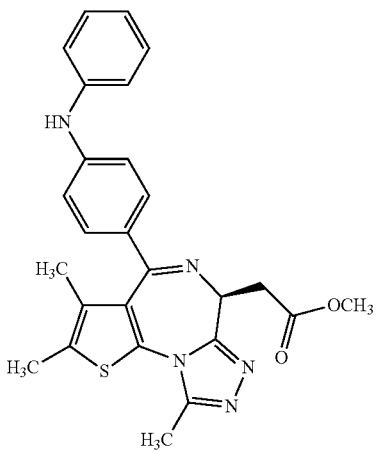 [SMILES: COC(=O)C[C@@H]1N=C(c2ccc(Nc3ccccc3)cc2)c2c(sc(C)c2C)-n2c(C)nnc21] (1-8)

TABLE A-continued
Exemplary compounds which may be used in the formulations described herein:
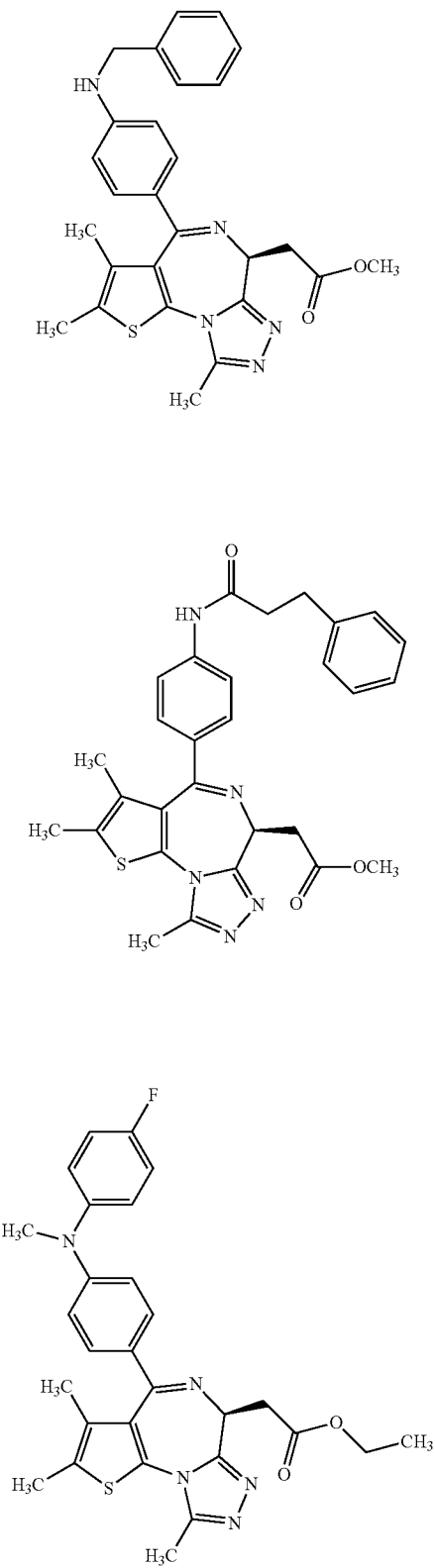

TABLE A-continued

Exemplary compounds which may be
used in the formulations described herein:

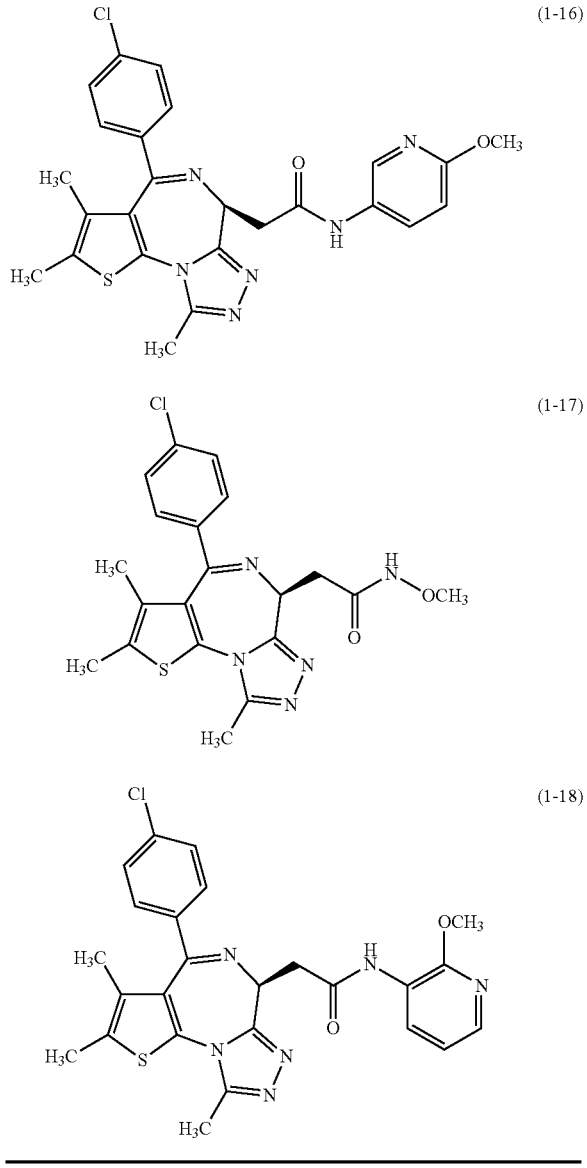

(1-16)

(1-17)

(1-18)

In some embodiments, thienotriazolodiazepine compounds of Formula (1) include (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]tri-azolo[4,3-a][1,4]diazepin-6-yl}acetate, (iii) methyl (S)-{2,3,9-trimethyl-4-(4-phenylaminophenyl)-6H-thieno[3,2-f][1,2,4]triaz-olo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate.

In some embodiments, thienotriazolodiazepine compounds of Formula (1) include (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide.

IV. FORMULATIONS

The compound of Formula (1) presents highly specific difficulties in relation to administration generally and the preparation of galenic compositions in particular, including the particular problems of drug bioavailability and variability in inter- and intra-patient dose response, necessitating development of a non-conventional dosage form with respect to the practically water-insoluble properties of the compound.

Previously, it had been found that the compound of Formula (1) could be formulated as a solid dispersion with the carrier ethyl acrylate-methyl methacrylate-trimethylammonioethyl methacrylate chloride copolymer (Eudragit RS, manufactured by Rohm) to provide an oral formulation that preferentially released the pharmaceutical ingredient in the lower intestine for treatment of inflammatory bowel diseases such as ulcerative colitis and Crohn's disease (US Patent Application 20090012064 A1, published Jan. 8, 2009). It was found, through various experiments, including animal tests, that in inflammatory bowel diseases drug release in a lesion and a direct action thereof on the inflammatory lesion were more important than the absorption of the drug into circulation from the gastrointestinal tract.

It has now been unexpectedly found that thienotriazolodiazepine compounds, according to Formula (1), pharmaceutically acceptable salts, solvates, including hydrates, racemates, enantiomers isomers, and isotopically-labeled forms thereof, can be formulated as a solid dispersion with pharmaceutically acceptable polymers to provide an oral formulation that provides high absorption of the pharmaceutical ingredient into the circulation from the gastrointestinal tract for treatment of diseases other than inflammatory bowel diseases. Studies in both dogs and humans have confirmed high oral bioavailability of these solid dispersions compared with the Eudragit solid dispersion formulation previously developed for the treatment of inflammatory bowel disease.

Solid dispersions are a strategy to improve the oral bioavailability of poorly water soluble drugs.

The term "solid dispersion" as used herein refers to a group of solid products including at least two different components, generally a hydrophilic carrier and a hydrophobic drug, the thienotriazolodiazepine compounds, according to Formula (1). Based on the drug's molecular arrangement within the dispersion, six different types of solid dispersions can be distinguished. Commonly, solid dispersions are classified as simple eutectic mixtures, solid solutions, glass solution and suspension, and amorphous precipitations in a crystalline carrier. Moreover, certain combinations can be encountered, for example, in the same sample some molecules may be present in clusters while some are molecularly dispersed.

In one embodiment, the thienotriazolodiazepine compounds, according to Formula (1) can be dispersed molecularly, in amorphous particles (clusters). In another embodiment, the thienotriazolodiazepine compounds, according to Formula (1) can be dispersed as crystalline particles. In one embodiment, the carrier can be crystalline. In another embodiment, the carrier can be amorphous.

In one embodiment, the present invention provides a pharmaceutical composition comprising a solid dispersion of a thienotriazolodiazepine compound, in accordance with Formula (1), or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is hypromellose acetate succinate (also called hydroxypropylmethylcellulose acetate succinate or HPMCAS). In one embodiment, the dispersion has a thienotriazolodiazepine compound to hydroxypropylmethylcellulose acetate succinate (HPMCAS) weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1). In some embodiments, the hydroxypropylmethyl cellulose acetate succinates (HPMCAS), may include M grade having 9% acetyl/11% succinoyl (e.g., HPMCAS having a mean particle size of 5 μm (i.e., HPMCAS-MF, fine powder grade) or having a mean particle size of 1 mm (i.e., HPMCAS-MG, granular grade)), H grade having 12% acetyl/6% succinoyl (e.g., HPMCAS having a mean particle size of 5 μm (i.e., HPMCAS-HF, fine powder grade) or having a mean particle size of 1 mm (i.e., HPMCAS-HG, granular grade)), and L grade having 8% acetyl/15% succinoyl (e.g., HPMCAS having a mean particle size of 5 μm (i.e., HPMCAS-LF, fine powder grade) or having a mean particle size of 1 mm (i.e., HPMCAS-LG, granular grade).

In one embodiment, the present invention provides a pharmaceutical composition comprising a solid dispersion of a thienotriazolodiazepine compound of Formula (1) or a pharmaceutically acceptable salt, a solvate, including a hydrate, a racemate, an enantiomer, an isomer, or an isotopically-labeled form thereof in a pharmaceutically acceptable polymer. In one embodiment, the pharmaceutically acceptable polymer is polyvinylpyrrolidone (also called povidone or PVP). In one embodiment, the dispersion has a thienotriazolodiazepine compound to PVP weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1). In some embodiments, the polyvinyl pyrrolidones may have molecular weights of about 2,500 (Kollidon®12 PF, weight-average molecular weight between 2,000 to 3,000), about 9,000 (Kollidon® 17 PF, weight-average molecular weight between 7,000 to 11,000), about 25,000 (Kollidon® 25, weight-average molecular weight between 28,000 to 34,000), about 50,000 (Kollidon® 30, weight-average molecular weight between 44,000 to 54,000), and about 1,250,000 (Kollidon® 90 or Kollidon® 90F, weight-average molecular weight between 1,000,000 to 1,500,000).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In some embodiments, a pharmaceutical composition comprising a solid dispersion is prepared by spray drying.

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of compound (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of compound (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In some such embodiments, the solid dispersion was exposed to a relative humidity of 75% at 40° C. for at least one month. In other such embodiments, the single Tg occurs at about 135° C. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In one preferred embodiment, the present invention provides a pharmaceutical composition comprising a solid dispersion of 2-[(6S)-4-(4-chlorophenyl)-2,3,9-trimethyl-6H-thieno[3,2-f]-[1,2,4]triazolo[4,3-a][1,4]diazepin-6-yl]-N-(4-hydroxyphenyl)acetamide dihydrate, compound (1-1):

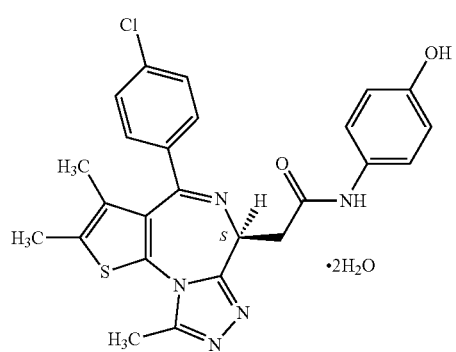

(1-1)

or a pharmaceutically acceptable salt, a solvate, including a hydrate, a racemate, an enantiomer, an isomer, or an isotopically-labeled form and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In another embodiment, the pharmaceutical composition comprises a solid dispersion compound (1-1) or a pharmaceutically acceptable salt, a solvate, including a hydrate, a racemate, an enantiomer, an isomer, or an isotopically-labeled form; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 189° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, the solid dispersion is spray dried.

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, the solid dispersion is spray dried.

The solid dispersions of the invention, described herein, exhibit especially advantageous properties when administered orally. Examples of advantageous properties of the solid dispersions include, but are not limited to, consistent and high level of bioavailability when administered in standard bioavailability trials in animals or humans. The solid dispersions of the invention can include a solid dispersion comprising thienotriazolodiazepine compound of Formula (1) and a polymer and additives. In some embodiments, the solid dispersions can achieve absorption of the thienotriazolodiazepine compound of Formula (1) into the bloodstream that cannot be obtained by merely admixing the thienotriazolodiazepine compound of Formula (1) with additives since the thienotriazolodiazepine compound of Formula (1) drug has negligible solubility in water and most aqueous media. The bioavailability, of thienotriazolodiazepine compound of Formula (1) or of thienotriazolodiazepine compound (1-1) may be measured using a variety of in vitro and/or in vivo studies. The in vivo studies may be performed, for example, using rats, dogs or humans.

The bioavailability may be measured by the area under the curve (AUC) value obtained by plotting a serum or plasma concentration, of the thienotriazolodiazepine compound of Formula (1) or thienotriazolodiazepine compound (1-1), along the ordinate (Y-axis) against time along the abscissa (X-axis). The AUC value of the thienotriazolodiazepine compound of Formula (1) or thienotriazolodiazepine compound (1-1) from the solid dispersion, is then compared to the AUC value of an equivalent concentration of crystalline thienotriazolodiazepine compound of Formula (1) or crystalline thienotriazolodiazepine compound (1-1) without polymer. In some embodiments, the solid dispersion provides an area under the curve (AUC) value, when administered orally to a dog, that is selected from: at least 0.4 times, 0.5 times, 0.6 time, 0.8 time, 1.0 times, a corresponding AUC value provided by a control composition administered intravenously to a dog, wherein the control composition comprises an equivalent quantity of a crystalline thienotriazolodiazepine compound of Formula (1).

The bioavailability may be measured by in vitro tests simulating the pH values of a gastric environment and an intestine environment. The measurements may be made by suspending a solid dispersion of the thienotriazolodiazepine compound of Formula (1) or thienotriazolodiazepine compound (1-1), in an aqueous in vitro test medium having a pH between 1.0 to 2.0, and the pH is then adjusted to a pH between 5.0 and 7.0, in a control in vitro test medium. The concentration of the amorphous thienotriazolodiazepine compound of Formula (1) or amorphous thienotriazolodiazepine compound (1-1) may be measured at any time during the first two hours following the pH adjustment. In some embodiments, the solid dispersion provides a concentration, of the amorphous thienotriazolodiazepine compound of Formula (1) or amorphous thienotriazolodiazepine compound (1-1), in an aqueous in vitro test medium at pH between 5.0 to 7.0 that is selected from: at least 5-fold greater, at least 6 fold greater, at least 7 fold greater, at least 8 fold greater, at least 9 fold greater or at least 10 fold greater, compared to a concentration of a crystalline thienotriazolodiazepine compound of Formula (1) or crystalline thienotriazolodiazepine compound (1-1), without polymer.

In other embodiments, the concentration of the amorphous thienotriazolodiazepine compound of Formula (1) or amorphous thienotriazolodiazepine compound (1-1), from the solid dispersion placed in an aqueous in vitro test medium having a pH of 1.0 to 2.0, is: at least 40%, at least 50% higher, at least 60%, at least 70%; at least 80%, than a concentration of a crystalline thienotriazolodiazepine compound of Formula (1) without polymer. In some such embodiments, the polymer of the solid dispersion is HPMCAS. In some such embodiments, the polymer of the solid dispersion is PVP.

In other embodiments, a concentration of the amorphous thienotriazolodiazepine compound of Formula (1) or amorphous thienotriazolodiazepine compound (1-1), from the solid dispersion, is: at least 40%, at least 50% higher, at least 60%, at least 70%; at least 80%, compared to a concentration of thienotriazolodiazepine compound of Formula (1), from a solid dispersion of thienotriazolodiazepine compound of the Formula (1) and a pharmaceutically acceptable polymer selected from the group consisting of: hypromellose phthalate and ethyl acrylate-methyl methacrylate-trimethylammonioethyl methacrylate chloride copolymer, wherein each solid dispersion was placed in an aqueous in vitro test medium having a pH of 1.0 to 2.0. In some such embodiments, the polymer of the solid dispersion is HPMCAS. In some such embodiments, the polymer of the solid dispersion is PVP.

In some embodiments, the solid dispersions, described herein, exhibit stability against recrystallization of the thienotriazolodiazepine compound of the Formula (1) or the thienotriazolodiazepine compound (1-1) when exposed to humidity and temperature over time. In one embodiment, the concentration of the amorphous thienotriazolodiazepine compound of the Formula (1) or the thienotriazolodiazepine compound (1-1) which remains amorphous is selected from: at least 90%, at least 91%, at least 92%, at least 93%, at least 94%, at least 95%, at least 96%, at least 97%, at least 98% and at least 99%.

V. DOSAGE FORMS

Suitable dosage forms that can be used with the solid dispersions of the present invention include, but are not limited to, capsules, tablets, mini-tablets, beads, beadlets, pellets, granules, granulates, and powder. Suitable dosage forms may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxylpropylmethylcellulose acetate succinate (HPMCAS). In some embodiments, certain combinations can be encountered, for example, in the same sample some molecules of the thienotriazolodiazepine of the present invention may be present in clusters while some are molecularly dispersed with a carrier.

In some embodiments, the solid dispersions of the invention may be formulated as tablets, caplets, or capsules. In one some embodiments, the solid dispersions of the invention may be formulated as mini-tablets or pour-into-mouth granules, or oral powders for constitution. In some embodiments, the solid dispersions of the invention are dispersed in a suitable diluent in combination with other excipients (e.g., re-crystallization/precipitation inhibiting polymers, taste-masking components, etc.) to give a ready-to-use suspension formulation. In some embodiments, the solid dispersions of the invention may be formulated for pediatric treatment.

In one embodiment, the pharmaceutical composition of the present invention is formulated for oral administration. In one embodiment, the pharmaceutical composition comprises a solid dispersion, according to the various embodiments described herein, comprising a thienotriazolodiazepine compound of Formula (1) or a pharmaceutically acceptable salt, a solvate, including a hydrate, a racemate, an enantiomer, an isomer, or an isotopically-labeled form thereof; and a polymer carrier. In one embodiment, the pharmaceutical composition further includes one or more additives such as disintegrants, lubricants, glidants, binders, and fillers.

Examples of suitable pharmaceutically acceptable lubricants and pharmaceutically acceptable glidants for use with the pharmaceutical composition include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose, glyceryl behenate, stearic acid, hydrogenated castor oil, glyceryl monostearate, and sodium stearyl fumarate.

Examples of suitable pharmaceutically acceptable binders for use with the pharmaceutical composition include, but are not limited to starches; celluloses and derivatives thereof, e.g., microcrystalline cellulose (e.g., AVICEL PH from FMC), hydroxypropyl cellulose, hydroxyethyl cellulose, and hydroxylpropylmethylcellulose (HPMC, e.g., METHOCEL from Dow Chemical); sucrose, dextrose, corn syrup; polysaccharides; and gelatin.

Examples of suitable pharmaceutically acceptable fillers and pharmaceutically acceptable diluents for use with the pharmaceutical composition include, but are not limited to, confectioner's sugar, compressible sugar, dextrates, dextrin, dextrose, lactose, mannitol, microcrystalline cellulose (MCC), powdered cellulose, sorbitol, sucrose, and talc.

In some embodiments, excipients may serve more than one function in the pharmaceutical composition. For example, fillers or binders may also be disintegrants, glidants, anti-adherents, lubricants, sweeteners and the like.

In some embodiments, the pharmaceutical compositions of the present invention may further include additives or ingredients, such as antioxidants (e.g., ascorbyl palmitate, butylated hydroxylanisole (BHA), butylated hydroxytoluene (BHT), α-tocopherols, propyl gallate, and fumaric acid), antimicrobial agents, enzyme inhibitors, stabilizers (e.g., malonic acid), and/or preserving agents.

Generally, the pharmaceutical compositions of the present invention may be formulated into any suitable solid dosage form. In some embodiments, the solid dispersions of the invention are compounded in unit dosage form, e.g., as a capsule, or tablet, or a multi-particulate system such as granules or granulates or a powder, for administration.

In one embodiment, a pharmaceutical compositions includes a solid dispersion of a thienotriazolodiazepine compound of Formula (1), according to the various embodiments of solid dispersions described herein, and hydroxypropylmethylcellulose acetate succinate (HPMCAS), wherein the thienotriazolodiazepine compound is amorphous in the solid dispersion and has a thienotriazolodiazepine compound to hydroxypropylmethylcellulose acetate succinate (HPMCAS), weight ratio of 1:3 to 1:1; 45-50 wt. % of lactose monohydrate; 35-40 wt. % of microcrystalline cellulose; 4-6 wt. % of croscarmellose sodium; 0.8-1.5 wt. % of colloidal silicon dioxide; and 0.8-1.5 wt. % of magnesium stearate.

VI. DOSAGE

In one embodiment, the present invention provides a pharmaceutical composition that maybe formulated into any suitable solid dosage form. In one embodiment, a pharmaceutical composition in accordance with the present invention comprises one or more of the various embodiments of the thienotriazolodiazepine of Formula (1) as described herein in a dosage amount ranging from about 10 mg to about 100 mg. In one embodiment, the pharmaceutical composition of the present invention includes one or more of the various embodiments of the thienotriazolodiazepine of Formula (1) as described herein in a dosage amount selected from the group consisting of from about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, and about 10 mg to about 20 mg. In one embodiment, the pharmaceutical composition of the present invention includes one or more of the various embodiments of the thienotriazolodiazepine of Formula (1)

as described herein in a dosage amount selected from the group consisting of about 10 mg, about 50 mg, about 75 mg, about 100 mg.

In some embodiments, the methods of the present invention includes administering to a subject in need thereof one or more of the various embodiments of the thienotriazolodiazepine of Formula (I) as described herein in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically.

In some embodiments, the methods of the present invention includes administering to a subject in need thereof a thienotriazolodiazepine selected from the group consisting of compounds (1-1), (1-2), (1-3), (1-4), (1-5), (1-6), (1-7), (1-8), (1-9), (1-10), (1-11), (1- 12), (1-13), (1-14), (1-15), (1-16), (1-17), and (1-18), in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically.

Such unit dosage forms are suitable for administration 1 to 5 times daily depending on the particular purpose of therapy, the phase of therapy, and the like. In one embodiment, the dosage form may be administered to a subject in need thereof at least once daily for at least two successive days. In one embodiment, the dosage form may be administered to a subject in need thereof at least once daily on alternative days. In one embodiment, the dosage form may be administered to a subject in need thereof at least weekly and divided into equal and/or unequal doses. In one embodiment, the dosage form may be administered to a subject in need thereof weekly, given either on three alternate days and/or 6 times per week. In one embodiment, the dosage form may be administered to a subject in need thereof in divided doses on alternate days, every third day, every fourth day, every fifth day, every sixth day and/or weekly. In one embodiment, the dosage form may be administered to a subject in need thereof two or more equally or unequally divided doses per month.

The dosage form used, e.g., in a capsule, tablet, mini-tablet, beads, beadlets, pellets, granules, granulates, or powder may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxylpropylmethylcellulose acetate succinate (HPMCAS).

VII. PROCESS

The thienotriazolodiazepine compounds disclosed herein can exist as free base or as acid addition salt can be obtained according to the procedures described in US Patent Application Publication No. 2010/0286127, incorporated by reference in its entirety herein, or in the present application. Individual enantiomers and diastereomers of the thienotriazolodiazepine compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent.

If desired, a particular enantiomer of the thienotriazolodiazepine compounds disclosed herein may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers, thus formed by fractional crystallization or chromatographic means well known in the art, and subsequent recovery of the pure enantiomers. Various methods well known in the art may be used to prepare the thienotriazolodiazepine compounds of Formula (1) with an enantiomeric excess of generally more than about 80%. Advantageously, preferred enantiomeric excess is of more than 80%, preferably of more than 90%, more preferably of more than 95%, and most preferably of 99% and more.

The solid dispersions of the present invention can be prepared by a number of methods, including by melting and solvent evaporation. The solid dispersions of the present invention can also be prepared according to the procedures described in: Chiou W L, Riegelman S: "Pharmaceutical applications of solid dispersion systems", *J. Pharm. Sci.* 1971; 60:1281-1302; Serajuddin A T M: "Solid dispersion of poorly water-soluble drugs: early promises, subsequent problems, and recent breakthroughs", *J. Pharm. Sci.* 1999; 88:1058-1066; Leuner C, Dressman J: "Improving drug solubility for oral delivery using solid dispersions", *Eur. J. Pharm. Biopharm.* 2000; 50:47-60; and Vasconcelos T, Sarmento B, Costa P: "Solid dispersions as strategy to improve oral bioavailability of poor water soluble drugs", *Drug Discovery Today* 2007; 12:1068-1075, all of which are incorporated herein by reference in their entireties.

In one embodiment, solid dispersions of the present invention are prepared by a melting process. In one embodiment, the melting process comprises melting one or more of the various embodiments of the thienotriazolodiazepine of Formula (1) within a carrier. In one embodiment, the melting process includes cooling a melted compound of the present invention and a carrier. In one embodiment, the melting process comprises pulverization of the melted compound and the carrier. In one embodiment, a melted compound of the present invention and a carrier are pulverized following the cooling step.

In some embodiments in which the thienotriazolodiazepine of Formula (1) or a pharmaceutically acceptable salt, a solvate, including a hydrate, a racemate, an enantiomer, an isomer, or an isotopically-labeled form thereof and the carrier are incompatible, a surfactant may be added during the melting step to prevent formation of two liquid phases or a suspension in the heated mixture. In some embodiments, one or more of the various embodiments of the thienotriazolodiazepine of Formula (1) is suspended in a previously melted carrier, instead of using both drug and carrier in the melted state, thereby reducing the process temperature. In one embodiment, melted drug and carrier mixture is cooled an ice bath agitation. In one embodiment, melted drug and carrier mixture is cooled and solidified by spray cooling (alternatively spray congealing).

In one embodiment, melted drug and carrier mixture is cooled and solidified by forming the melt into particles by spraying the melt into a cooling chamber through which ambient or cooled, low temperature air is passing. In one embodiment, melted drug and carrier mixture is cooled and solidified by atomization and re-solidification of the molten dispersion in a suitable fluid bed processor. In one embodiment, melted drug and carrier mixture is cooled and solidified by melt-granulation in a heatable high-shear mixer.

In some embodiments, hot-stage extrusion or melt agglomeration may be used to avoid melting limitations of the drug. Hot-stage extrusion consists of the extrusion, at high rotational speed, of the drug and carrier, previously mixed, at melting temperature for a short period of time; the resulting product is collected after cooling at room temperature and milled.

In one embodiment, one or more of the various embodiments of the thienotriazolodiazepine of Formula (1) is processed at a reduced processing temperature to avoid degradation of any thermally labile compound. In one embodiment, the reduced processing temperature is achieved by associating a hot-stage extrusion with a temporary plasticizer such as carbon dioxide. In one embodiment, melt agglomeration is used in the preparation of solid dispersions in accordance with the present invention in conventional high shear mixers or in a rotary processors. In one embodiment, the solid dispersion in accordance with the present invention is prepared by adding a molten carrier containing a thienotriazolodiazepine compound in accordance with the present invention to a heated excipient. In one embodiment, the solid dispersion in accordance with the present invention is prepared by adding by adding a molten carrier to a heated mixture of the thienotriazolodiazepine in accordance with the present invention and one or more excipients. In one embodiment, the solid dispersion in accordance with the present invention is prepared by heating a mixture of a thienotriazolodiazepine compound in accordance with the present invention, a carrier and one or more excipients to a temperature within or above the melting range of the carrier.

In some embodiments, a one or more of the various embodiments for the formulation of the thienotriazolodiazepine, according to Formula (1), is prepared by a solvent evaporation method. In one embodiment, the solvent evaporation method comprises solubilization of a thienotriazolodiazepine compound, according to Formula (1), carrier in a volatile solvent that is subsequently evaporated. In one embodiment, the volatile solvent may one or more excipients. In one embodiment, the one or more excipients include, but are not limited to anti-sticking agents, inert fillers, surfactants wetting agents, pH modifiers and additives. In one embodiment, the excipients may dissolved or in suspended or swollen state in the volatile solvent.

In one embodiment, preparation of solid dispersions in accordance with the present invention includes drying one or more excipients suspended in a volatile solvent. In one embodiment, the drying includes vacuum drying, slow evaporation of the volatile solvent at low temperature, use of a rotary evaporator, spray-drying, spray granulation, freeze-drying, or use of supercritical fluids.

In one embodiment, spray drying preparation of a formulation for the thienotriazolodiazepine composition, according to Formula (1), is used which involves atomization of a suspension or a solution of the composition into small droplets, followed by rapid removal solvent from the formulation. In one embodiment, preparation of a formulation in accordance with the present invention involves spray granulation in which a solution or a suspension of the composition in a solvent is sprayed onto a suitable chemically and/or physically inert filler, such as lactose or mannitol. In one embodiment, spray granulation of the solution or the suspension of the composition is achieved via two-way or three-way nozzles.

In some embodiments, preparation of solid dispersions in accordance with the present invention includes use of supercritical fluids. The term "supercritical fluids" refers to substances existing as a single fluid phase above their critical temperature and critical pressure. In one embodiment, preparation of a formulation, in accordance with the present invention, includes use a supercritical carbon dioxide fluid. In one embodiment, preparation of a formulation, in accordance with the present invention, using the supercritical fluid technique comprises dissolving a thienotriazolodiazepine compound, according to Formula (1), and carrier in a common solvent that is introduced into a particle formation vessel through a nozzle, simultaneously with carbon dioxide; and spraying the solution to allow the solvent be rapidly extracted by the supercritical fluid, thereby resulting in the precipitation of solid dispersion particles on the walls of the vessel.

In some embodiments, preparation of solid dispersions in accordance with the present invention includes use of a co-precipitation method. In one embodiment, a non-solvent is added dropwise to a thienotriazolodiazepine composition, according to Formula (1), and a carrier solution, under constant stirring. In one embodiment, the thienotriazolodiazepine composition, according to Formula (1), and the carrier are co-precipitated to form microparticles during the addition of the non-solvent. In one embodiment, the resulting microparticles are filtered and dried to provide the desired solid dispersion.

The proportion of compound of Formula (1) and polymeric carrier(s) to be mixed is not particularly limited, as long as it can improve the bioavailability of the compound of Formula (1) and varies depending on the kind of polymer.

The invention is illustrated in the following non-limiting examples.

VIII. EXAMPLES

The invention is illustrated in the following non-limiting examples.

Example 1: In Vitro Screening of Solid Dispersions of Compound (1-1)

Ten solid dispersions were prepared using compound (1-1) and one of five polymers, including hypromellose acetate succinate (HPMCAS-M), hypromellose phthalate (HPMCP-HP55), polyvinylpyrrolidone (PVP), PVP-vinyl acetate (PVP-VA), and Euragit L100-55, at both 25% and 50% of compound (1-1) loading, for each polymer. Solid dispersions were prepared by a solvent evaporation method, using spray-drying followed by secondary drying in a low-temperature convection oven. The performance of each solid dispersion was assessed via a non-sink dissolution performance test which measured both the total amount of drug and the amount of free drug present in solution over time. Non-sink dissolution was chosen because it best represents the in vivo situation for low soluble compounds. This test included a "gastric transfer" of dispersion from gastric pH (0.1N NaCl, pH 1.0) to intestinal pH (FaFSSIF, pH 6.5) approximately 30 to 40 minutes after the introduction of dispersion to the test medium, simulating in vivo conditions. [FaFSSIF is Fasted State Simulated Intestinal Fluid, comprised of 3 mM sodium taurocholate, 0.75 mM lechithin, 0.174 g NaOH pellets, 1.977 g $NaH_2PO_4.H_2O$, 3.093 g NaCl, and purified water qs 500 mL.] The amount of dissolved drug was quantified using a high-performance liquid chromatography (HPLC) method and an Agilent 1100 series HPLC. The dissolution profiles of the formulations (FIGS. 1A-1J) showed large increases in drug solubility in all dispersion candidates relative to the unformulated compound in the same media. Of the solid dispersions, the 25% compound (1-1) in PVP, 25% compound (1-1) in HPMCAS-M, and 50% compound (1-1) in HPMCAS-M dispersions provided enhanced oral absorption as compared to the unformulated compound, based on finding higher levels of free drug released at intestinal pH.

Example 2: In Vivo Screening of Solid Dispersions of Compound (1-1)

The solid dispersions of compound (1-1), namely the 25% compound (1-1) in PVP, 25% compound (1-1) in HPMCAS-MG, and 50% compound (1-1) in HPMCAS-M dispersions, were prepared at larger scale for in vivo studies. Each formulation was assessed in the in vitro dissolution test described in Example 1. To ensure that these dispersions were both amorphous and homogeneous, each dispersion was assessed by powder x-ray diffraction (PXRD) and modulated differential scanning calorimetry (mDSC). The x-ray diffractomer was a Bruker D-2 Phaser. Additionally, to understand the effect of water on the glass transition temperature (Tg) for each dispersion, mDSC was performed on samples first equilibrated at a set relative humidity (i.e., 25%, 50%, and 75% RH) for at least 18 hours. [Water can act as a plasticizer for solid dispersions and the hygroscopicity of the system due to the active compound or polymer can affect the amount of water uptake by these systems.]

The non-sink dissolution results (FIGS. 2A-2C) were comparable to those found for the dispersions in Example 1. PXRD results (FIG. 3) showed no evidence of crystalline compound in any of the dispersions and mDSC results (FIGS. 4A-4C) showed a single glass transition temperature (Tg) for each dispersion, indicating that each dispersion was homogeneous. An inverse relationship between Tg and relative humidity was observed for each (FIG. 5). Notably, for the 25% compound (1-1) in PVP solid dispersion equilibrated at 75% RH, there appeared to be two Tgs, indicating that phase separation was occurring, and this dispersion also showed a melt event at 75% RH, suggesting that crystallization occurred during the RH equilibration (FIG. 6). This finding suggests that the 25% compound (1-1) in PVP dispersion may be less stable than the HPMCAS-M dispersions.

To assess the bioavailability of the three dispersions, groups of male beagle dogs (three per group) were given a 3 mg/kg dose of an aqueous suspension of solid dispersion of compound (1-1) administered by oral gavage or a 1 mg/kg dose of compound (1-1) dissolved in water:ethanol:polyethylene glycol (PEG) 400 (60:20:20) and administered as an intravenous bolus into the cephalic vein. Blood samples were collected from the jugular vein of each animal at 0 (pre-dose), 5, 15, and 30 minutes and 1, 2, 4, 8, 12, and 24 hours following intravenous administration and at 0 (pre-dose), 15 and 30 minutes and 1, 2, 4, 8, 12, and 24 hours following oral gavage administration. The amount of compound (1-1) present in each sample was detected using a qualified LC-MS/MS method with a lower limit of quantification of 0.5 ng/mL. The area under the plasma concentration-time curve (AUC) was determined by use of the linear trapezoidal rule up to the last measurable concentration without extrapolation of the terminal elimination phase to infinity. The elimination half-life ($t_{1/2}$) was calculated by least-squares regression analysis of the terminal linear part of the log concentration-ime curve. The maximum plasma concentration ($C_{max}$) and the time to $C_{max}$ ($t_{max}$) were derived directly from the plasma concentration data. The oral bioavailability (F) was calculated by dividing the dose normalized AUC after oral administration by the dose normalized AUC after intravenous administration and reported as percentages (%). Results, summarized in Table 1 below, gave mean oral bioavailabilities of the 25% compound (1-1) in PVP, 25% compound (1-1) in HPMCAS-M, and 50% compound (1-1) in HPMCAS-M solid dispersions of 58%, 49%, and 74%, respectively.

TABLE 1 pharmacokinetic parameters of compound (1-1) after oral (po) and intravenous (iv) administrations to dogs (the values are averages from three dogs)

| Compound (1-1) formulation | Dose & Route | $C_{max}$ (ng/L) | $t_{max}$ (hr) | AUC (ng · min/mL) | $t_{1/2}$ (hr) | F (%) |
|---|---|---|---|---|---|---|
| Solution in water:ethanol:PEG400 (60:20:20) | 1 mg/kg IV | 769 | 0.083 | 53,312 | 1.5 | — |

TABLE 1-continued pharmacokinetic parameters of compound (1-1) after oral (po) and intravenous (iv) administrations to dogs (the values are averages from three dogs)

| Compound (1-1) formulation | Dose & Route | $C_{max}$ (ng/L) | $t_{max}$ (hr) | AUC (ng · min/mL) | $t_{1/2}$ (hr) | F (%) |
|---|---|---|---|---|---|---|
| Aqueous suspension of 25% compound (1-1)/PVP solid dispersion | 3 mg/kg PO | 487 | 1.0 | 93,271 | 1.6 | 58 |
| Aqueous suspension of 25% compound (1-1)/HPMCAS-M solid dispersion | 3 mg/kg PO | 228 | 0.5 | 78,595 | 2.0 | 49 |
| Aqueous suspension of 50% compound (1-1)/HPMCAS-M solid dispersion | 3 mg/kg PO | 371 | 1.0 | 118,174 | 1.5 | 74 |

AUC: area under the plasma concentration-time curve; $C_{max}$: maximum plasma concentration; F: bioavailability; HPMCAS: hypromellose acetate sodium; IV: intravenous; PEG: polyethylene glycol; PO; per os, oral; PVP: polyvinylpyrrolidone; $t_{max}$: time of $C_{max}$; $t_{1/2}$: plasma elimination half-life

Example 3: Preparation and Clinical Use of Capsules Containing a Solid Dispersion of Compound (1-1)

A gelatin capsule of 10 mg strength was prepared for initial clinical studies in patients with hematologic malignancies. Based on results of in vitro and in vivo testing of solid dispersions of compound (1-1), as described in Examples 1 and 2, a 50% compound (1-1) in HPMCAS-M solid dispersion was selected for capsule development. Capsule development was initiated targeting a fill weight of 190 mg in a size 3 hard gelatin capsule, as this configuration would potentially allow increasing the capsule strength by filling a larger size capsule while maintaining the pharmaceutical composition. Based on experience, four capsule formulations were designed with different amounts of disintegrant and with and without wetting agent. Since all four formulations showed similar disintegration test and dissolution test results, the simplest formulation (without wetting agent and minimum disintegrant) was selected for manufacturing. Manufacturing process development and scale-up studies were performed to confirm the spray drying process and post-drying times for the solid dispersion; blending parameters; roller compaction and milling of the blend to achieve target bulk density of approximately 0.60 g/cc; and capsule filling conditions.

Crystalline compound (1-1) and the polymer hypromellose acetate succinate (HPMCAS-M) were dissolved in acetone and spray-dried to produce solid dispersion intermediate (SDI) granules containing a 50% compound (1-1) loading. The SDI was shown by PXRD analysis to be amorphous and by mDSC analysis to be homogeneous (i.e., single Tg under ambient conditions). The 50% compound (1-1) in HPMCAS-M solid dispersion (1000 g) and excipients, including microcrystalline cellulose filler-binder (4428 g), croscarmellose sodium disintegrant (636 g), colloidal silicon dioxide dispersant/lubricant 156 g), magnesium stearate dispersant/lubricant (156 g), and lactose monohydrate filler (5364 g) were blended in stages in a V-blender. The blend was them compacted and granulated to obtain a bulk density of approximately 0.6 g/mL. The blend was dispensed into size 3 hard gelatin capsules (target fill weight: 190 mg) using an automated filling machine and finished capsules were polished using a capsule polisher machine.

Pharmacokinetic assessments were performed following oral dosing of 10 mg capsules containing the 50% compound (1-1) in HPMCAS solid dispersion and results were compared with pharmacokinetic assessments performed following oral dosing of administration of 4×10 mg capsules containing the Eudragit solid dispersion of compound (1-1) to healthy volunteers A comparison of the two pharmaceutical compositions is provided in Tables 2A and 2B below. The Eudragit formulation previously was described in Example 5 in US Patent Application 2009/0012064 A1, published Jan. 8, 2009. That application noted that the Eudragit solid dispersion formulation was made by dissolving and/or dispersing the thienotriazolodiazepine of formula (A) and coating excipients, including ammonio methacrylate copolymer type B (Eudragit RS), methacrylic acid copolymer type C (Eudragit L100-55), talc, and magnesium aluminosilicate, in a mixture of water and ethanol. This heterogeneous mixture then was applied to microcrystalline cellulose spheres (Nonpareil 101, Freund) using a centrifugal fluidizing bed granulator to produce granules that were dispensed into size 2 hydroxypropyl methylcellulose capsules.

In both clinical studies, blood levels of compound (1-1) were determined using validated LC-MS/MS methods and pharmacokinetic analyses were performed based on plasma concentrations of compound (1-1) measured at various time points over 24 hours after capsule administration. Results, summarized in Table 3 below, showed that the HPMCAS-M solid dispersion formulation had over 3-fold higher bioavailability in humans than the Eudragit solid dispersion formulation based on AUCs (924*4/1140, adjusting for difference in doses administered). Additionally, based on the observed $T_{max}$, the HPMCAS formulation is more rapidly absorbed than the Eudragit formulation ($T_{max}$ of 1 h vs 4-6 h). The marked improvement in systemic exposure with the HPMCAS-M solid dispersion formulation is unexpected.

TABLE 2A solid dispersion capsules of compound (1-1) for clinical use pharmaceutical composition containing 50% HPMCAS solid dispersion of compound (1-1): 10 mg strength, size 3 hard gelatin capsule

| Ingredient | Function | Capsule Content mg | Wt % |
|---|---|---|---|
| Compound of formula (II) | active agent | 10.0* | 5.56 |
| Hypromellose acetate succinate (HPMCAS-M) | carrier for solid dispersion | 10.0 | 5.56 |
| Lactose monohydrate | filler | 85.0 | 47.22 |
| Microcrystalline cellulose | filler-binder | 70.0 | 38.89 |

TABLE 2A-continued solid dispersion capsules of compound (1-1) for clinical use pharmaceutical composition containing 50% HPMCAS solid dispersion of compound (1-1): 10 mg strength, size 3 hard gelatin capsule

| | | Capsule Content | |
|---|---|---|---|
| Ingredient | Function | mg | Wt % |
| Croscarmellose sodium | disintegrant | 10.0 | 5.56 |
| Collidal silicon dioxide | dispersant/lubricant | 2.5 | 1.39 |
| Magnesium stearate | dispersant/lubricant | | |
| Total | | 190.0 | 100.0 |

TABLE 2B pharmaceutical composition containing Eudragit L100-55 solid dispersion of compound (1-1): 10 mg strength, size 2 hard gelatin capsule

| | | Capsule Content | |
|---|---|---|---|
| Ingredient | Function | mg | Wt % |
| Compound (1-1) | active agent | 10.0* | 3.8 |
| Core: | | | |
| Microcrystalline cellulose spheres (Nonpareil 101, Freund, Inc) | vehicle | 100.0 | 38.5 |
| Compound/polymer layer: | | | |
| Ammonio methacrylate copolymer, type B (NF. PhEur) (Edragit RS, Evonik) | coating agent | 10.8 | 4.2 |
| Methacrylic acid copolymer, type C (NF)/Methacrylic acid-ethyl acrylate copolymer (1:1) type A (PhEur) (Eudragit L100-55, Evonik) | coating agent | 25.2 | 9.7 |
| Talc | coating agent | 88.2 | 33.9 |
| Magnesium aluminometasilicate (Neuslin, Fuji Chemical) | coating agent | 20.0 | 7.7 |
| Triethyl citrate | plasticizer | 5.0 | 1.9 |
| Silicon dioxide | fluidizing agent | 0.8 | 0.3 |
| | | 260.0 | 100.0 |

*as anhydrate

TABLE 3 pharmacokinetic parameters following oral administration of solid dispersions of compound (1-1) to humans

| Compound (1-1) formulation | # Patients | Dose and Route | $C_{max}$ (ng/mL) | $T_{max}$ (hr) | $AUC_{0\text{-}24\ h}$ (ng · h/mL) |
|---|---|---|---|---|---|
| Eudragit solid dispersion formulation | 7 | 40 mg PO | 83 | 4 to 6 | 1140 |
| 50% HMPCAS-M solid dispersion formulation | 7 | 10 mg PO | 286 | 1 | 925 |

$AUC_{0\text{-}24\ h}$: area under the OTX015 plasma concentration vs. time curve over 24 hours
$C_{max}$: maximum concentration in plasma
hr: hour
HPMCAS: hypromellose acetate succinate
mL: milliliter
ng: nanogram
PO: per os, oral
$T_{max}$: time of $C_{max}$ Example 4. Oral Exposure in the Rat The oral bioavailability of three formulations of solid dispersions of compound (1-1) was determined in rats. The three dispersions chosen were the 25% dispersion of compound (1-1) in PVP, the 25% dispersion of compound (1-1) in HPMCAS-MG, and the 50% dispersion of compound (1-1) in HPMCAS-MG. The animals used in the study were Specific Pathogen Free (SPF) Hsd:Sprague Dawley rats obtained from the Central Animal Laboratory at the University of Turku, Finland. The rats were originally purchased from Harlan, The Netherlands. The rats were female and were ten weeks of age, and 12 rats were used in the study. The animals were housed in polycarbonate Makrolon II cages (three animals per cage), the animal room temperature was 21+/−3° C., the animal room relative humidity was 55+/−15%, and the animal room lighting was artificial and was cycled for 12 hour light and dark periods (with the dark period between 18:00 and 06:00 hours). Aspen chips (Tapvei Oy, Estonia) were used for bedding, and bedding was changed at least once per week. Food and water was provided prior to dosing the animals but was removed during the first two hours after dosing.

The oral dosing solutions containing the 25% dispersion of compound (1-1) in PVP, the 25% dispersion of compound (1-1) in HPMCAS-MG, and the 50% dispersion of compound (1-1) in HPMCAS-MG were prepared by adding a pre-calculated amount of sterile water for injection to containers holding the dispersion using appropriate quantities to obtain a concentration of 0.75 mg/mL of compound (1-1). The oral dosing solutions were subjected to vortex mixing for 20 seconds prior to each dose. The dosing solution for intravenous administration contained 0.25 mg/mL of compound (1-1) and was prepared by dissolving 5 mg of compound (1-1) in a mixture containing 4 mL of polyethylene glycol with an average molecular weight of 400 Da (PEG400), 4 mL of ethanol (96% purity), and 12 mL of sterile water for injection. The dosing solution containing the 25% dispersion of compound (1-1) in PVP was used within 30 minutes after the addition of water. The dosing solutions containing the 25% dispersion of compound (1-1) in HPMCAS-MG and the 50% dispersion of compound (1-1) in HPMCAS-MG were used within 60 minutes of after the addition of water. A dosing volume of 4 mL/kg was used to give dose levels of compound (1-1) of 1 mg/kg for intravenous administration and 3 mg/kg for oral administration. The dosing scheme is given in Table 4.

TABLE 4

Dosing scheme for rat oral exposure study.

| Rat | Weight | Dose (mL) | Test Item | Route |
|---|---|---|---|---|
| 1 | 236.5 | 0.95 | Compound (1-1) | intravenous |
| 2 | 221 | 0.88 | Compound (1-1) | intravenous |
| 3 | 237.5 | 0.95 | Compound (1-1) | intravenous |
| 4 | 255.5 | 1.02 | 25% dispersion of compound (1-1) in PVP | oral |
| 5 | 224.2 | 0.90 | 25% dispersion of compound (1-1) in PVP | oral |
| 6 | 219.2 | 0.88 | 25% dispersion of compound (1-1) in PVP | oral |
| 7 | 251.6 | 1.01 | 25% dispersion of compound (1-1) in HPMCAS-MG | oral |
| 8 | 240.4 | 0.96 | 25% dispersion of compound (1-1) in HPMCAS-MG | oral |
| 9 | 238 | 0.95 | 25% dispersion of compound (1-1) in HPMCAS-MG | oral |

TABLE 4-continued

Dosing scheme for rat oral exposure study.

| Rat | Weight | Dose (mL) | Test Item | Route |
|---|---|---|---|---|
| 10 | 226.6 | 0.91 | 50% dispersion of compound (1-1) in HPMCAS-MG | oral |
| 11 | 228.4 | 0.91 | 50% dispersion of compound (1-1) in HPMCAS-MG | oral |
| 12 | 228.5 | 0.91 | 50% dispersion of compound (1-1) in HPMCAS-MG | oral |

Blood samples of approximately 50 µL were collected into Eppendorf tubes containing 5 µL of ethylenediaminetetraacetic acid (EDTA) solution at time points of 0.25, 0.5, 1, 2, 4, 8, 12, and 24 hours after dosing, with each sample collected within a window of 5 minutes from the prescribed time point. From each sample, 20 µL of plasma was obtained and stored at dry ice temperatures for analysis. Analysis of each sample for the concentration of compound (1-1) was performed using a validated liquid chromatography tandem mass spectrometry (LC-MS/MS) method with a lower limit of quantitation of 0.5 ng/mL.

Pharmacokinetic parameters were calculated with the Phoenix WinNonlin software package (version 6.2.1, Pharsight Corp., CA, USA) with standard noncompartmental methods. The elimination phase half-life ($t_{1/2}$) was calculated by least-squares regression analysis of the terminal linear part of the log concentration-time curve. The area under the plasma concentration-time curve (AUC) was determined by use of the linear trapezoidal rule up to the last measurable concentration and thereafter by extrapolation of the terminal elimination phase to infinity. The mean residence time (MRT), representing the average amount of time a compound remains in a compartment or system, was calculated by extrapolating the drug concentration profile to infinity. The maximum plasma concentration ($C_{max}$) and the time to $C_{max}$ ($t_{max}$) were derived directly from the plasma concentration data. The tentative oral bioavailability (F) was calculated by dividing the dose normalised AUC after oral administration by the dose normalised AUC after intravenous administration, i.e. F=(AUC(oral)/Dose(oral))/(AUC(intravenous)/Dose(intravenous))] and is reported as percentage (%).

The pharmacokinetic parameters are given in Table 5, and the plasma concentration versus time plots are shown in FIGS. 7 and 8.

TABLE 5

Pharmacokinetic parameters of compound (1-1) after oral and intravenous administrations. The values are an average from three animals.

| Compound | Parameter | 1 mg/kg intravenous | 3 mg/kg oral | F(%) |
|---|---|---|---|---|
| Compound (1-1) water:ethanol:PEG 400 (60:20:20) | AUC (min*ng/ml) | 74698 | | |
| | $C_{max}$ (ng/ml) | 730 | | |
| | $T_{max}$ (hr) | 0.25 | | |
| | $t_{1/2}$ (hr) 8.5 | 8.5 | | |
| | Cl/F (ml/min/kg) | 13.4 | | |
| | MRT (hr) | 7.4 | | |
| 25% dispersion of compound (1-1) in PVP | AUC (min*ng/ml) | | 39920 | 18 |
| | $C_{max}$ (ng/ml) | | 77.9 | |
| | $T_{max}$ (hr) | | 1 | |
| | $t_{1/2}$ (hr) 8.5 | | 13.8 | |
| | Cl/F (ml/min/kg) | | 75.2 | |
| | MRT (hr) | | 18.0 | |
| 25% dispersion of compound (1-1) in HPMCAS-MG | AUC (min*ng/ml) | | 35306 | 16 |
| | $C_{max}$ (ng/ml) | | 48.3 | |
| | $T_{max}$ (hr) | | 0.5 | |
| | $t_{1/2}$ (hr) 8.5 | | 11.0 | |
| | Cl/F (ml/min/kg) | | 85.0 | |
| | MRT (hr) | | 17.1 | |
| 50% dispersion of compound (1-1) in HPMCAS-MG | AUC (min*ng/ml) | | 40238 | 18 |
| | $C_{max}$ (ng/ml) | | 67.0 | |
| | $T_{max}$ (hr) | | 2 | |
| | $t_{1/2}$ (hr) 8.5 | | 9.5 | |
| | Cl/F (ml/min/kg) | | 74.6 | |
| | MRT (hr) | | 12.8 | |

Example 5. Preparation of Spray Dried Dispersions

Spray dried dispersions of compound (1-1) were prepared using five selected polymers: HPMCAS-MG (Shin Etsu Chemical Co., Ltd.), HPMCP-HP55 (Shin Etsu Chemical Co., Ltd.), PVP (ISP, a division of Ashland, Inc.), PVP-VA (BASF Corp.), and Eudragit L100-55 (Evonik Industries AG). All spray dried solutions were prepared at 25% and 50% by weight with each polymer. All solutions were prepared in acetone, with the exception of the PVP solutions, which were prepared in ethanol. For each solution, 1.0 g of solids (polymer and compound (1-1)) were prepared in 10 g of solvent. The solutions were spray dried using a Büchi B-290, PE-024 spray dryer with a 1.5 mm nozzle and a Büchi B-295, P-002 condenser. The spray dryer nozzle pressure was set to 80 psi, the target outlet temperature was set to 40° C., the chiller temperature was set to −20° C., the pump speed was set to 100%, and the aspirator setting was 100%. After spray drying, the solid dispersions were collected and dried overnight in a low temperature convection oven to remove residual solvents.

Example 6: Stability with Humidity and Temperature

TABLE 6

| Test | Procedure | Acceptance Criteria | T = 0 (Initial) | T-1 month (storage at 40° C./75% RH) | T-2 month (storage at 40° C./75% RH) | T = 3 month (storage at 40° C./75% RH) |
|---|---|---|---|---|---|---|
| Appearance | AM-0002 | White to off-white powder | Test Date/Ref: 6 Aug. 2012/02-41-2 White Powder | Test Date/Ref: 24 Sep. 2012/02-41-59 White Powder | Test Date/Ref: 24 Oct. 2012/02-37-106 White Powder | Test Date/Ref: 17 Dec. 2012/02-37-119 White Powder |
| Potency (HPLC) | AM-0028 | 45.0-55.0 wt % | Test Date/Ref: 25 Jul. 2012/02-37-21 50.0 | Test Date/Ref: 25 Sep. 2012/02-4HI0 49.4 | Test Date/Ref: 24 Oct. 2012/02-37-105 49.8 | Test Date/Ref: 29 Nov. 2012/02-34-107 49.2 |

TABLE 6-continued

| Test | Procedure | Acceptance Criteria | T = O (Initial) | T-1 month (storage at 40° C./75% RH) | T-2 month (storage at 40° C./75% RH) | T = 3 month (storage at 40° C./75% RH) |
|---|---|---|---|---|---|---|
| Individual Related Substances (HPLC) | AM-0029 | Report results | Test Date/Ref: 25 Jul. 2012/02-34-49 RRT    % Area No reportable related substances | Test Date/Ref: 26 Sep. 2012/02-41-64 RRT    % Area No reportable related substances | Test Date/Ref: 24 Oct. 2012/02-37-105 RRT    % Area 0.68    0.06 0.77    0.06 | Test Date/Ref: 29 Nov. 2012/02-34-107 RRT    % Area 0.68    0.07 0.77    0.09 |
| Total Related Substances (HPLC) | AM•0029 | Report results | Test Date/Ref: 25 Jul. 2012/02-34-49 No reportable related substances | Test Date/Ref: 26 Sep. 2012/02-41-64 No reportable related substances | Test Date/Ref: 24 Oct. 2012/02-37-105 0.12% | Test Date/Ref: 29 Nov. 2012/02-34-107 0.16% |
| Water Content (KF) | AM-0030 USP <921> | Report results (wt %) | Test Date/Ref: 2 Aug. 2012/02-41-1 1.52 | Test Date/Ref: 27 Sep. 2012/02-37-99 2.53 | Test Date/Ref: 25 Oct. 2012102-37-110 2.70 | Test Date/Ref: 29 Nov. 2012/02-37-116 3.43 |
| X-Ray Powder Diffraction (XRPD) | USP <941> | Consistent with an amorphous form | Test Date/Ref: 24 Jul. 2012/02-24-131 Consistent with an amorphous form See FIG. 9 | Test Date/Ref: 1 Oct. 2012/02-41-73 Consistent with an amorphous form See FIG. 10 | Test Date/Ref: 24 Oct. 2012/02-37-107 Consistent with an amorphous form See FIG. 11 | Test Date/Ref: 17 Dec. 2012/02-37-120 Consistent with an amorphous form See FIG. 12 |
| Modulated Differential Scanning Calorimetry (mDSC) | USP <891> (n = 2 replicates) | Report individual and average glass transtion temperatures ($T_g$, ° C.) | Test Date/Ref: 24 Jul. 2012/02-24-130 Replicate 1 = 134.30° C., Replicate 2 = 134.23° C., Replicate 3 = 135.28° C., Average = 134.60° C. | Test Date/Ref: 26 Sep. 2012/02-37-98 Replicate 1 = 134.65° C., Replicate 2 = 134.43° C., Average = 134.54° C. | Test Date/Ref: 24 Oct. 2012/02-37-108 Replicate 1 = 135.35° C., Replicate 2 = 134.93° C., Average = 135.14° C. | Test Date/Ref: 17 Dec. 2012/02-37-121 Replicate 1 = 134.36° C. Replicate 2 = 137.16° C. Average = 135.76° C. |

Spray dried dispersions of compound (1-1) in HPMCAS-MG were assessed for stability by exposure to moisture at elevated temperature. The glass transition temperature (Tg) as a function of relative humidity was determined at 75% relative humidity, 40° C. for 1, 2 and 3 months. The spray dried dispersion was stored in an LDPE bag inside a HDPE bottle to simulate bulk product packaging. The results are summarized in Table 6. At time zero, the Tg was 134° C., at 1 month the Tg was 134° C., at 2 months the Tg was 135° C. and at 3 months the Tg was 134° C. and only a single inflection point was observed for each measurement. X-ray diffraction patterns were also obtained for each sample. FIG. 9 illustrates a powder X-ray diffraction profile of solid dispersions of compound (1-1) in HPMCAS-MG at time zero of a stability test. FIGS. 10, 11 and 12 illustrate powder X-ray diffraction profiles of solid dispersions of compound (1-1) in HPMCAS-MG after 1 month, 2 months and 3 months, respectively, after exposure at 40° C. and 75% relative humidity. The patterns did not show any diffraction lines associated with compound (1-1).

Example 7: In Vitro Evaluation of Compound (1-1) as Single Agent and in Combination with Standard Chemotherapy Drugs in Human Leukemic Cell Lines Material and Methods:

Eight established human cell lines from both acute and chronic acute myeloid leukemia (AML, i.e. HL-60 and U-937; CML, i.e. K-562 and NALM-1) and acute lymphoblastic leukemia (ALL, i.e. Jurkat, CCRF-CEM, MOLT-3 and -4) were treated by increasing doses of compound (1-1). MTT assays were performed after 72 hours exposure. Protein levels were analyzed by Western Blot using commercial antibodies. RNA was extracted using the Qiagen RNAEasy and RT-PCR was performed using Fast SYBR Green on a StepOnePlus Real-Time PCR System. Combination effects were evaluated in four cell lines (HL60, U937, Jurkat and K562); compound (1-1) was administered with daunorubicin, azacytidine, dexamethasone, cytarabine or methotrexate. The 48 h Combination Index (CI) was determined by median effect plot analysis using CalcuSyn software expressed as the median and range of CI values among cell lines (Chou & Talalay analysis). CI<1 reflects synergy effects, CI=1 reflects additivity and CI>1 reflects antagonist effects.

Results:

The anti-proliferative effect of single-agent compound (1-1) was assessed in a panel of AML, ALL and CML cell lines, GI50s values were between 230 and 384 nM after a 72-h exposure in HL60, U937 and Jurkat, while the GI50 for the rest was ≥1,000 nM. Both compound (1-1)-sensitive and -resistant cells showed similar basal expression levels of BRD4/3/2, c-MYC, BCL-2, p21 and CyclinD1 proteins. In sensitive cell lines, compound (1-1) caused cell cycle arrest in G1 in a time-dependent manner without induction of apoptosis. Likewise, cMYC mRNA and protein levels were down-regulated after 6-h and up to 72-h treatment with 500 nM compound (1-1). In Jurkat cells, compound (1-1) induced up-regulation of mRNA levels of BRD2 and BRD4 without modifying protein levels. On the other hand, the compound (1-1)-resistant cell line K562 showed decreased levels of c-MYC RNA after 4-h and 24-h exposure while cMYC protein levels were constant even after 72 h of treatment. Synergy was observed with daunorubicin in compound (1-1)-sensitive and -resistant cell lines (CI=0.8; 0.4-0.9). The combination of compound (1-1) with azacytine or cytarabine was synergistic (CI=0.6; 0.6-0.7 and CI=0.8; 0.4-0.9, respectively) despite primary resistance of Jurkat and K562 lines to either of the individual drugs. Methotrexate, dexamethasone and panobinostat (a broad-spectrum HDAC inhibitor), exerted synergistic effects with compound (1-1) in 3 out of 4 cell lines (CI=0.5; 0.2-0.9; CI=0.3; 0.1-0.7 and CI=0.6; 0.5-0.7).

Example 8: In Vitro Evaluation of Compound (1-1) as Single Agent and in Combination with Standard Chemotherapy Drugs in Human Leukemic Cell Lines Four established human cell lines derived from acute (HL60, U937), chronic (K562) myeloid leukemia, and acute lymphoblastic leukemia (Jurkat) were treated with increasing compound (1-1) doses. MTT assays were performed after 72 h exposure. $GI_{50}$ and Emax values were calculated with the equation for sigmoidal dose response using Prism 5.00. Results are the mean±95% CI of at least 3 independent experiments performed in triplicate. Cell lines with GI50 values <500 nM were considered compound (1-1) sensitive. Protein levels were analyzed by Western Blot using commercial antibodies. For cell cycle analysis and apoptosis induction, cells were stained with PI or Annexin V respectively, and analyzed using a FACScan flow cytometer. RT-PCR was performed using Fast SYBR Green Master Mix on a StepOnePlus Real-Time PCR System. Cell cycle, apoptosis induction and qRT-PCR results are the mean±SD of at least 3 independent experiments, where $*p<0.05$, $p<0.001$ and $*p<0.0001$ versus control cells (0.1% DMSO), employing Anova then Dunnett's Multiple Comparison Test. Compound (1-1) combination studies were performed in cell lines exposed for 48 h to increasing doses of compound (1-1) alone or in combination several conventional anti-leukemic drugs, such as epigenetic modulators, steroids, m-TOR inhibitors and classical cytotoxic agents, and assessed using the Chou & Talalay method. For the sequential combination schemes, cell lines were exposed to azacytidine or panobinostat for 48 or 72 h, washed with drug-free medium and then treated with compound (1-1) for 24 or 48 h. The Combination Index (CI) was determined by median effect plot analysis using CalcuSyn software. CI<1 reflects synergy, CI=1 additivity and CI>1 antagonist effects. Results represent the median and range of 4 independent experiments performed in triplicate.

Generally compound (1-1) displays in vitro antiproliferative effects in leukemic cell lines, in the sub-micromolar range concomitant with the onset of cell cycle arrest in the G1 phase. Compound (1-1) enhances in vitro antiproliferative effects of standard antileukemic agents supporting combination therapy as a promising step in the clinical development plan. As shown in FIG. 13, compound (1-1) induced antiproliferative effects at concentrations achievable in vivo in three compound (1-1) sensitive cell lines (HL60, U937 and Jurkat) bearing different oncogenic mutations and one resistant line (K562). In FIG. 14, compound (1-1) increased proportion of cells in cell cycle phase G0/G1 with a slight induction of apoptosis in compound (1-1) sensitive leukemic cells after 48 h exposure to 500 nM compound (1-1).

In FIGS. 15A to 15F, compound (1-1) induced a rapid and sustained downregulation of c-MYC mRNA and protein levels in compound (1-1) sensitive cell lines. In FIGS. 16A to 16G, it is shown that compound (1-1) antiproliferative activity is not directly related to basal levels of BRD2/3/4, c-MYC, BCL2 or P21 mRNA or protein expression. In FIGS. 17A and 17B compound (1-1) is shown to exert strong synergistic effects in concomitant combination with demethylating agents, HDAC and mTOR inhibitors, glucocorticoids, and conventional cytotoxic drugs in both OTX015-sensitive and resistant leukemic cells lines.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method of treating leukemia cancer independently selected from the group consisting of: acute lymphoblastic leukemia (ALL), acute myelogenous leukemia (AML) (or myeloblastic), chronic lymphocytic leukemia (CLL), and chronic myelogenous leukemia (CIVIL) in a mammal comprising the step of:
   administering to a patient a pharmaceutically acceptable amount of a compound which is amorphous (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate formed in a solid dispersion having an X-ray powder diffraction pattern substantially free of diffraction lines associated with crystalline (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide dihydrate and a pharmaceutically acceptable polymer which is hydroxypropylmethylcellulose acetate succinate, having a compound:polymer weight ratio of 1:3 to 1:1 and single glass transition temperature (Tg) inflection point ranging from about 130° C. to about 140° C.

2. The method according to claim 1, further comprising: administering at least one other therapeutic agent.

3. The method according to claim 2, wherein (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide dihydrate and the at least one other therapeutic agent are administered concomitant.

4. The method according to claim 2, wherein (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide dihydrate or the pharmaceutically acceptable salt thereof and the at least one other therapeutic agent are administered sequentially.

5. The method according to claim 2, wherein the at least one other therapeutic agent is independently selected from the group consisting of an epigenetic modulator, a glucocorticoid, an m-TOR inhibitor, an HDAC-inhibitor, demethylating agent, an anthracycline, an analogue of cytidine and a cytotoxic drug.

6. The method according to claim 5, wherein the demethylating agent is decitabine.

7. The method according to claim 5, wherein the HDAC-inhibitor is vorinostat or panobinostat.

8. The method according to claim 5, wherein the mTOR inhibitor is everolimus.

9. The method according to claim 5, wherein the cytotoxic drug is selected from the group consisting of cytarabine or methotrexate.

10. The method according to claim 5, wherein the analogue of cytidine is azacytidine.

11. The method according to claim 5, wherein the anthracycline is daunorubicin.

12. The method according to claim 5, wherein the glucocorticoid is dexamethasone.

13. The method according to claim 1, wherein the solid dispersion has powder x-ray diffraction profile substantially as shown in FIG. 3.

14. The method according to claim 1, wherein the single glass transition temperature (Tg) inflection point is substantially as shown in FIG. 4C.

* * * * *